(12) United States Patent
Oda et al.

(10) Patent No.: US 9,345,558 B2
(45) Date of Patent: May 24, 2016

(54) SELF-LIGATING ORTHODONTIC BRACKET AND METHOD OF MAKING SAME

(75) Inventors: Todd I. Oda, Torrance, CA (US);
Andres Rodriguez, Alhambra, CA (US)

(73) Assignee: Ormco Corporation, Orange, CA (US)

(*) Notice: Subject to any disclaimer, the term of this patent is extended or adjusted under 35 U.S.C. 154(b) by 0 days.

(21) Appl. No.: 13/221,206

(22) Filed: Aug. 30, 2011

(65) Prior Publication Data
US 2012/0058442 A1    Mar. 8, 2012

Related U.S. Application Data

(60) Provisional application No. 61/380,046, filed on Sep. 3, 2010.

(51) Int. Cl.
*A61C 3/00* (2006.01)
*A61C 7/28* (2006.01)

(52) U.S. Cl.
CPC ........................................ *A61C 7/287* (2013.01)

(58) Field of Classification Search
CPC ............ A61C 7/287; A61C 7/30; A61C 7/34; B29D 99/00
USPC ............................................ 433/8–13, 14–17
See application file for complete search history.

(56) References Cited

U.S. PATENT DOCUMENTS

| | | | |
|---|---|---|---|
| 2,230,315 A | 2/1941 | Winslow | |
| 3,748,740 A | 7/1973 | Wildman | |
| 3,772,787 A | 11/1973 | Hanson | |
| 3,835,539 A | 9/1974 | Wallshein | |
| 3,871,096 A | 3/1975 | Wallshein | |
| 4,023,274 A | 5/1977 | Wallshein | |
| 4,144,642 A | 3/1979 | Wallshein | |
| 4,197,642 A * | 4/1980 | Wallshein | 433/11 |
| 4,209,906 A * | 7/1980 | Fujita | A61C 7/287 |
| | | | 433/11 |
| 4,248,588 A | 2/1981 | Hanson | |
| 4,260,375 A | 4/1981 | Wallshein | |
| 4,310,354 A | 1/1982 | Fountain et al. | |
| 4,386,909 A | 6/1983 | Hanson | |
| 4,443,189 A | 4/1984 | Wildman | |
| 4,492,573 A | 1/1985 | Hanson | |
| 4,496,318 A | 1/1985 | Connelly, Jr. | |
| 4,559,012 A * | 12/1985 | Pletcher | 433/10 |

(Continued)

FOREIGN PATENT DOCUMENTS

| | | |
|---|---|---|
| CN | 101014296 | 8/2007 |
| CN | 201529166 U | 7/2010 |

(Continued)

OTHER PUBLICATIONS

Japan Patent Office, Official Action issued in Japanese Patent Application No. 2011-191536 dated Aug. 17, 2015.

(Continued)

*Primary Examiner* — Cris L Rodriguez
*Assistant Examiner* — Mirayda A Aponte
(74) *Attorney, Agent, or Firm* — Wood, Herron & Evans, LLP

(57) ABSTRACT

An orthodontic bracket for coupling an archwire with a tooth includes a bracket body configured to be mounted to the tooth and a clip. A clip slot extends through the bracket body transversely to the archwire slot. Upon deflection of the clip, it contacts the bracket body at locations that were not in contact before the deflection. The clip may also have various forms and include various structures that cooperate with the body when the clip is deflected to restrict or stop the deflection. The orthodontic bracket may include a securing mechanism that is configured to secure the resilient ligating clip in the closed position. A method of manufacturing a shaped unsintered body for use in manufacturing an orthodontic bracket is provided. A portion of the sinterable particles may be removed using a stream of energy to yield a plurality of posts which are then deformed.

29 Claims, 33 Drawing Sheets

(56) References Cited

U.S. PATENT DOCUMENTS

| | | |
|---|---|---|
| 4,698,017 A | 10/1987 | Hanson |
| 4,725,229 A | 2/1988 | Miller |
| 5,094,614 A | 3/1992 | Wildman |
| 5,154,607 A | 10/1992 | Hanson |
| 5,160,261 A | 11/1992 | Peterson |
| 5,224,858 A | 7/1993 | Hanson |
| 5,269,681 A | 12/1993 | Degnan |
| 5,275,557 A | 1/1994 | Damon |
| 5,299,934 A | 4/1994 | Suyama |
| 5,320,525 A | 6/1994 | Forster |
| 5,322,435 A | 6/1994 | Pletcher |
| 5,362,233 A | 11/1994 | Thompson |
| 5,380,197 A | 1/1995 | Hanson |
| 5,429,500 A | 7/1995 | Damon |
| 5,439,378 A | 8/1995 | Damon |
| 5,466,151 A | 11/1995 | Damon |
| 5,470,228 A | 11/1995 | Franseen et al. |
| 5,474,445 A | 12/1995 | Voudouris |
| 5,474,446 A | 12/1995 | Wildman et al. |
| 5,586,882 A | 12/1996 | Hanson |
| 5,613,850 A | 3/1997 | Wildman et al. |
| 5,630,715 A | 5/1997 | Voudouris |
| 5,630,716 A | 5/1997 | Hanson |
| 5,711,666 A * | 1/1998 | Hanson .......................... 433/11 |
| 5,762,492 A | 6/1998 | Kanomi et al. |
| 5,782,631 A | 7/1998 | Kesling et al. |
| 5,857,850 A | 1/1999 | Voudouris |
| 5,863,360 A | 1/1999 | Wood et al. |
| 5,885,074 A | 3/1999 | Hanson |
| 5,890,893 A | 4/1999 | Heiser |
| 5,906,486 A * | 5/1999 | Hanson .................. A61C 7/287 433/10 |
| 5,908,293 A | 6/1999 | Voudouris |
| 5,913,680 A | 6/1999 | Voudouris |
| 5,971,753 A | 10/1999 | Heiser |
| 6,071,118 A | 6/2000 | Damon |
| 6,071,119 A * | 6/2000 | Christoff ................ A61C 7/287 433/13 |
| 6,139,317 A | 10/2000 | Goldschmied |
| 6,168,428 B1 | 1/2001 | Voudouris |
| 6,193,508 B1 * | 2/2001 | Georgakis ...................... 433/11 |
| 6,247,923 B1 | 6/2001 | Vashi |
| 6,257,883 B1 | 7/2001 | Voudouris |
| 6,302,688 B1 | 10/2001 | Jordan et al. |
| 6,325,622 B1 | 12/2001 | Kelly et al. |
| 6,368,105 B1 | 4/2002 | Voudouris et al. |
| 6,375,458 B1 | 4/2002 | Moorleghem et al. |
| 6,394,798 B1 | 5/2002 | Huff et al. |
| 6,485,299 B1 | 11/2002 | Wildman |
| 6,506,049 B2 | 1/2003 | Hanson |
| 6,582,226 B2 | 6/2003 | Jordan et al. |
| 6,607,383 B2 | 8/2003 | Abels et al. |
| 6,655,957 B2 | 12/2003 | Abels et al. |
| 6,655,958 B2 | 12/2003 | Abels et al. |
| 6,659,766 B2 | 12/2003 | Abels et al. |
| 6,695,612 B2 | 2/2004 | Abels et al. |
| 6,726,474 B2 | 4/2004 | Spencer |
| 6,733,286 B2 | 5/2004 | Abels et al. |
| 6,776,613 B2 | 8/2004 | Orikasa |
| 6,843,651 B2 | 1/2005 | Orikasa |
| 6,902,396 B2 | 6/2005 | Kyritsis |
| 6,939,133 B2 | 9/2005 | Voudouris |
| 6,942,483 B2 | 9/2005 | Heiser |
| 6,960,080 B2 | 11/2005 | Abels et al. |
| 6,960,081 B2 | 11/2005 | Abels et al. |
| 7,001,179 B2 | 2/2006 | Devincenzo |
| 7,033,170 B2 | 4/2006 | Cordato |
| 7,063,531 B2 | 6/2006 | Maijer et al. |
| 7,094,052 B2 | 8/2006 | Abels et al. |
| 7,104,791 B2 | 9/2006 | Hanson |
| 7,134,873 B2 | 11/2006 | Miyaji et al. |
| 7,186,114 B2 | 3/2007 | Navarro et al. |
| 7,204,690 B2 | 4/2007 | Hanson |
| 7,214,057 B2 * | 5/2007 | Voudouris ............... A61C 7/287 433/11 |
| 7,234,935 B2 | 6/2007 | Abels et al. |
| 7,255,557 B2 | 8/2007 | Forster |
| 7,267,545 B2 | 9/2007 | Oda |
| 7,335,020 B2 | 2/2008 | Castner et al. |
| 7,336,020 B2 | 2/2008 | Ikeda et al. |
| 7,396,230 B2 | 7/2008 | Abels et al. |
| 7,416,408 B2 | 8/2008 | Farzin-Nia et al. |
| 7,419,375 B2 | 9/2008 | Farzin-Nia et al. |
| 7,442,039 B2 | 10/2008 | Opin et al. |
| 7,581,950 B1 | 9/2009 | Kesling |
| 7,585,171 B2 | 9/2009 | Hagelganz et al. |
| 7,621,743 B2 | 11/2009 | Bathen et al. |
| 7,704,072 B2 | 4/2010 | Damon |
| 7,717,706 B2 | 5/2010 | Forster |
| 8,414,292 B2 | 4/2013 | Lopes |
| 2001/0005574 A1 | 6/2001 | Manemann et al. |
| 2002/0006595 A1 | 1/2002 | Voudouris |
| 2002/0150857 A1 | 10/2002 | Orikasa et al. |
| 2003/0049582 A1 | 3/2003 | Abels et al. |
| 2004/0072117 A1 | 4/2004 | Farzin-Nia et al. |
| 2004/0072118 A1 | 4/2004 | Heiser et al. |
| 2004/0072119 A1 | 4/2004 | Voudouris |
| 2005/0239012 A1 | 10/2005 | Bathen et al. |
| 2006/0051721 A1 | 3/2006 | Carriere Lluch |
| 2006/0110699 A1 | 5/2006 | Forster |
| 2006/0154196 A1 | 7/2006 | Oda |
| 2006/0177790 A1 | 8/2006 | Farzin-Nia et al. |
| 2006/0228664 A1 * | 10/2006 | Castner et al. .................. 433/11 |
| 2006/0257810 A1 | 11/2006 | Maijer et al. |
| 2006/0269889 A1 | 11/2006 | Voudouris |
| 2006/0269895 A1 | 11/2006 | Voudouris |
| 2007/0082315 A1 | 4/2007 | Sabater |
| 2007/0160949 A1 | 7/2007 | Voudouris |
| 2007/0166658 A1 | 7/2007 | Voudouris |
| 2007/0178422 A1 | 8/2007 | Voudouris |
| 2007/0224569 A1 | 9/2007 | Oda |
| 2007/0243497 A1 | 10/2007 | Voudouris |
| 2007/0259301 A1 | 11/2007 | Hagelganz et al. |
| 2007/0269763 A1 | 11/2007 | Schendell-Groling |
| 2007/0281269 A1 | 12/2007 | Forster |
| 2008/0113311 A1 | 5/2008 | Forster |
| 2008/0248440 A1 | 10/2008 | Wool |
| 2009/0004617 A1 | 1/2009 | Oda et al. |
| 2009/0004618 A1 | 1/2009 | Oda et al. |
| 2009/0004619 A1 * | 1/2009 | Oda et al. ......................... 433/24 |
| 2009/0061376 A1 | 3/2009 | Wool |
| 2009/0075227 A1 | 3/2009 | Opin et al. |
| 2009/0136890 A1 | 5/2009 | Kang et al. |
| 2009/0155734 A1 | 6/2009 | Damon |
| 2009/0170049 A1 | 7/2009 | Heiser |
| 2009/0325120 A1 | 12/2009 | Lewis et al. |
| 2010/0000069 A1 | 1/2010 | Voudouris |
| 2010/0062387 A1 | 3/2010 | Hilliard |
| 2010/0112508 A1 * | 5/2010 | Lopes .............................. 433/10 |
| 2010/0261131 A1 | 10/2010 | Ruiz-Vela et al. |
| 2011/0076633 A1 | 3/2011 | Bryant et al. |

FOREIGN PATENT DOCUMENTS

| | | | |
|---|---|---|---|
| JP | S54127187 A | 10/1979 | |
| JP | H08168497 A | 7/1996 | |
| JP | 2002532188 A | 10/2002 | |
| JP | 2007319693 A | 12/2007 | |
| JP | 2009153978 A | 7/2009 | |
| WO | WO2008/114297 A1 * | 9/2008 | .............. A61C 7/28 |
| WO | WO 2008114297 A1 * | 9/2008 | |
| WO | 2009057937 A2 | 5/2009 | |

OTHER PUBLICATIONS

European Patent Office, partial European Search Report issued in Application No. 11179834.4 dated Jul. 27, 2015.

Japan Patent Office, Official Action issued in Japanese Patent Application No. 2011-191536 dated Dec. 4, 2015.

Chinese Patent Office, Office Action in CN 201110319320.X dated Apr. 28, 2015.

* cited by examiner

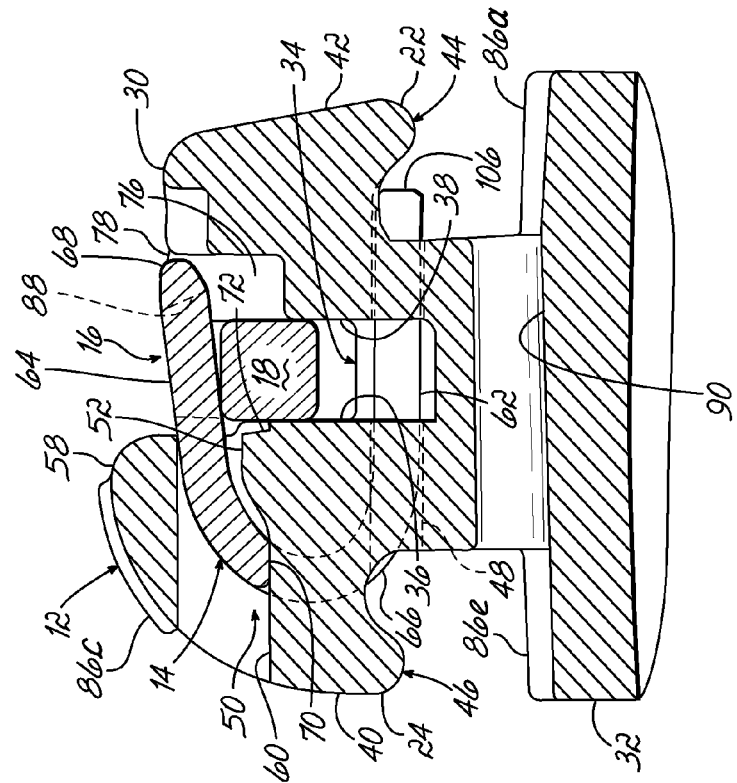
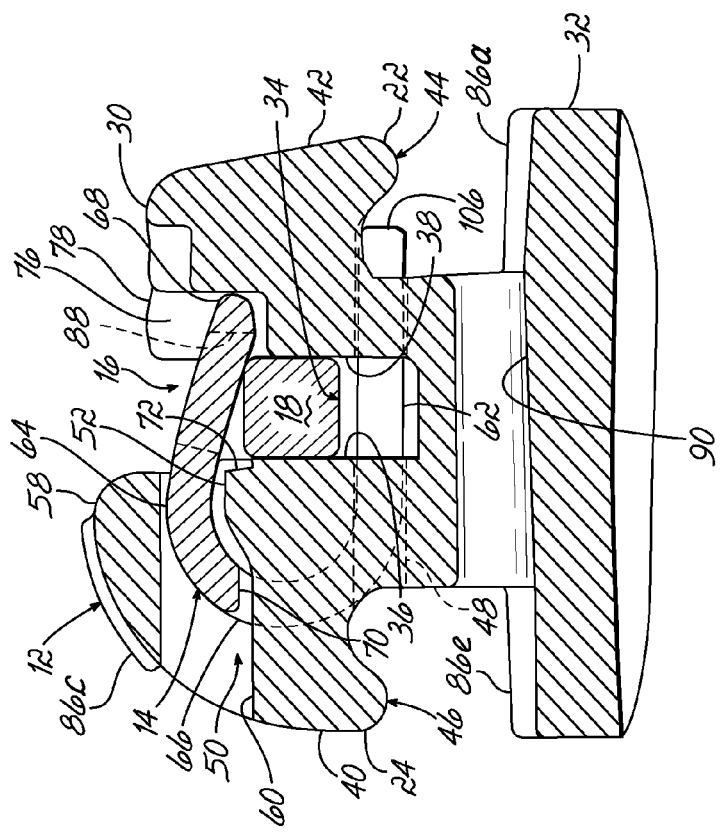

SELF-LIGATING ORTHODONTIC BRACKET AND METHOD OF MAKING SAME

CROSS REFERENCE TO RELATED CASES

This application claims priority to U.S. Provisional Patent Application Ser. No. 61/380,046 filed Sep. 3, 2010, the disclosure of which is incorporated by reference herein in its entirety.

TECHNICAL FIELD

The invention relates generally to orthodontic brackets and, more particularly, to self-ligating orthodontic brackets having movable closure members.

BACKGROUND

Orthodontic brackets represent a principal component of all corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that coerce the teeth to move into correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable portion or member, such as a latch or slide, for retaining the archwire within the bracket slot.

While self-ligating brackets have been generally successful, manufacturers of such brackets continually strive to improve the aesthetics associated with self-ligating brackets, the use and functionality of self-ligating brackets, and the costs and manufacturability of self-ligating brackets.

SUMMARY OF THE INVENTION

In one aspect, an orthodontic bracket for coupling an archwire with a tooth is provided and comprises a bracket body configured to be mounted to the tooth. An archwire slot is adapted to receive the archwire therein. A clip slot extends through the bracket body transversely to the archwire slot. A first body portion opposes a second body portion, which are separated from one another by the archwire slot. One of the first and second body portions includes a support surface that is open to the archwire slot.

A resilient ligating clip is slidably engageable with the support surface and the clip slot. The resilient ligating clip comprises a first and second clip portions that each extend generally in the same direction from a third clip portion and may form a generally U-shaped clip. The clip is movable relative to the bracket body between an opened position in which the archwire is insertable into the archwire slot and a closed position in which the first clip portion opposes the base surface and the third clip portion is adjacent the support surface. The clip is configured to flex and contact the bracket body on the body portion that includes the support surface when the first clip portion is deflected away from the base surface.

The bracket body may include various structures that contact the clip when the first clip portion deflects, generally as a result of an archwire pulling on the clip. Exemplary structures may include a mesial-distal bridge that at least partially covers the support surface. The first clip portion may be configured to contact the mesial-distal bridge when the first clip portion is deflected away from the base surface. Additional deflection of the first clip portion away from the base surface may be resisted by the flexing of the clip.

Other exemplary structures may include a clip stop surface that extends from one body portion, such as, the body portion including the support surface. In this embodiment, one of the first clip portion and the third clip portion may further include a shoulder configured to be in near-contact relation with the clip stop surface when the resilient ligating clip is in the closed position. The shoulder may be configured to contact the clip stop surface when the first clip portion is deflected away from the base surface. These and other structures may provide contact between the clip and the bracket body when the clip flexes in a direction opposite to deflection of the first clip portion away from the base surface. For example, when the first clip portion is deflected labially, the clip or a portion thereof may flex or move lingually to contact the bracket body by which the labial deflection of the first clip portion may be further restricted or stopped altogether.

In one embodiment, the bracket body includes a mesial-distal bridge that at least partially covers the support surface and a clip stop extending from at or near the support surface. The first clip portion is configured to contact the mesial-distal bridge and forms a fulcrum or contact location between the first clip portion and the mesial-distal bridge. When the first clip portion is further deflected away from the base surface, the shoulder flexes or moves in a direction opposite to deflection of the first clip portion to contact the clip stop surface. For example, if the first clip portion is deflected labially, the shoulder may move lingually or toward the tooth surface to contact the clip stop. As a result, two contact locations may be made between the bracket body and the clip to reduce or to stop further labial deflection of the clip to retain the archwire in the archwire slot. It will be appreciated that contact between the bracket body and the clip may occur in the reverse order from that described above. For example, the shoulder may initially contact the clip stop followed by contact between the clip and the mesial-distal bridge.

In one embodiment, the first clip portion includes a free end portion and the bracket body is configured to limit deflection of the first clip portion away from the base surface without contacting the free end portion.

In one embodiment, the orthodontic bracket includes a securing mechanism that is configured to secure the resilient ligating clip in at least the closed position. The securing mechanism includes a locking member in one of the bracket body and the second clip portion and a receiving member in the other of the bracket body and the second clip portion. The locking member and receiving member engage one another when the resilient ligating clip moves toward the opened position from the closed position. Accordingly, the securing mechanism may retain the clip in the closed position during treatment.

The locking and receiving member may have various forms and include various structures. In one embodiment, the locking member flexes in the plane of the second clip portion when the resilient ligating clip is moved from the opened position to the closed position. In one embodiment, the locking member has a leading surface that is configured to contact the bracket body during movement of the resilient ligating clip from the opened position to the closed position to cause the locking member to deflect.

In one aspect, a method of manufacturing a shaped unsintered body for use in manufacturing an orthodontic bracket is provided. The method may include various process steps including providing an unsintered body or green body that includes a plurality of sinterable particles and a binder. The unsintered body may approximate the shape of a pad, for example, for use with the orthodontic bracket. The pad may be formed integrally with a bracket body or separately therefrom and then later attached to a bracket body. A portion of the sinterable particles may be removed from the pad using a stream of energy, such as a laser beam, to yield a plurality of posts. The posts may be then deformed to yield an undercut on one or more of the deformed posts. The undercuts may improve bonding between the pad and the tooth surface. Deforming the posts may be achieved via a variety of processing techniques. In one embodiment, deforming the posts includes reducing the height of the posts or compressing the posts axially. In addition, removing a portion of the sinterable particles may additionally yield microscopic features. Removing a portion of the sinterable particles may additionally yield a least one peg that may be many times larger than any single one of the posts.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIG. 6A is a cross-sectional view of the orthodontic bracket shown in FIG. 2 taken along section line 6-6 with the ligating clip in an unloaded condition;

FIG. 6B is a cross-sectional view of the orthodontic bracket shown in FIG. 2 taken along section line 6-6 with the ligating clip in a loaded condition;

DETAILED DESCRIPTION

Figure 1:
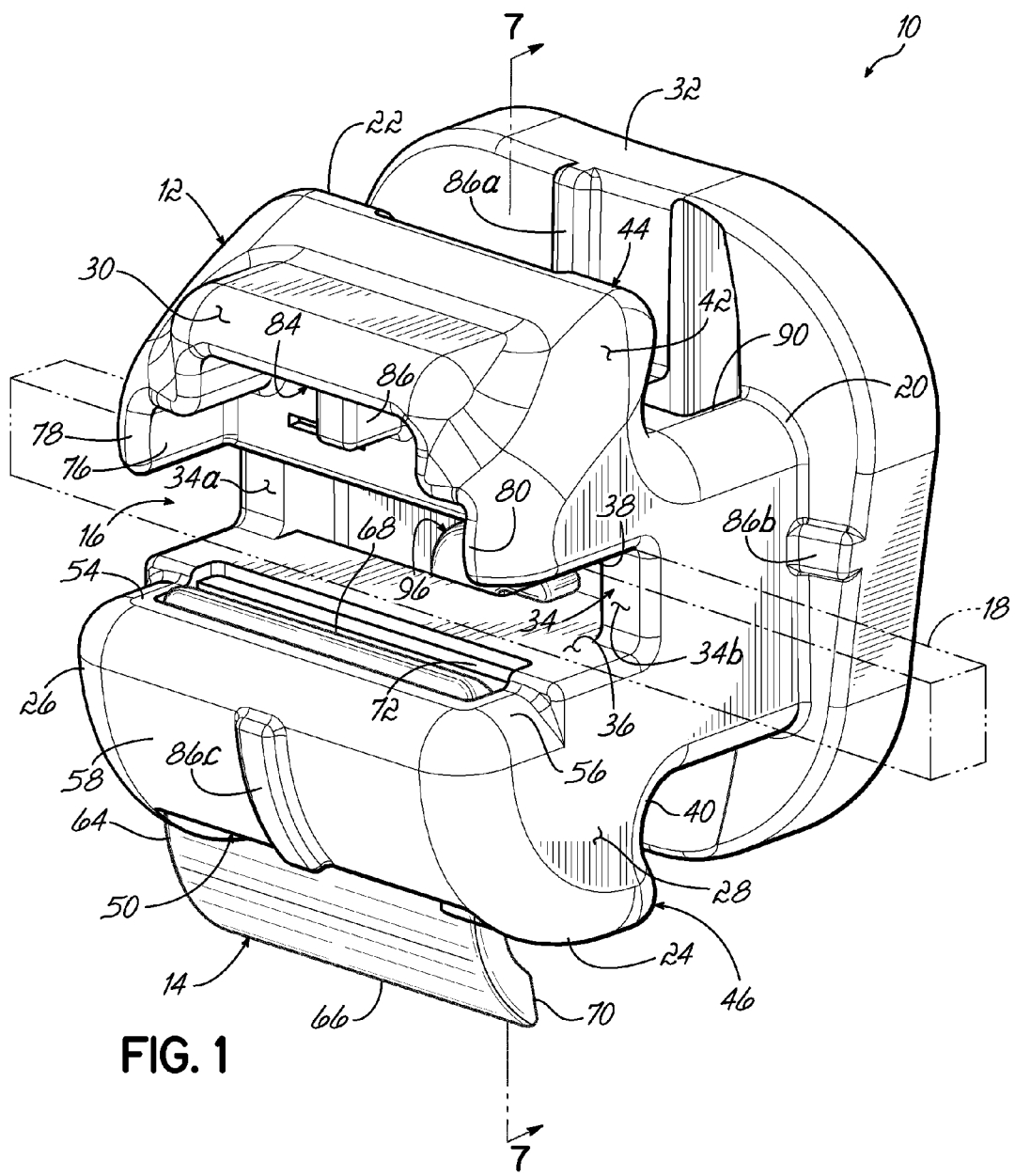
FIG. 1 is a perspective view of a self-ligating orthodontic bracket in accordance with one embodiment of the invention, a resilient ligating clip shown in an opened position.
Figure 2:
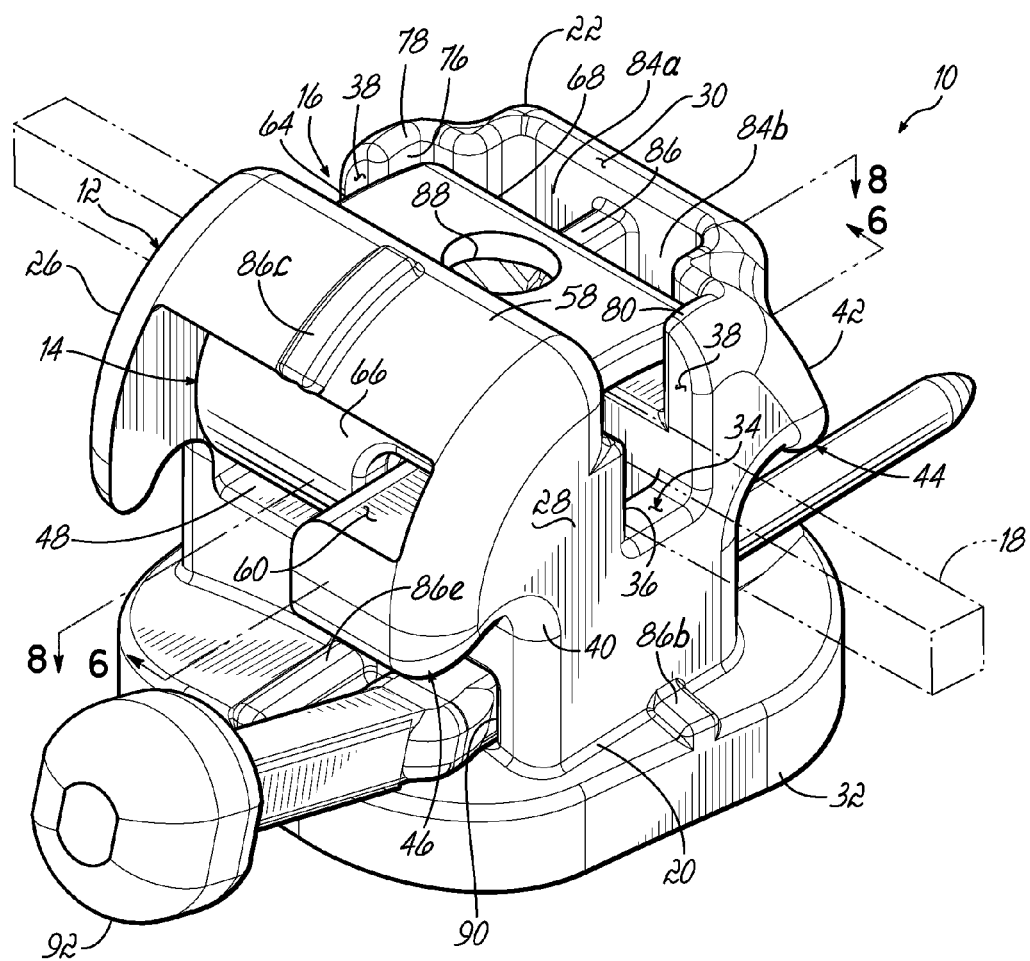
FIG. 2 is a perspective view of the self-ligating orthodontic bracket shown in FIG. 1 with the ligating clip shown in a closed position.

Referring now to the drawings and to FIGS. 1 and 2 in particular, an orthodontic bracket 10 includes a bracket body 12 and a movable closure member coupled to the bracket body 12. In one embodiment, the movable closure member may include a resilient ligating clip 14 that slidably engages the bracket body 12. The bracket body 12 and ligating clip 14 collectively form the orthodontic bracket 10 for use in corrective orthodontic treatments. To that end, the bracket body 12 includes an archwire slot 16 formed therein that is adapted to receive an archwire 18 (shown in phantom) for applying corrective forces to the teeth. The ligating clip 14 is movable between an opened position (FIG. 1) in which the archwire 18 is insertable into the archwire slot 16 and a closed position (FIG. 2) in which the ligating clip 14 retains the archwire 18 within the archwire slot 16. As is set forth in detail below, the ligating clip 14 may be securable to the bracket body 12 in the opened position and/or the closed position.

With continued reference to FIGS. 1 and 2, the bracket 10 inhibits inadvertent removal of the archwire 18 therefrom. However, according to embodiments of the invention, the archwire 18 may move within the archwire slot 16, may contact the clip 14, and may cause a portion of the clip 14 to move or elastically deflect from a relaxed, undeflected state. By way of example, during the early stages of treatment, a clinician may use an archwire that does not substantially fill the archwire slot 16. The archwire 18 may, therefore, not be fully seated in the archwire slot 16 during treatment. That is, there may be space between the archwire 18 and two or more opposing surfaces of the archwire slot 16 and/or between the archwire 18 and the clip 14. This is often referred to as "passive ligation." As a result, the archwire 18 may slide or move relative to the bracket 10 in the mesial and distal directions, move in labial and lingual directions, and/or in the occlusal and gingival directions during treatment. Considerable movement between the archwire 18 and the bracket 10 is possible. It will be appreciated that a relatively small archwire, which may be round in cross section, may be used to facilitate quicker leveling and aligning of the teeth during an initial stage of treatment.

During a later stage of treatment, it may be desirable to more precisely control the orientation of one or more of the teeth. In this regard, the archwire 18 may be forcibly held or fully seated in contact with the archwire slot 16 by the clip 14 and/or optional ligatures to provide control of rotation and torque on the particular tooth. This is often referred to as "active ligation." The clinician may use a relatively large archwire, which may be rectangular as opposed to round, to substantially fill the space within the archwire slot 16. The larger archwire may then contact both the slot 16 and the clip 14 at the same time to enhance the clinician's control of rotation of and torque on the tooth.

To that end, the orthodontic bracket 10, unless otherwise indicated, is described herein using a reference frame attached to a labial surface of a tooth on the lower jaw. Consequently, terms such as labial, lingual, mesial, distal, occlusal, and gingival used to describe bracket 10 are relative to the chosen reference frame. The embodiments of the invention, however, are not limited to the chosen reference frame and descriptive terms, as the orthodontic bracket 10 may be used on other teeth and in other orientations within the oral cavity. For example, the bracket 10 may also be coupled to the labial surface of a tooth on the maxilla or coupled to the lingual surface of the tooth and be within the scope of the invention. Those of ordinary skill in the art will recognize that the descriptive terms used herein may not directly apply when there is a change in reference frame. Nevertheless, embodiments of the invention are intended to be independent of location and orientation within the oral cavity and the relative terms used to describe embodiments of the orthodontic bracket are to merely provide a clear description of the embodiments in the drawings. As such, the relative terms labial, lingual, mesial, distal, occlusal, and gingival are in no way limiting embodiments of the invention to a particular location or orientation.

When mounted to the labial surface of a tooth carried on the patient's lower jaw, the bracket body 12 has a lingual side 20, an occlusal side 22, a gingival side 24, a mesial side 26, a distal side 28, and a labial side 30. The lingual side 20 of the bracket body 12 is configured to be secured to the tooth in any conventional manner, such as, by an appropriate orthodontic cement or adhesive or by a band around an adjacent tooth. The lingual side 20 may be provided with a pad 32 defining a bonding base that is secured to the surface of the tooth. The pad 32 may be coupled to the bracket body 12 as a separate piece or element, or alternatively, the pad 32 may be integrally formed with the bracket body 12.

During ligation, whether active or passive, where it is desired that the bracket 10 move relative to the archwire 18, the archwire 18 may forcibly contact or pull against the clip 14 to move the tooth in that direction. The clip 14 may deflect or elastically bend in the labial direction when subjected to these loads. In one embodiment, the amount that the clip 14 deflects is limited by the stiffness of the clip 14 and by contact points between the clip 14 and the bracket body 12, each of which is described in more detail below. In sum, the bracket body 12 captures the clip 14 in such a manner that limits how much the clip 14 deflects. The load on the clip 14 is at least partially transferred to the bracket body 12 by specific contact points between the two. According to embodiments of the present invention, the amount that the clip 14 deflects is insufficient, absent a catastrophic failure of the clip 14 or of the bracket body 12, to release the archwire 18 from the archwire slot 16. In other words, at the maximum deflection, the clip 14 retains the archwire 18 in the archwire slot 16.

In view of the above, the bracket body 12 more specifically includes a base surface 34 and a pair of opposed slot surfaces 36, 38 projecting labially from the base surface 34 that collectively define the archwire slot 16 extending in a mesial-distal direction from mesial side 26 to distal side 28. In one embodiment, the slot surfaces 36, 38 and base surface 34 are substantially encapsulated or embedded within the material of the bracket body 12. However, it will be appreciated that one or more of the slot surfaces 34, 36, and 38 may be defined by an insert (not shown) or liner (not shown) to enhance the wear characteristics of the archwire slot 16 or for other reasons. The archwire slot 16 of the bracket body 12 may be designed to receive the orthodontic archwire 18 in any suitable manner. The clip 14 is positioned to close the archwire slot 16 opposite the base surface 34 to prevent inadvertent removal of the archwire 18 therefrom during treatment. The clip 14 may, however, be intentionally moved to allow one archwire within the slot 16 to be removed and another archwire to be inserted as treatment progresses. It will be appreciated that the bracket body 12 may be made of a metal or metal alloy or ceramic material by any one of a number of commercially available processes including, and by way of example and not limitation, metal injection molding (MIM), ceramic injection molding (CIM), other injection molding, or casting technique.

Referring now to FIGS. 1-4B in one exemplary embodiment, the bracket body 12 includes a gingival body portion 40 and an occlusal body portion 42. As shown, the body portions 40, 42 are separated by the archwire slot 16 and may define one or more of the slot surfaces 34, 36, 38, respectively, as described above. In the exemplary embodiment depicted, the body portions 40, 42 collectively include a lingual slot 48 (best shown in FIGS. 4A and 4B) that extends therethrough and that opens to each of the occlusal and gingival sides 22, 24 of the bracket body 12. The lingual slot 48 is, in part, configured to guide the clip 14 during movement between the closed and opened positions.

In the exemplary embodiment shown, the lingual slot 48 is positioned lingually of the base surface 34 of the archwire slot 16 and is open to the occlusal and gingival sides 22, 24. However, it will be appreciated that the labial-lingual location of the lingual slot 48 is not so limited. In the embodiment shown, the lingual position of the slot 48 is located such that it intersects or opens to the archwire slot 16, shown best in FIG. 3. In this configuration, the base surface 34 may be divided into mesial and distal base surface portions 34a, 34b. The clip 14 may therefore be positioned proximate the base surface portions 34a, 34b and may form a portion of the base surface 34 when the clip 14 is in the closed position. While shown in this configuration, the lingual slot 48 is not, however, limited to intersecting or opening to the archwire slot 16 as the slot 48 may be defined on four sides by the bracket body 12 without opening to the archwire slot 16. In addition, the labial-lingual position of the slot 48 may vary depending upon the location for use of the bracket 10 within the mouth. By way of example, the lingual slot 48 may be at least partly defined by the pad 32 such that one or more sides of the slot 48 are defined by the pad 32. The slot 48 may further extend at an angle relative to the pad 32 causing the slot 48 to intersect the pad 32 adjacent one of the occlusal or gingival sides 22, 24. Thus, a portion of the slot 48 may be formed in the pad 32. This orientation may allow sufficient room between the bracket 10 and surrounding tissue in which to move the ligating clip 14 in a gingival direction to permit access to the archwire slot 16.

Figure 4A:
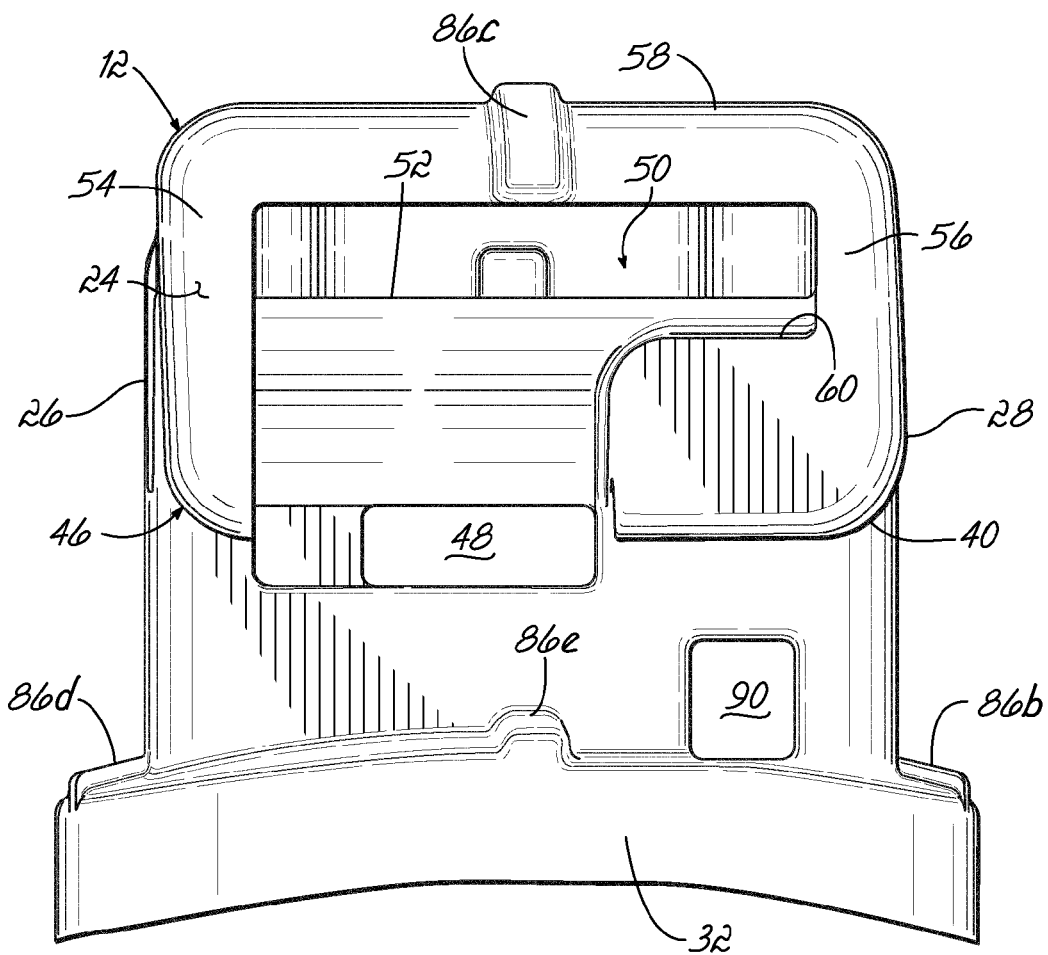
FIG. 4A is a side elevation view of the bracket body shown in FIG. 3.
Figure 4B:
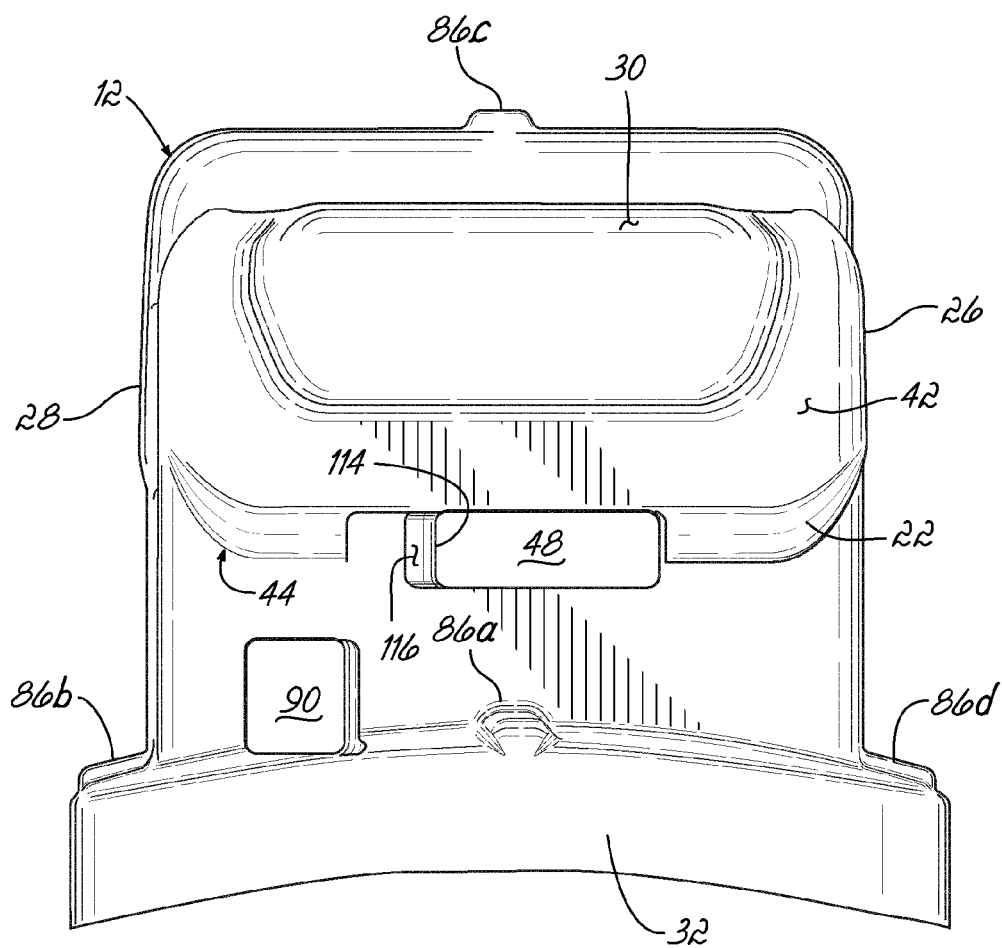
FIG. 4B is another side elevation view of the bracket body shown in FIG. 3 in the opposite direction of that shown in FIG. 4A.

Further, with reference to FIGS. 4A and 4B, while the slot 48 is shown opening to both occlusal and gingival sides 22, 24, it will be appreciated that the lingual slot 48 may extend only partially through the body 12 while sufficiently guiding the clip 14 between the opened and closed positions. In this case, the lingual slot 48 may not extend through the occlusal body portion 42 to open to the occlusal side 22. Rather, the slot 48 may have a closed occlusal end, i.e., be a blind bore, or be partially closed, as shown. The bracket body 12 may define the sides of the lingual slot 48 such that it is slightly larger than the corresponding cross section of the clip 14. The clearance between the slot 48 and the clip 14 may be designed to prevent the clip 14 from binding in the slot 48 during use, such as, during opening and closing movements.

Figure 3:
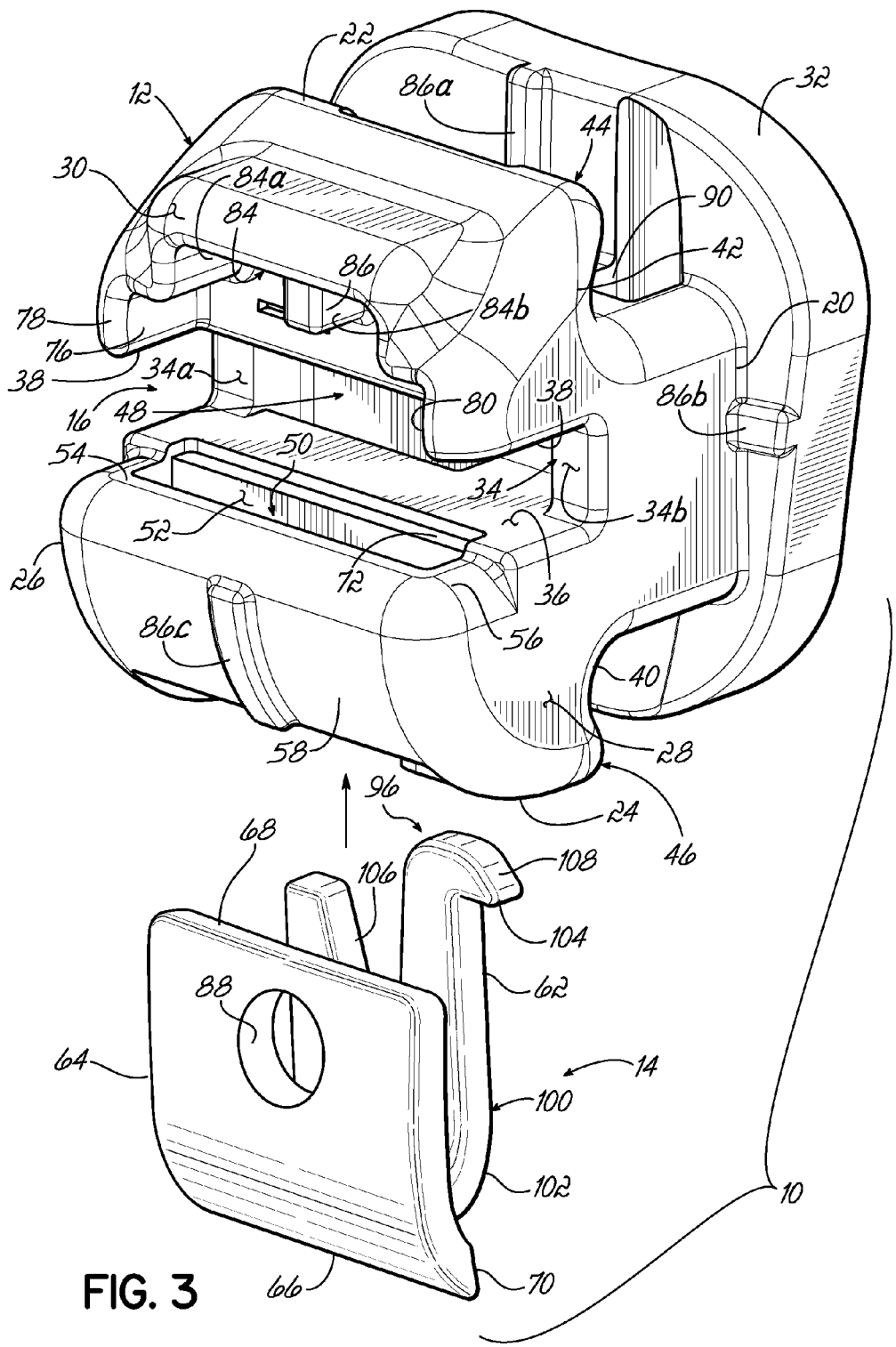
FIG. 3 is a perspective view of the self-ligating orthodontic bracket shown in FIG. 1 with the ligating clip removed from the bracket body.

With reference to FIGS. 1, 3, and 4A, the gingival body portion 40 further includes a labial slot 50. The labial slot 50 is positioned labially of the lingual slot 48, described above, and opens to the archwire slot 16, shown in FIG. 3. The lingual and labial slots 48, 50 may individually or collectively guide the clip 14 during movement thereof between the opened and closed positions. The labial slot 50 is defined in part by a support surface 52 that extends in a generally gingival-occlusal direction, faces generally away from the tooth surface, and has a width near that of the archwire slot 16. The support surface 52 may or may not include a planar surface. For example, the support surface 52 may be a convexly-curved surface in the gingival direction around a mesial-distal axis to accommodate any similar curvature of the clip 14. The support surface 52 may open to the archwire slot 16 at an occlusal-most edge thereof.

As shown in FIGS. 3 and 4A, a pair of opposed guides 54, 56 are carried by support surface 52 and are positioned on respective mesial and distal sides 26, 28 of bracket body 12. A mesial-distal bridge 58 extends from mesial guide 54 to the distal guide 56 and projects over at least a portion of the support surface 52, such as, the labial-facing surface portion thereof. In one embodiment, the mesial-distal bridge 58, guides 54 and 56, and support surface 52 collectively define the labial slot 50, and together with the lingual slot 48, support and guide the ligating clip 14 within bracket body 12. As set forth above, the bracket body 12 limits the outward deflection of the clip 14. To this end, the mesial-distal bridge 58 cooperates with the clip 14 to limit labial movement of the clip 14 to resist inadvertent release of the archwire 18 from the archwire slot 16. While the bridge 56 is shown spanning between guides 54, 56, it will be appreciated that embodiments of the invention are not limited to bridges that fully span between guides, as a bridge may span only a partial distance and retain the function of the bridge 56 as set forth herein.

Further in this respect, in the exemplary embodiment shown in FIGS. 2 and 4A, the bracket body 12 may be configured with a clip stop 60 that extends in a gingival direction from the support surface 52. As shown best in FIG. 4A, the clip stop 60 may extend in the mesial direction from the distal guide 56 at a labial-lingual level that is at or near the level of the labial-facing portion of the support surface 52. As is described in more detail below, the clip 14 may come into contact with the clip stop 60 when the clip 14 deflects outwardly. It will be appreciated that the clip stop 60 may extend from the mesial guide 54 and that the relative height of the clip stop 60 as compared to the support surface 52 may be preselected to contact the clip 14 after a predetermined amount of deflection of the clip 14, as set out below.

Figure 5A:
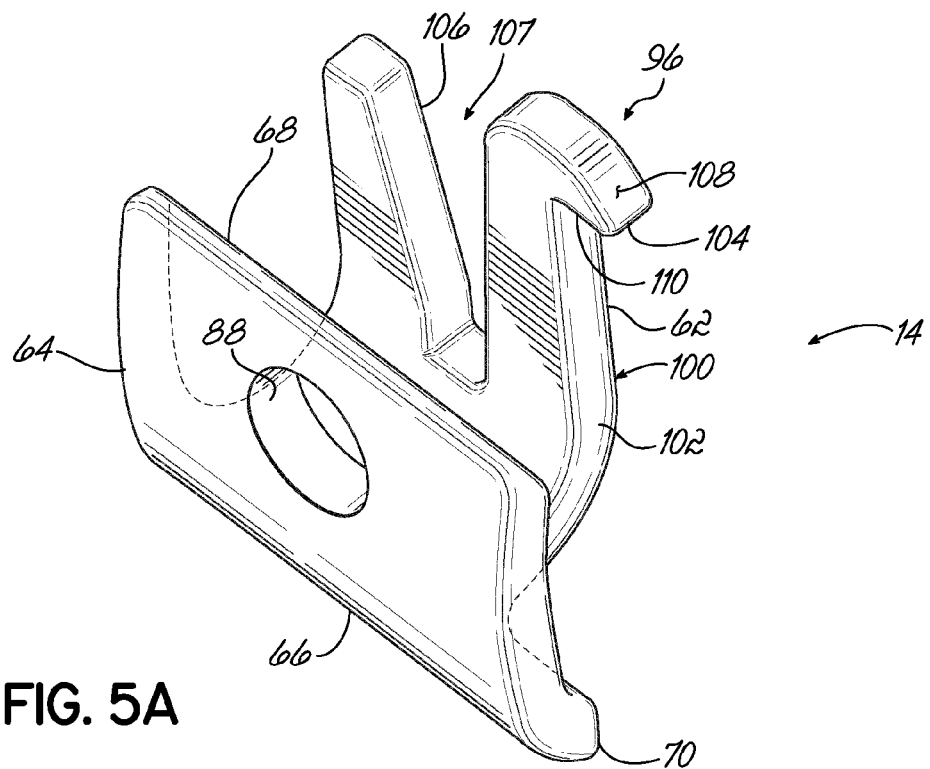
FIG. 5A is a perspective view of the ligating clip shown in FIG. 3.
Figure 5B:
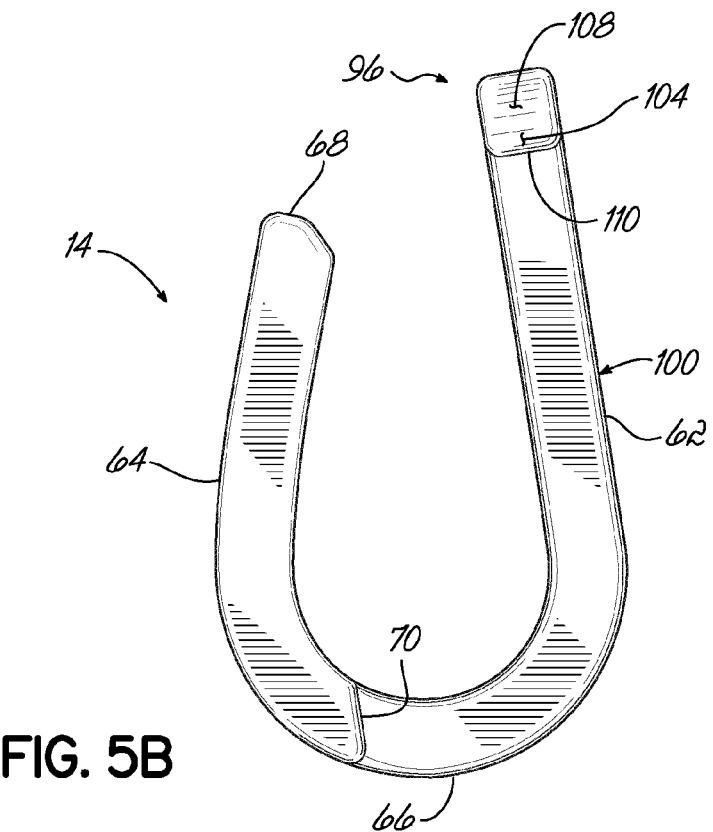
FIG. 5B is a side elevation view of the ligating clip shown in FIG. 3.

With reference to an exemplary embodiment of the clip 14 as shown in FIGS. 3 and 5A-5C, the ligating clip 14 has a lingual clip portion 62 and a labial clip portion 64 extending generally in the same direction from a gingival clip portion 66. The labial clip portion 64 terminating in free end or an occlusal-most end 68. In the exemplary embodiment shown, the clip 14 has a generally U-shaped configuration (FIG. 5B). It will be appreciated, however, that the clip 14 may have other configurations or shapes that are sufficient to retain the archwire 18 within the archwire slot 16; the configuration of the clip 14 is not limited to generally U-shaped configurations. As introduced above, the bracket body 12 and the ligating clip 14 may be configured to contact one another to transfer load from the ligating clip 14 to the bracket body 12 to reduce the possibility of inadvertent release of the archwire 18 from the archwire slot 16.

In this respect and as depicted in the exemplary embodiment of the ligating clip 14 shown in FIGS. 3 and 5A, the periphery of the clip 14 defines a shoulder 70 in the labial clip portion 64. As such, the mesial-distal width of the labial clip portion 64 in this embodiment may be greater than the mesial-distal width of the lingual clip portion 62 with the shoulder 70 accounting for most of the difference in width, shown best in FIG. 5C. The center line of the lingual clip portion 64 may be offset from the center line of the clip 14. When inserted into the bracket body 12, as described below, the shoulder 70 may reside in near-contact relation with the bracket body 12, specifically proximate the clip stop 60 though no contact may be initially made when the clip 60 is moved to the closed position. While the shoulder 70 is described as being formed in the labial clip portion 64, it will be appreciated that the shoulder 70 may be formed in the gingival clip portion 66 and function in a similar manner as that described below.

In one embodiment, the ligating clip 14 is made of a superelastic alloy. As is known in the art, superelastic alloys may be deformed to very high strains, for example, up to around 10%, without permanent deformation. Advantageously, a clip made of a superelastic alloy may be used where a stainless steel clip would permanently deform or yield and thus eventually fail. Suitable superelastic alloys include nickel-titanium alloy, which may be further alloyed with small additions of other metals, such as, copper and chromium. For example, one suitable chemical composition is about 49.1 wt. % nickel (Ni), about 44.6 wt. % titanium (Ti), about 5.9 wt. % copper (Cu), and from about 0.2 to about 0.3 wt. % chromium (Cr), as well as other minor impurities.

Furthermore, in one embodiment, the stiffness of a superelastic alloy clip may vary along the length of the clip 14. As is known, stiffness variation may be produced by different levels of cold working of the metal of the clip 14 with or without heat treatment. By way of example, the gingival clip portion 66 may be of the greatest stiffness with the lingual and labial clip portions 62, 64 being of approximately equal stiffness. However, it will be appreciated that other stiffness variation or constant stiffness along the clip 14 may suffice. In one embodiment, the combination of the stiffness of the clip 14 and the load carrying contact locations with the bracket body 12 may cooperate to restrict release of the archwire 18 from the bracket 10 without unduly restricting movement of the archwire 18 in the bracket 10.

In FIG. 1, the clip 14 is in an opened position, where the labial clip portion 64 is sufficiently clear of the archwire slot 16 to allow the archwire 18 to be placed therein. In the opened position, the labial clip portion 64 may contact the support surface 52 proximate the archwire slot 16. The gingival clip portion 66 may then project from the gingival side 24 of the bracket body 12.

During treatment, once the archwire 18 is placed in the archwire slot 16, the clip 14 may be moved to the closed position, as is depicted in FIG. 2. To this end, the lingual and labial clip portions 62, 64 may be slid into their respective lingual and labial slots 48, 50 of the bracket body 12. The labial clip portion 64 covers the archwire slot 16 to oppose the base surface 34 sufficiently to retain the archwire 18 within the slot 16. When the clip 14 is moved to the closed position, the labial clip portion 64 is positioned into near-contact relation with the mesial-distal bridge 58, as depicted in FIGS. 2 and 6A. In other words, the clip 14 may not contact the bridge 58 when the clip 14 is in an unloaded or non-deflected state; there may be a gap between the clip 14 and the mesial-distal bridge 58 when the clip 14 is in an unloaded state (shown best in FIG. 6A). However, the clip 14 may be in a position to contact the bridge 58 should the labial clip portion 64 deflect or move labially (shown in FIG. 6B). When unloaded, the clip 14 may thus be moved gingivally and occlusally within the bracket body 12 without contacting the mesial-distal bridge 58 or clip stop 60. This may be, for example, during the initial closure of clip 14. The clip 14 may, however, slide on the support surface 52 and contact one or more surfaces of the lingual slot 48 during movement between the opened and closed positions. In this regard, the clip 14 may flex to enable its passage through the bracket body 12 during which passage the clip 14 may incidentally contact other surfaces of the bracket body 12.

The function of the clip 14 in conjunction with the bracket body 12 will now be described in more detail. As shown in FIGS. 6A and 6B, which depicts the clip 14 in the closed position, the labial clip portion 64 opposes the base surface 34, the gingival clip portion 66 may abut or be adjacent to the support surface 52, and the lingual clip portion 62 occupies the lingual slot 48. The remaining sides 36, 38 of the archwire slot 16 together with the labial clip portion 64 enclose the archwire 18 to capture it therein.

As introduced above, when the clip 14 is in the closed position to capture the archwire 18 therein, forces on the archwire 18 may cause it to push/pull against the labial clip portion 64. As shown in FIGS. 6A and 6B, when the archwire 18 applies a sufficient amount of force to the clip 14, the clip 14 will deflect. Where there initially was some clearance between the clip 14 and the bracket body 12 as shown in FIG. 6A, forces on the clip 14 may cause sufficient deflection of the clip 14 such that it traverses the gap to come into contact with the mesial-distal bridge 58 as shown in FIG. 6B. Further labial movement of the archwire 18 in the archwire slot 16 may be stopped by this contact between the clip 14 and the bracket body 12. In this respect, the mesial-distal bridge 58 limits the magnitude of labial movement and labial deflection of the clip 14 and creates a load transfer contact point. It will be appreciated that contact between the clip 14 and the mesial-distal bridge 58 may be in addition to any contact between the lingual clip portion 62 and the bracket body 12 in the lingual slot 48 and/or contact between the gingival clip portion 66 and the bracket body 12.

Alternatively or in addition to the contact between the labial clip portion 64 and the bridge 58, as set out above, the labial clip portion 64 and/or the gingival clip portion 66 may contact the bracket body 12 at other locations to limit labial movement of the labial clip portion 64. For instance and with continued reference to FIG. 6A, in one embodiment, the shoulder 70 may be in a position to contact the clip stop 60 though a gap may initially separate the shoulder 70 from the clip stop 60. As such, although the shoulder 70 may not contact the clip stop 60 when the clip 14 is in a relaxed or unloaded state, deflection of the labial clip portion 64 may cause the shoulder 70 to move, flex, or deflect lingually to contact the clip stop 60, as shown in FIG. 6B. In other words, labial movement of the labial clip portion 64 may cause an opposite movement, i.e., lingual movement, of the shoulder 70. Sufficient lingual movement of the shoulder 70 creates a load transfer contact point with the clip stop 60.

The clip 14 may be configured to selectively contact the bracket body 12, for example, via the mesial-distal bridge 58 and/or clip stop 60, under predetermined loading conditions experienced by the clip 14 and thus transfer a portion of that load to the bracket body 12 under those load conditions.

In one embodiment, when the archwire 18 moves labially and causes a sufficient amount of deflection of the labial clip portion 64, the labial clip portion 64 moves labially to contact the mesial-distal bridge 58 and forms a fulcrum. In this regard, any additional labial movement of the labial clip portion 64 may be resisted by the flexing of the clip 14, for example, flexing of the gingival clip portion 66. That is, stiffness of the clip 14 may provide additional resistance to deflection after the labial clip portion 64 contacts the mesial-distal bridge 58. Under continued labial movement, if any, of the labial clip portion 64, the shoulder 70 moves lingually to contact the clip stop 60. Load transfer may occur between the clip 14 and the bracket body 12 at each of these locations, though in opposing directions, to thereby limit or arrest further movement of the labial clip portion 64. It will be appreciated that contact between the shoulder 70 and the clip stop 60 may be in addition to or an alternative to contact between the mesial-distal bridge 58 and the clip 14, described above. However, as is shown best in FIG. 6B, no portion of the bracket body 12 captures the occlusal-most end 68 of the labial clip portion 64 to limit outward movement thereof. Accordingly, in an exemplary embodiment of the present invention, the labial clip portion 64 only contacts the bracket body 12 gingivally of the archwire slot 16 when the archwire 18 causes the clip 14 to deflect or bend outward.

In addition, during treatment, it will be appreciated that the mesial-distal bridge 58 covers at least a portion of the labial clip portion 64. In this exemplary embodiment, the bridge 58 defines the labial-most surface of the gingival body portion 40. Referring to FIG. 2, during normal mastication, any passing buccal tissue, food, and/or other material may contact and slide across the bridge 58 without contacting at least the covered portions of the ligating clip 14. In this manner, the bridge 58 may reduce or eliminate cyclic, occlusal-gingival motion of the clip 14 due to contact with surrounding tissues or other matter.

Additionally, in one embodiment and with reference to FIGS. 1 and 3, rather than opening to the archwire slot 16, the support surface 52 intersects a bur channel 72. The bur channel 72 is a cutout or cavity formed into the gingival body portion 40 and may extend the full width of an apparent intersection of the support surface 52 with the slot surface 36. The bur channel 72 may be adapted to capture foreign material or abrasion debris pushed through the labial slot 50 by the occlusal-most end 68 of the labial clip portion 64, thereby reducing or limiting entry of the debris into the archwire slot 16. It will be appreciated that while the bur channel 72 is shown as extending the full length of the support surface 52, the bur channel 72 is not so limited. By way of example, it may extend along one or more sections or a partial length of the support surface 52 and may be additionally incorporated at other labial-most edges of the archwire slot 16, such as, the labial-most edge of the slot surface 38.

In addition, referring to FIGS. 1 and 3, in the exemplary embodiment shown, the occlusal body portion 42 includes a clip receptacle 76 that receives the occlusal-most end 68 of the labial clip portion 64 when the clip 14 is moved to the closed position. Accordingly, the occlusal-most end 68 extends occlusally past the slot surface 38. The clip receptacle 76 includes mesial and distal guides 78, 80 that may limit or stabilize the motion of the labial clip portion 64 if it is forced in either of those directions by the archwire 18.

With continued reference to FIGS. 1 and 3, the clip receptacle 76 opposes the support surface 52 across the archwire slot 16. Therefore, the ligating clip 14 passes through the labial slot 48 and into the clip receptacle 76 to close the archwire slot 16. As set forth above, the clip receptacle 76 is open to the labial side 30 of the bracket body 12. In the exemplary embodiment shown, the clip receptacle 76 does not limit labial movement of the labial clip portion 64. This is best illustrated in FIG. 6B, where it is shown that the occlusal-most end 68 of the labial clip portion 64 may deflect labially proximate or beyond the labial side 30 of the occlusal body portion 42. Moreover, embodiments of the present invention may include an occlusal body portion which does not capture or restrain labial movement of the occlusal-most end 68 of the labial clip portion 64. Rather, the labial movement of the labial clip portion 64 is restrained only through one or more contact points between non-free end portions of the clip 14 and the gingival body portion 40, as is further described herein.

In one embodiment shown in FIGS. 1 and 3, the occlusal body portion 42 further includes a tool receptacle 84 that is open to and is coplanar with a lingual surface of the clip receptacle 76, described above. The tool receptacle 84 is configured to receive a tool (not shown) used to open or force the clip 14 from the closed position. In this respect, the tool receptacle 84 may have a rectangular or other oblong shape with its longitudinal axis oriented generally in the mesial-distal direction. The clip 14 may be opened, as described in more detail below, by inserting a tool having a shape similar to that of the tool receptacle 84 therein and twisting the tool thereby leveraging one side of the tool with a peripheral wall of the tool receptacle 84 and the other side of the tool against the occlusal-most end 68 of the clip 14 to move the clip 14 in the gingival direction. Such tools and tool receptacles are disclosed in commonly owned U.S. Publication Nos. 2009/0004618 and 2009/0004617, the disclosures of which are incorporated by reference herein in their entireties.

Also shown in FIGS. 1, 2, and 3, the tool receptacle 84 may further include an internal rib 86 that divides the tool receptacle 84 into mesial and distal receptacles 84a, 84b, respectively. In this instance, a tool (not shown) having two prongs, one for each of the mesial and distal receptacles 84a, 84b, may be inserted into the tool receptacle 84 and a twisting motion, much like that described immediately above, moves the clip 14 toward the opened position.

Further and with reference to FIG. 1, the body portions 40, 42 may include opposing occlusal and gingival tie wings 44, 46, respectively, for receiving one or more ligatures (not shown), as is known in the art. Ligatures may be used in addition to or as an alternative to the clip 14 to secure the archwire 18 to the bracket 10. For example, where the clinician is unable to seat the archwire 18 within the slot 16 sufficiently to move the clip 14 to the closed position, it may be necessary to use a ligature to secure the bracket body 12, via the tie wings 44, 46, to the archwire 18 to move the tooth into a position where the archwire 18 may then be seated within the archwire slot 16. It will be appreciated that while tie wings 44, 46 and ligatures are described herein, embodiments of the present invention are not limited only to those brackets having tie wings.

In one embodiment and as shown in FIGS. 1, 4A, and 4B, the bracket 10 includes one or more alignment markers 86a, 86b, 86c, 86d, 86e that may comprise raised or recessed areas on the surface to create a visibly discernable feature on the bracket 10. The alignment markers 86a-86e may indicate the center line of the bracket 10 in each of the mesial and distal directions and gingival and occlusal directions to facilitate alignment of the bracket 10 on the tooth. To that end, the alignment markers 86a-86e may be positioned on visible portions of the bracket body 12. By way of example, as shown in FIG. 1, alignment markers may be positioned on visible portions of the pad 32; adjacent the mesial and distal sides 26, 28 of the bracket body 12; on visible surfaces of the pad 32 adjacent the occlusal and gingival sides 22, 24 of the bracket body 12; and/or on the labial side 30 of the bracket body 12.

Further in this respect and with reference to FIGS. 2 and 3, the clip 14 may include a hole or an aperture 88 in the labial clip portion 64. The clinician may use the aperture 88 with or without the alignment markers 86a-86e to position the bracket 10 on the tooth. In particular, the aperture 88 may aid alignment of the bracket 10 with the center of the tooth. And, together with the alignment markers 86a-86e, the aperture 88 may further enhance alignment of the bracket 10 on the tooth.

With reference to FIGS. 2, 4A, and 4B, in one embodiment, the bracket body 12 further includes a vertical or gingival-occlusal extending bore 90. Generally, the bore 90 is transverse to the archwire slot 16 and is configured to slidably receive an interchangeable auxiliary device 92 (shown in FIG. 2), such as a spring or hook, to aid in orthodontic treatment. By way of example, the cross-sectional shape of the bore 90 may be rectangular, however, it will be appreciated that the bore 90 may have other configurations. The bore 90 may open to both of the occlusal side 22 and the gingival side 24 of the bracket body 12 and be located mesially or distally of the lingual slot 48. In the embodiment shown, the bore 90 is located lingually of the archwire slot 16.

In addition, it will be appreciated that, depending on the position of the tooth onto which the bracket 10 is to be placed, the bore 90 may be formed by a portion of the pad 32. For example, the pad 32 may form the lingual side of the bore 90 or at least a portion thereof to orient any auxiliary device inserted therein in a particular manner. In this regard, although not shown, the bore 90 may extend between the occlusal and gingival sides 22, 24 of the bracket body 12 at an angle relative to the pad 32 such that one of the gingival or occlusal ends of the bore 90 is defined by a portion of the pad 32. Depending on the particular application, however, the bore 90 may be completely contained within the bracket body 12, as is described more fully below.

As introduced above, in one embodiment of the present invention, the clip 14 may be secured in the closed and/or opened positions. The clip 14 may then be prevented from separating from the bracket body 12 during use and/or during removal and installation of the archwire 18 from the archwire slot 16. As shown in FIGS. 7, 7A, 7B, 8, and 8A, in one embodiment, the orthodontic bracket 10 includes a securing mechanism 94 that secures the ligating clip 14 in at least the closed position. In the exemplary embodiment depicted, the securing mechanism 94 includes a locking member 96 that forms a portion of the lingual clip portion 62 and a receiving member 98 that is defined by the occlusal body portion 42. The locking member 96 cooperates with the receiving member 98 to secure the clip 14 in the closed position during treatment. Although this embodiment is described with the locking member 96 associated with the ligating clip 14 and the receiving member 98 associated with the bracket body 12, those of ordinary skill in the art will recognize that the invention is not so limited. For example, although not shown, the locking member 96 may be coupled to the bracket body 12 and the receiving member 98 may be formed in the ligating clip 14.

Figure 5C:
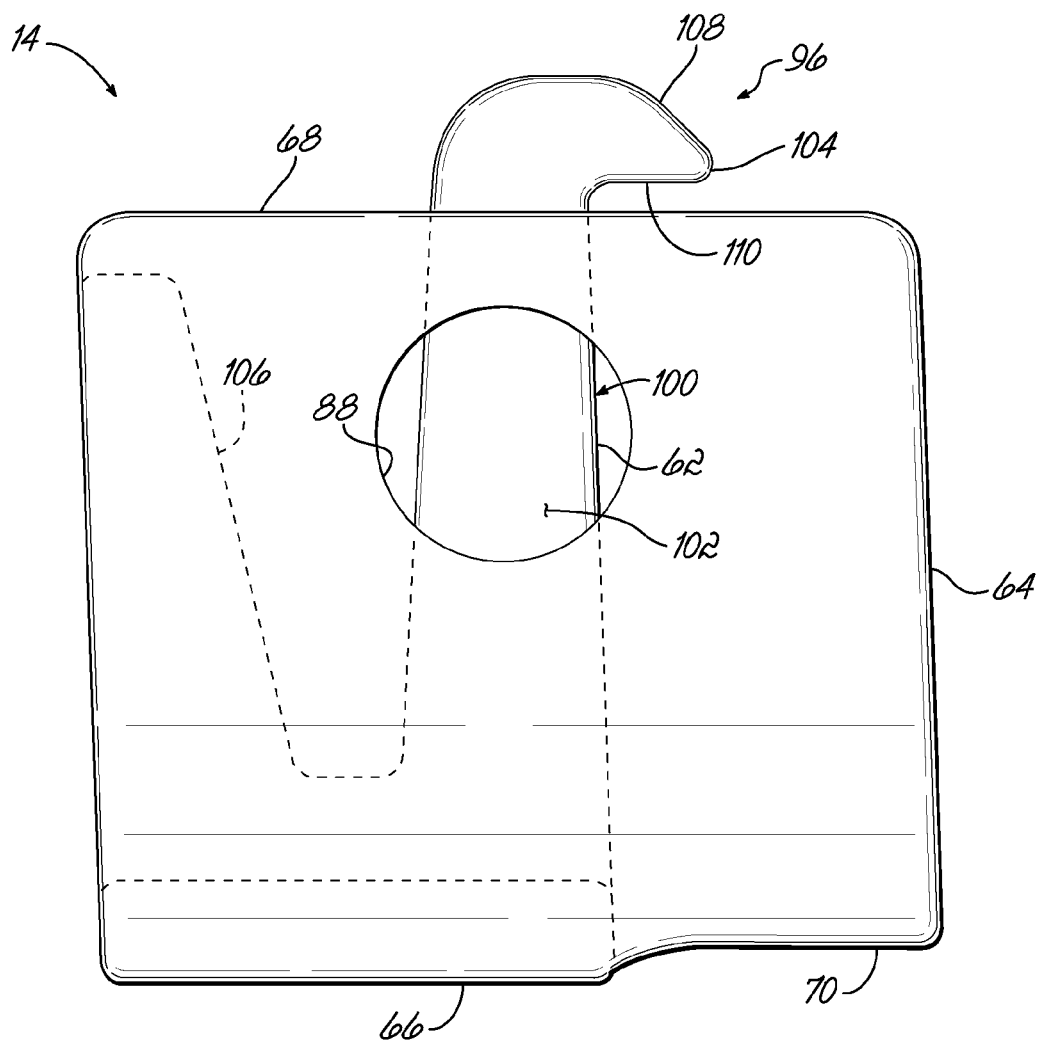
FIG. 5C is a plan view of the ligating clip shown in FIG. 3.

In one embodiment of the present invention and with reference to FIGS. 5A-5C, the locking member 96 forms at least a portion of the lingual clip portion 62 of the ligating clip 14. By way of example, the locking member 96 may include a hooked-shaped or L-shaped projection 100 and an alignment member 106. The L-shaped projection 100 and the alignment member 106 may visually form a bifurcated lingual clip portion 64. The L-shaped projection 100 and the alignment member 106 slidably engage the lingual slot 48 of the bracket body 12, shown best in FIGS. 7A-8. The L-shaped projection 100 has a first leg 102 and a second leg 104 projecting from the first leg 102 at a transverse angle relative thereto. Further, in one embodiment, both the first and second legs 102, 104 are coplanar with and separate from the alignment member 106 by a V-shaped cutout 107. It will be appreciated that the orientations of the first and second legs 102, 104 may differ from that shown. For example, the second leg 104 may project out of the plane of the lingual clip portion 62.

In the exemplary embodiment shown and with reference to FIG. 5C, the first leg 102 projects generally occlusally from the gingival clip portion 66. The second leg 104 extends generally perpendicular to the first leg 102. The tip of the second leg 104 defines a leading cam surface 108 that opposes a trailing abutment surface 110. As depicted in FIG. 7A, the leading cam surface 108 generally faces in the direction of the movement of the clip 14 toward the closed position and is described more fully below in conjunction with movement of the clip 14 from the opened to the closed position.

Figure 7:
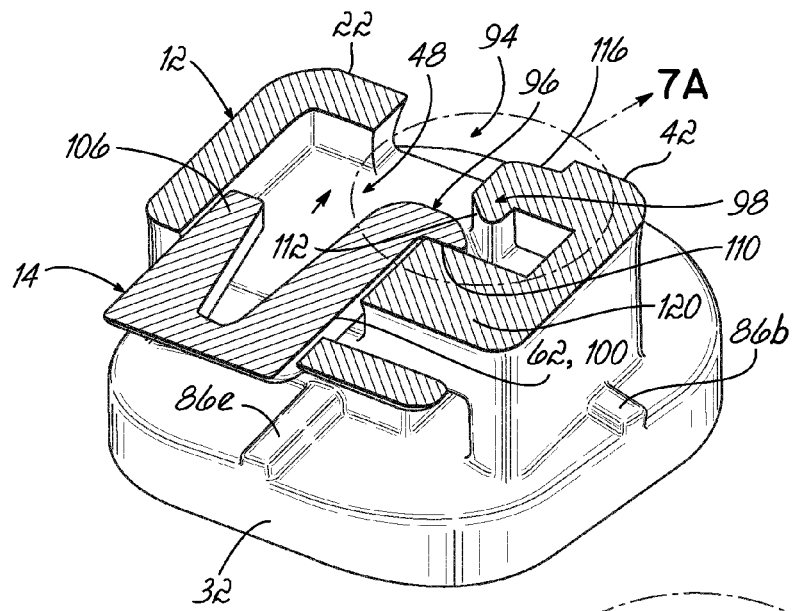
FIG. 7 is a cross-sectional perspective view of the self-ligating orthodontic bracket of FIG. 1 taken along section line 7-7.
Figure 7A:
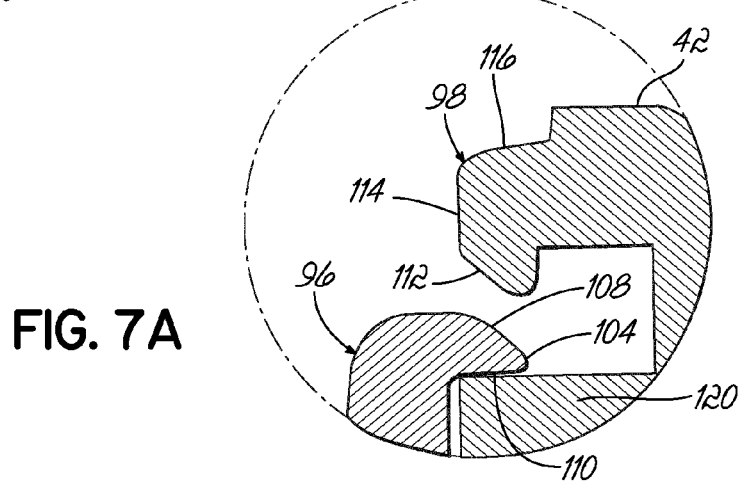
FIG. 7A is an enlarged view of the encircled area 7A of FIG. 7.

As depicted in FIGS. 7 and 7A, the receiving member 98 may define a portion of the lingual slot 48. As introduced above, the receiving member 98 cooperates with the clip 14, particularly the locking member 96, to secure the clip 14 in at least the closed position. In one embodiment, the receiving member 98 is defined by a first cam surface 112 that lies in the slide path of the locking member 96 when the clip 14 is moved toward the closed position, a second surface 114 that is oriented generally parallel with the sliding direction of the clip 14, and a third surface 116 that is oriented transverse to the slide path of the clip 14 and generally faces in the opposing direction of the first cam surface 112.

With reference to FIGS. 1, 7, and 7A, a force may be required to move the clip 14 occlusally relative to the bracket body 12 when the clip 14 is in the opened position and is moved toward the closed position. This is due to contact between the locking member 96 and the receiving member 98, specifically between the leading cam surface 108 and the first cam surface 112. In the exemplary embodiment shown, the force required to move the clip 14 must be sufficient to cause the locking member 96 to engage and deflect around the receiving member 98. Specifically, the L-shaped projection 100 must deflect mesially for the second leg 104 to pass the receiving member 98. In this regard and with reference to FIGS. 7, 7A, and 7B, the leading cam surface 108 contacts the first cam surface 112. Upon application of a sufficient force, the leading cam surface 108 slides along the first cam surface 112 thereby causing the projection 100 to deflect mesially (the deflection direction is shown by the arrow 113 in FIG. 7B). By way of example and not limitation, the leading cam surface 108 and first cam surface 112 may be shaped to facilitate sliding movement of the second leg 104 and elastic bending of the first leg 102 to allow the second leg 104 to slide occlusally past the first cam surface 112.

Figure 7B:
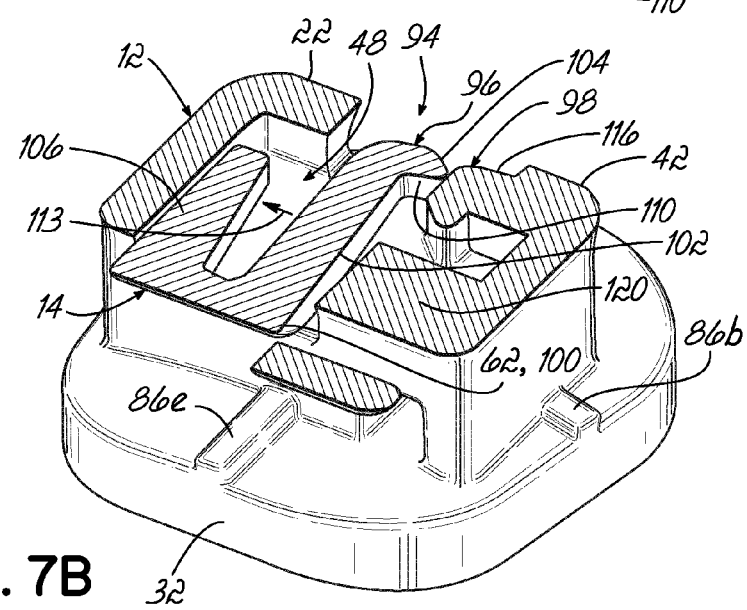
FIG. 7B is a cross-sectional perspective view of the self-ligating orthodontic bracket of FIG. 1 with the ligating clip between an opened position and a closed position.

In the exemplary embodiment shown, once the leading cam surface 108 slides past the first cam surface 112, the tip of the second leg 104 may contact and slide across the second surface 114 as shown in FIG. 7B. Once the tip of the second leg 104 traverses the occlusal-gingival length of the second surface 114, the first leg 102 springs toward its natural, unstressed state to thereby position the second leg 104 in an interference position with respect to the receiving member 98.

Figure 8:
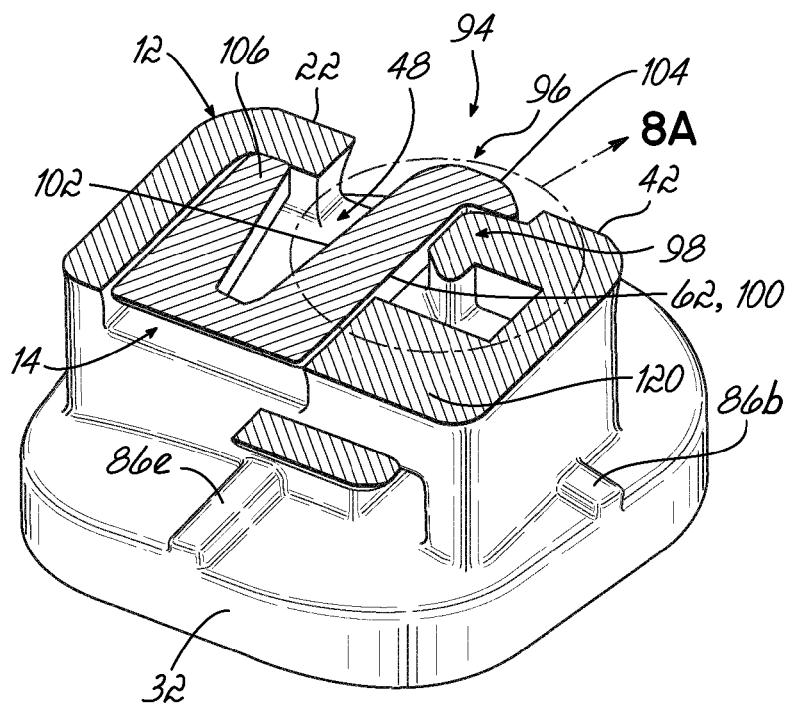
FIG. 8 is a cross-sectional perspective view of the self-ligating orthodontic bracket of FIG. 2 taken along section line 8-8.
Figure 8A:
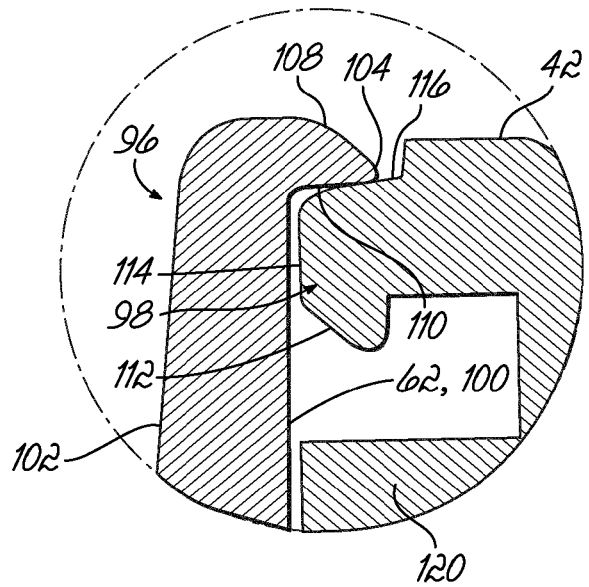
FIG. 8A is an enlarged view of the encircled area 8A of FIG. 8.

With reference to FIGS. 8 and 8A, when the clip 14 is in the closed position, the trailing abutment surface 110 is adjacent the third surface 116. This orientation causes an interference fit between the clip 14 and the bracket body 12 at this location. Accordingly, once the clip 14 is in the closed position, any force on the clip 14 that pushes it toward the opened position is resisted by the interference fit between the locking member 96 and the receiving member 98. However, the projection 100 may not necessarily contact any portion of the receiving member 98 when the clip 14 is in the closed position. The projection 100 may be in a relaxed state when the clip 14 is in the closed position. Advantageously, the clip 14 is therefore less likely to fail due to fatigue from exposure to long-term stresses. The only stress on the projection 100 may be caused by forces that cause movement of the clip 14 toward the opened position.

During treatment, it is desirable for the clinician to be able to manipulate and unlock the securing mechanism 94 and to slide the clip 14 to the opened position to gain access to the archwire slot 16. With reference to FIGS. 2, 8, and 8A, which illustrate the clip 14 in the closed position, to move the clip 14 to the opened position, a tool may be inserted into the tool receptacle 84 (FIG. 2). Application of torque to the clip 14 via the tool causes the trailing abutment surface 110 of the second leg 104 to be forced into contact with the receiving member 98. Upon application of a force that is sufficient to cause the first leg 102 to deflect toward the alignment member 106, the trailing abutment surface 110 slides across the third surface 116 while the projection 100 bends and slides in a motion similar, but in reverse, to that which occurs during movement from the opened position toward the closed position, as shown in FIG. 7B.

In one embodiment, the projection 100 deflects in the same plane as the alignment member 106. Once the deflection of the first leg 102 reaches a certain magnitude, the second leg 104 may then slide past the receiving member 98 thereby releasing the securing mechanism 94. It will be appreciated that the amount of force required to release the securing mechanism 94 may be greater than forces that are typically encountered during treatment. In one embodiment, the shape of the trailing abutment surface 110 and/or the third surface 116 may be configured such that the trailing abutment surface 110 may move past the third surface 116 at a preselected amount of torque as applied with the tool. By way of example, the third surface 116 may have a slight curvature or roundness, such that a portion of the third surface 116 is oriented at an angle that is not perpendicular to the sliding motion of the clip 14. Furthermore, it will be appreciated that the opening force may be predetermined by adjusting the shape of the third surface 116 and the trailing abutment surface 110. In any respect, the clip 14 may remain in the closed position until intentionally acted upon by a clinician. By way of further example and as shown in FIG. 5C, the shape of one trailing surface 110 and leading cam surface 108 may differ. Consequently, the force required to open and close the clip 14 may also differ. As such, or as compared to opening the clip 14 with the aid of a tool, the clinician may close the clip 14 by manually pushing on the gingival clip portion 66 until the second leg 104 clears the receiving member 98 and snaps into place to create the interference fit described above.

As shown in FIGS. 7-8, the receiving member 98 may be enclosed within the bracket body 12. Further, the third surface 116 may reside in a cutout or depression in the occlusal side 22, as shown, in the occlusal body portion 42 of the bracket body 12, though the third surface 116 may not be in a recess but merely reside lingually of the tie wing 44. When the clip 14 is in the closed position then, as shown in FIG. 8, the second leg 104 may not be accessible from the occlusal side 22 of the bracket body 12. Thus, the clinician may not have direct access to any portion of the securing mechanism 94 such that manipulation of the clip 14 with the tool is required to move the clip 14 toward the opened position. This arrangement may reduce the probability that the clip 14 is unintentionally opened during treatment.

During application of torque and movement of the clip 14, the alignment member 106 may reduce or eliminate twisting of the clip 14 within either the lingual or labial slots 48, 50. In this respect, the alignment member 106 may slide in contact with a portion of the lingual slot 48, particularly a mesial wall thereof, as shown in FIG. 7B.

In one embodiment of the present invention and with reference to FIG. 7, where the clip 14 is in the opened position, the bracket body 12 includes a second receiving member 120. Similar to the receiving member 98 described above, the second receiving member 120 forms an interference fit with a portion of the clip 14. By way of example and as shown in FIGS. 7 and 7A, the second receiving member 120 may form an interference fit with the trailing abutment surface 110 of the second leg 104. The second receiving member 120 may be positioned to reduce or eliminate the probability that the clip 14 is inadvertently removed from the bracket body 12 during treatment and during removal and installation of an archwire therein.

Figure 9:
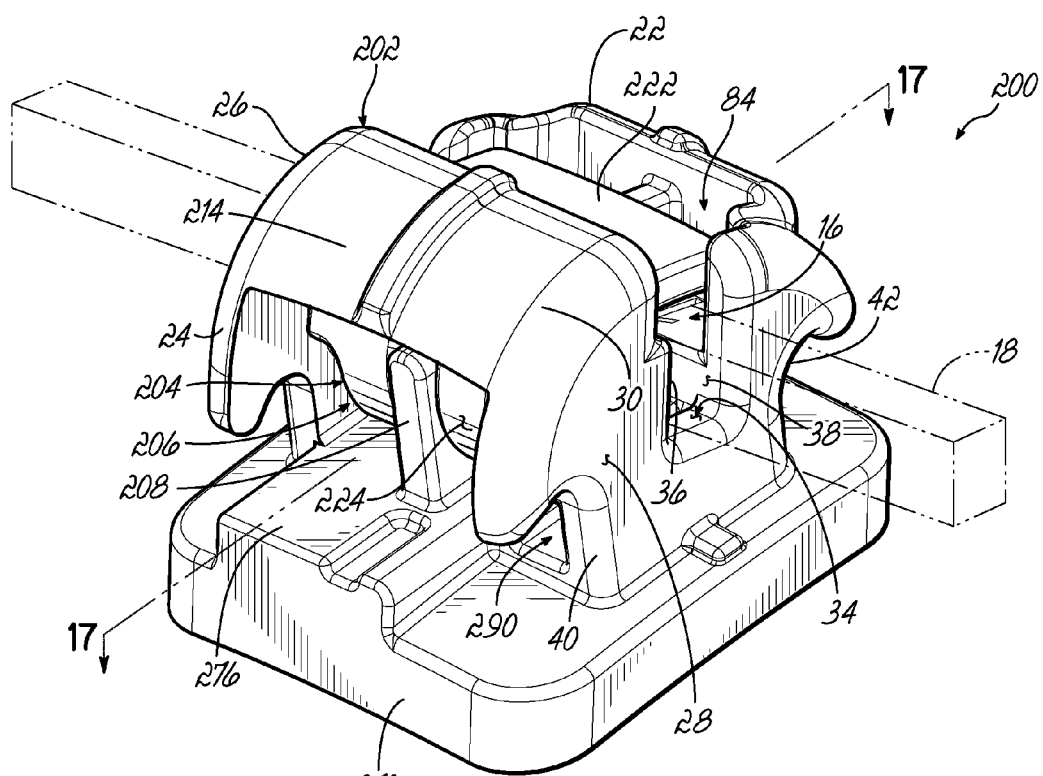
FIG. 9 is a perspective view of a self-ligating orthodontic bracket in accordance with another embodiment of the invention.
Figure 10:
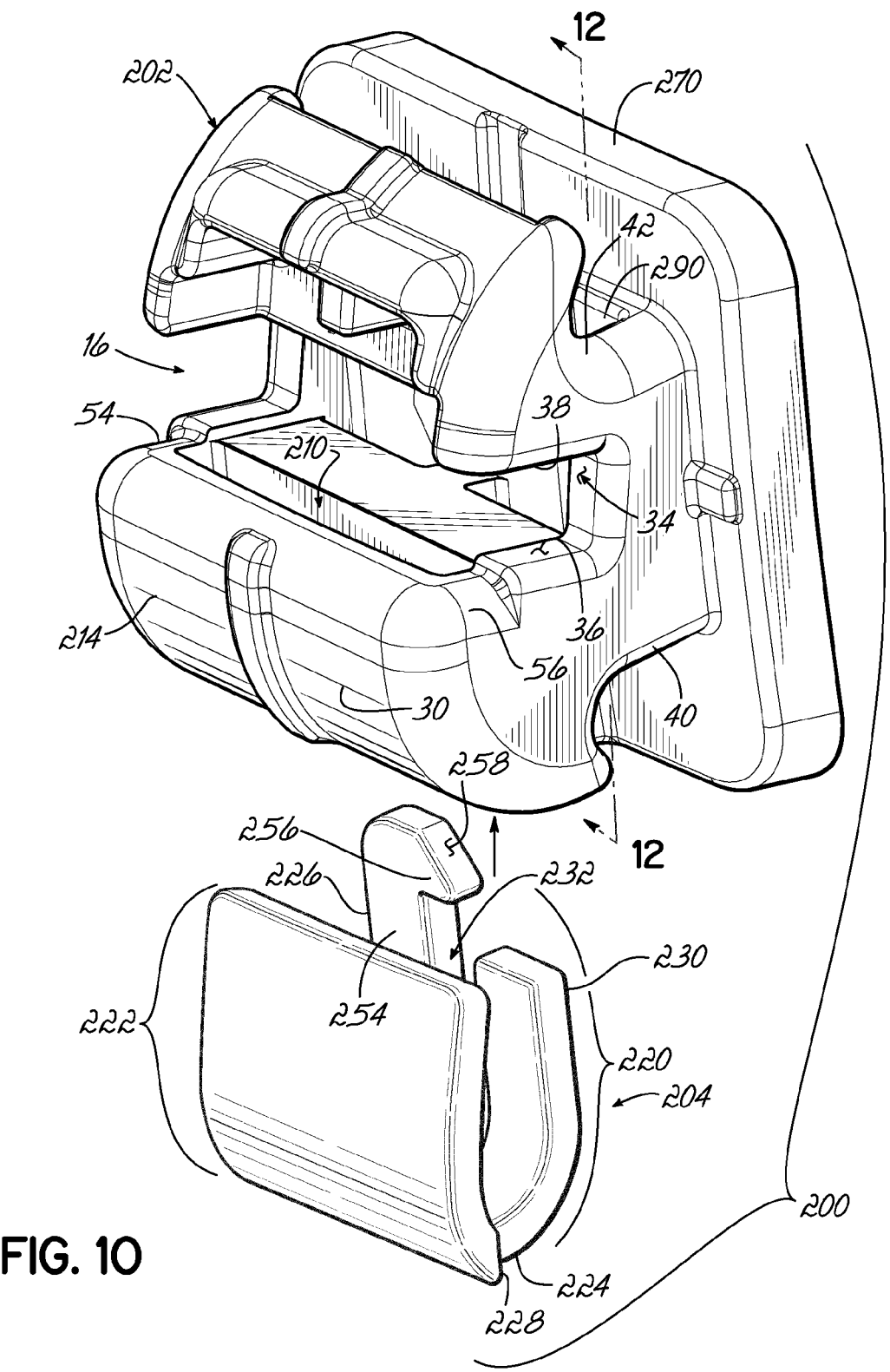
FIG. 10 is a perspective view of the orthodontic bracket shown in FIG. 9 with a ligating clip removed from the bracket body.

In accordance with an alternative embodiment of the invention and with reference to FIGS. 9 and 10, in which like reference numerals refer to like features in FIGS. 1 and 2, a bracket 200 includes a bracket body 202 and a resilient ligating clip 204 slidably received therein. The clip 204 has a closed position (FIG. 9), in which the archwire 18 is substantially prevented from inadvertently escaping from the bracket 200 during orthodontic treatment and has an opened position (not shown) where the archwire 18 may be inserted into and removed from the archwire slot 16. The bracket body 202 and the clip 204 differ in some respects from the embodiment of bracket 10 shown, for example, in FIG. 1. However, as is set forth in more detail below, the bracket 200 may be capable of retaining an archwire within the archwire slot 16 in a similar manner as the bracket 10. And, the clip 204 may be securable or lockable within the bracket body 202 in at least the closed position.

Figure 11A:
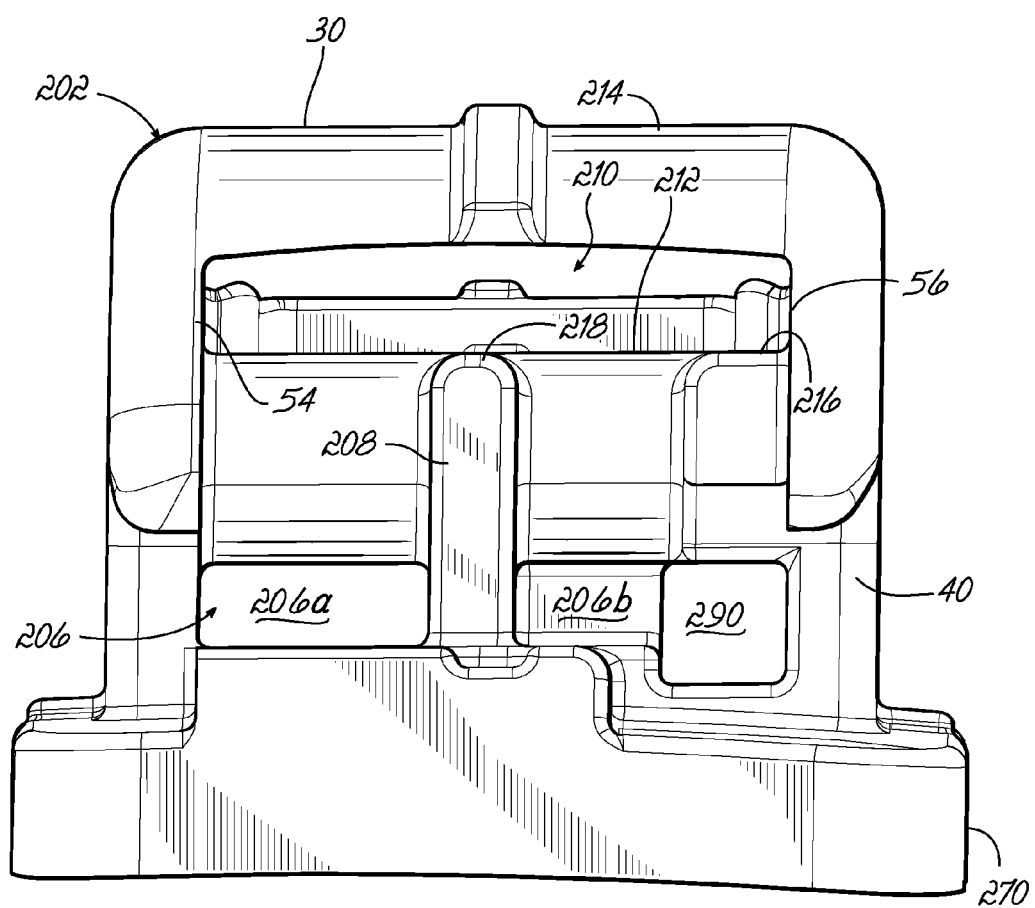
FIG. 11A is a side elevation view of the orthodontic bracket shown in FIG. 10.

To these and other ends and with reference to the exemplary embodiment shown in FIGS. 9 and 11A the bracket body 202 includes a lingual slot 206 that may extend through the bracket body 202 by passing through the gingival body portion 40 and the occlusal body portion 42. The lingual slot 206 is configured to slidably receive a portion of the ligating clip 204 in a similar manner as the lingual slot 48 receives clip 14, described above. However, in the exemplary embodiment shown, a support 208 may extend from the lingual surface of the lingual slot 206 to at least the labial surface of the slot 206 thereby dividing the slot 206 into mesial and distal portions 206a, 206b, (shown in FIG. 11A) respectively. In this embodiment, the clip 204 is configured to slidably engage slot portions 206a, 206b.

With reference to FIG. 11A, the bracket body 202 also includes a labial slot 210. The labial slot 210 is positioned labially of the lingual slot 206, extends occlusal-gingivally through the gingival body portion 40, and opens to the archwire slot 16. The labial slot 210 is defined in part by a support surface 212, which may intersect slot surface 36 at the labial-most edge thereof (as shown in FIG. 10) similar to the embodiment of the invention shown in FIG. 1. In the embodiment shown, the support 208 extends from the lingual surface of the lingual slot 206 to nearly flush in the labial direction with the support surface 212. The support surface 212 may also have a convex portion that is generally oriented in the gingival direction and that cooperates with the U-shape of the clip 204.

In the exemplary embodiment, the bracket body 202 further includes a mesial-distal bridge 214 that is similar to bridge 58 and that defines a portion of the labial side 30 of the bracket body 202. The mesial-distal bridge 214 cooperates with the clip 204, in a similar manner to that described above, to limit labial movement of the clip 204 and thus reduce the probability of inadvertent release of the archwire 18 in the labial direction from the slot 16.

As is shown best in FIG. 11A, a clip stop 216 may extend in a gingival direction from the support surface 212 and in a mesial direction from distal guide 56. The stop 216 may be in a near-contact relation with the clip 204 when the clip 204 is inserted into the bracket body 202, in a similar manner as the clip 14 and bracket body 12 shown in FIG. 1, described above. In this regard, there may be a gap between the bracket body 202 and the clip 204 at select locations, for example, between the clip stop 216 and the body 202. As described below, the stop 216 may provide a load-carrying contact point between the clip 204 and the bracket body 202 when clip 204 is deflected due to an archwire pushing in the labial direction on the clip 204. Although not shown, it will be appreciated that in addition or as an alternative to the position and orientation of the clip stop 216 above, the clip stop 216 may extend from the distal direction from the mesial guide 54.

Figure 12:
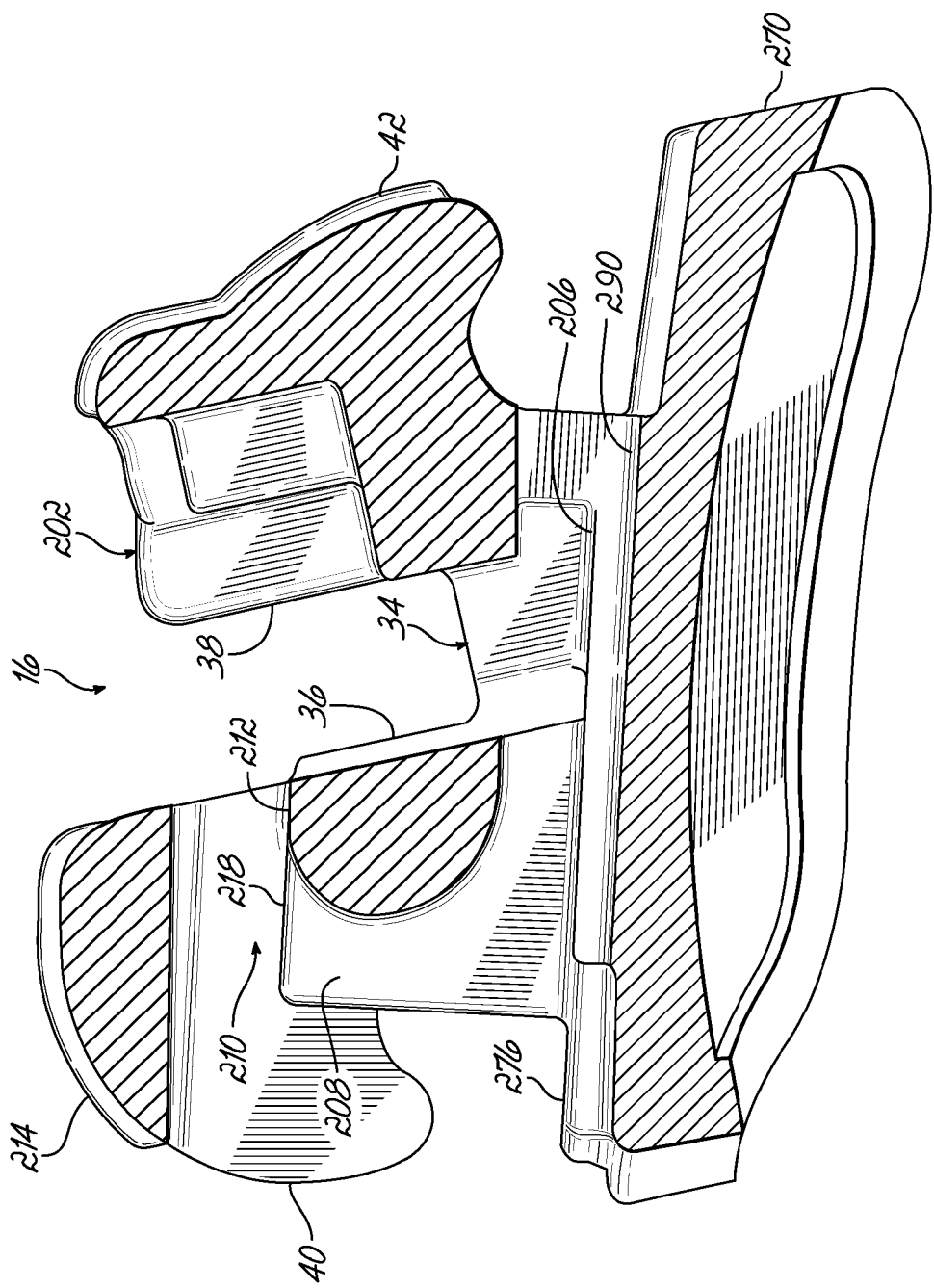
FIG. 12 is a cross-sectional view of the orthodontic bracket shown in FIG. 10 taken along section line 12-12.

Additionally, as shown in FIGS. 11A and 12, in one embodiment, the support 208 may extend labially from the slot 206 toward the slot 210 and extend gingivally from the support surface 212. The support 208 may terminate at a labial level that provides a second clip stop 218. The second clip stop 218 may extend to a greater gingival distance than the clip stop 216. Advantageously, the greater extension in the gingival direction may aid in both insertion and maintenance of the clip 204 in the bracket body 202. The clip stops 216, 218 may each provide load-carrying contact points with the clip 204 as set out below.

Figure 13A:
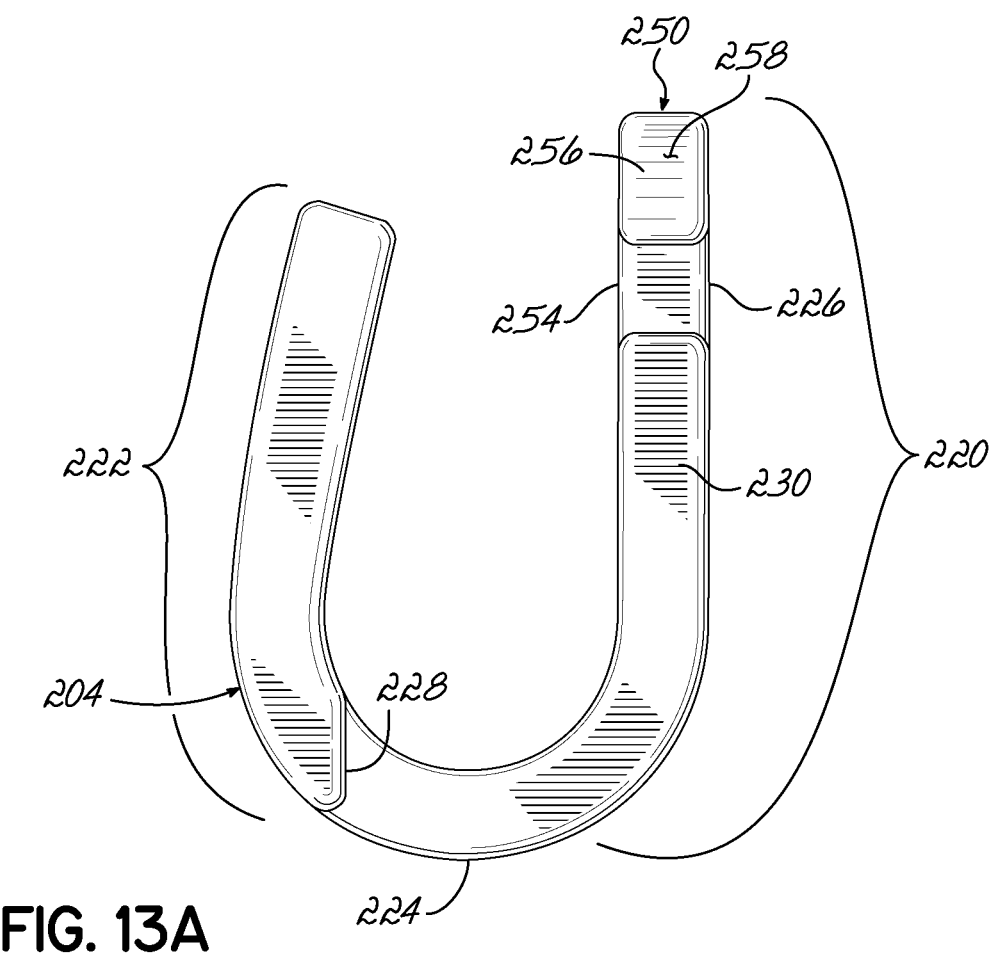
FIG. 13A is a side elevation view of the ligating clip of FIG. 10.

With reference now to FIGS. 10, 11A, and 13A, the resilient ligating clip 204 is configured to slidably engage the labial slot 210 and the lingual slot 206. As such, the clip 204 includes a lingual clip portion 220 and a labial clip portion 222 extending from a gingival clip portion 224 generally in the same direction. The clip 204 may be generally U-shaped, as shown in FIG. 13A. In this regard, the lingual clip portion 220 is insertable into the lingual slot 206 while the labial clip portion 222 is insertable into the labial slot 210.

In addition, the clip 204 may comprise a superelastic metal alloy as set forth above with respect to clip 14. Further, in one embodiment, the respective stiffnesses of the clip portions 220, 222, 224 may differ, similar to that described above with respect to clip 14. By way of example, the gingival clip portion 224 may be more stiff than either of the lingual clip portion 220 or the labial clip portion 222, which may be about the same stiffness. The stiffness of the clip 204 may be one factor in the amount that the clip 204 deflects while retaining the archwire in the archwire slot 16.

The clip 204 is movable between an opened position and a closed position. When the clip 204 is in the closed position, as shown in FIG. 9, the labial clip portion 222 extends over the archwire slot 16 and inhibits inadvertent removal of the archwire 18 therefrom. In one embodiment, as set forth in detail below, the lingual clip portion 220 cooperates with the bracket body 202 to secure the clip 204 in at least the closed position.

Figure 13B:
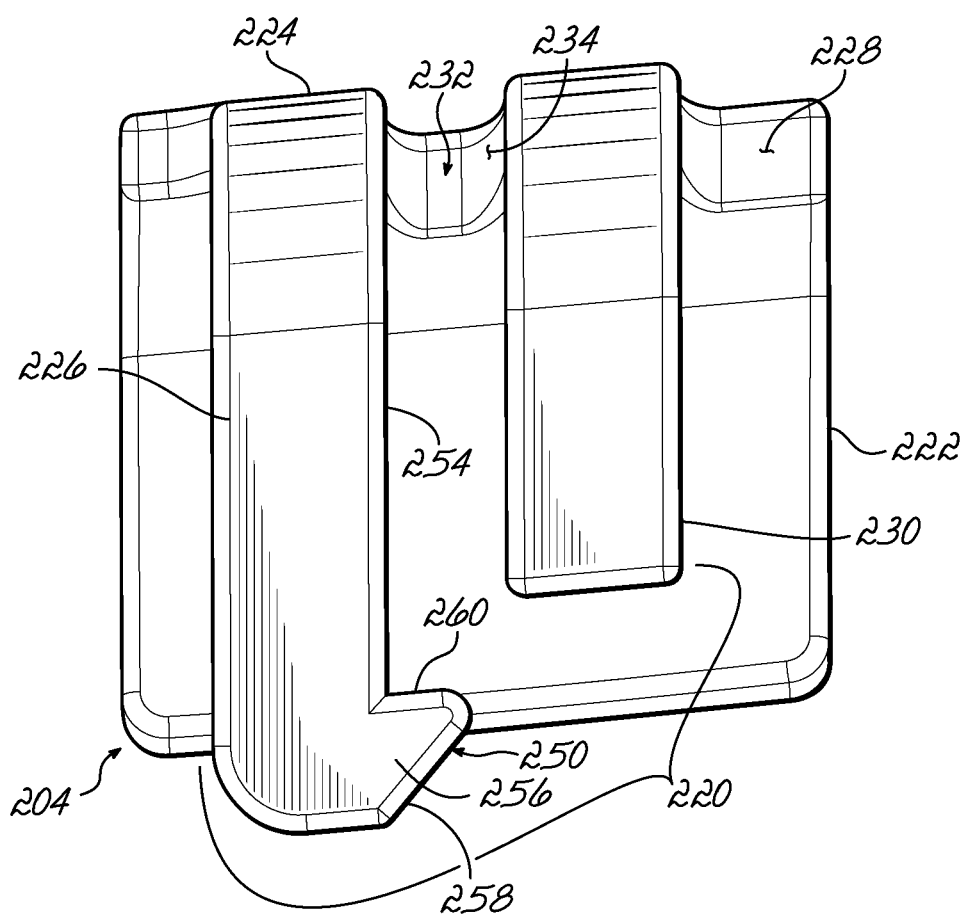
FIG. 13B is a plan view of the ligating clip of FIG. 10.

In addition and in one embodiment, and with reference to FIG. 13B, a projection 226 may define at least a portion of the lingual clip portion 220 and the gingival clip portion 224. And, the lingual clip portion 220 and the gingival clip portion 224 may further include an alignment member 230 separated from the projection 226 by a U-shaped cutout 232. As shown, the U-shaped cutout 232 may extend through the gingival clip portion 224 to the labial clip portion 222 and may be configured to cooperate with the support 208 such that the alignment member 230 and the projection 226 straddle the support 208, as set forth above and shown in FIG. 9.

In one embodiment, and with reference to FIGS. 10 and 11A, the U-shaped cutout 232 allows the alignment member 230 and projection 226 to slidably engage one or both sides of the support 208 thereby keeping the clip 204 from twisting relative to the bracket body 202 particularly as the clip 204 is moved between opened and closed positions. It will be appreciated that the positions of the projection 226 and the alignment member 230 are not limited to those shown in the figures, as the projection 226 and alignment member 230 may be interchanged and retain their respective functions.

Additionally, as shown in FIGS. 13A and 13B, the periphery of the clip 204 defines a shoulder 228, much like shoulder 70 shown in FIGS. 1, 5A, and 5B. In one embodiment, the periphery of U-shaped cutout 232 defines a second shoulder 234 (FIG. 13B) at the apex of the cutout 232 between the projection 226 and the alignment member 230. As with the shoulder 228, the second shoulder 234 may provide a load-carrying contact point between the labial clip portion 222 and the bracket body 202.

During treatment and with regard to capturing the archwire 18 in the archwire slot 16, when the ligating clip 204 is in the closed position, as shown in FIG. 9, the labial clip portion 222 covers the archwire slot 16, and the projection 226 and the alignment member 230 straddle the support 208. When the archwire 18 is not in contact with the clip 204, the clip stop 216 may be in near-contact relation with the shoulder 228, the second clip stop 218 may be in near-contact relation with the second shoulder 234, and the labial clip portion 222 may be in near-contact relation with the mesial-distal bridge 214. As such, there may be a gap or space between the clip stop 216 and the shoulder 228, between the clip stop 218 and the second shoulder 234, and/or the labial clip portion 222 and the bridge 214. The gap may be a predetermined distance and may depend on the stiffness of the clip 204, for example, as well as other possible factors.

Although not shown, in the situation where the archwire 18 pulls labially on the labial clip portion 222 causing it to deflect or elastically bend, the bracket body 202 and ligating clip 204 may be forced into contact with one another. By way of example, the bracket body 202 and the clip 204 may contact one another between the mesial-distal bridge 214, the clip stop 216, and/or the second clip stop 218 on the bracket body 202 and the labial clip portion 222, the shoulder 228, and/or the shoulder 234, respectively, on the clip 204. These contact locations are similar to those shown in FIGS. 6A and 6B, above. In other words, at positions where there is initially no contact between the clip 204 and the body 202, labial movement of the archwire 18 may move the labial clip portion 222 and/or the gingival clip portion 224 lingually into contact with the portions of the bracket body 202 that are in close proximity.

As a result, the contact surface area between the clip 204 and the bracket body 202 may therefore increase when loads are imposed on the archwire 18 tending to pull the archwire 18 labially. It will be appreciated that it is not necessary that each of the above-mentioned contacts be made, rather one or more may occur during deflection of the labial clip portion 222. The amount of the deflection may then determine the number of contact locations. For example, the greater the load imposed on the archwire, the greater the number of contact locations between the clip 204 and the bracket body 202. By way of further example, along similar lines, when multiple contacts are generated by deflection of the labial clip portion 222, the contacts between the bracket body 202 and the clip 204 may be substantially simultaneous or sequential, in which case the order of the contacts may also depend on the amount of load placed on the clip 204 by the archwire 18. However, in one embodiment, one contact location is sufficient to prevent the archwire 18 from inadvertently escaping the archwire slot 16. It will further be appreciated that contact areas between any or all of the clip stops 216 and 218 and the mesial-distal bridge 214 may be in addition to other surface contact locations, such as, between the clip 204 and the bracket body 202 within the lingual slot 206. In one embodiment, the clip 204 is capable of contacting the bracket body 202 only on the gingival body portion 40 thereof.

Figure 15:
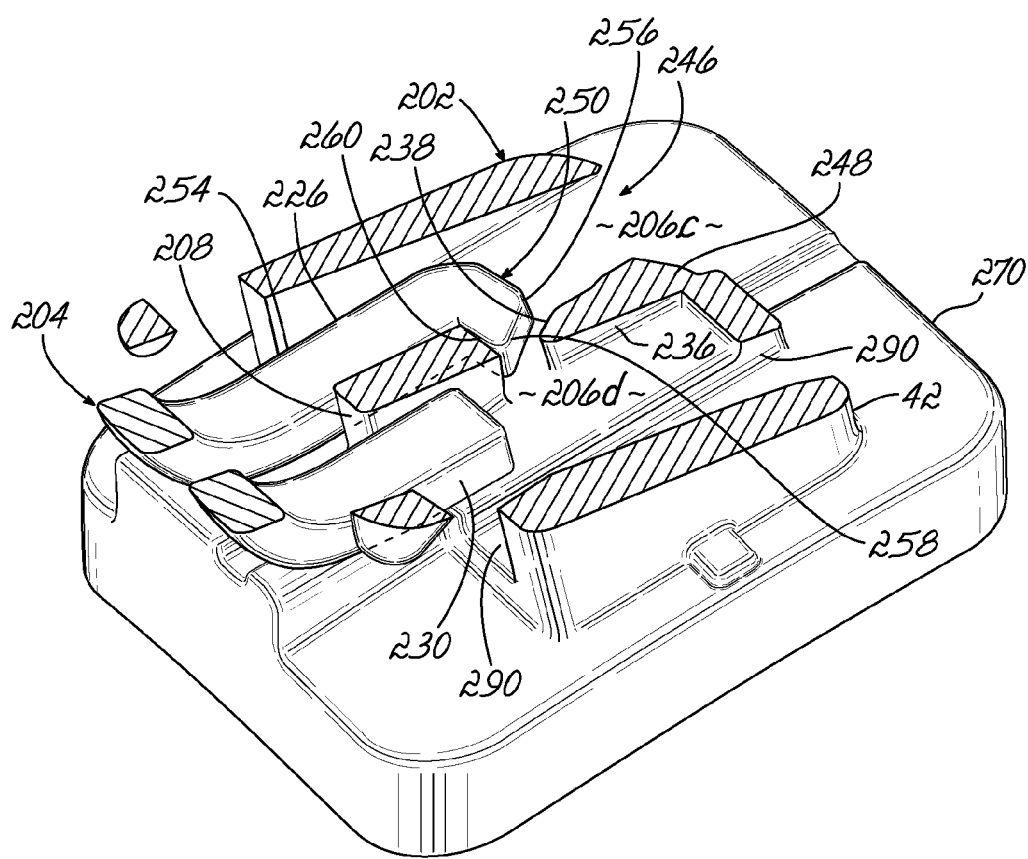
FIG. 15 is a cross-sectional perspective view of the self-ligating orthodontic bracket of FIG. 9 with the ligating clip in the opened position.
Figure 16:
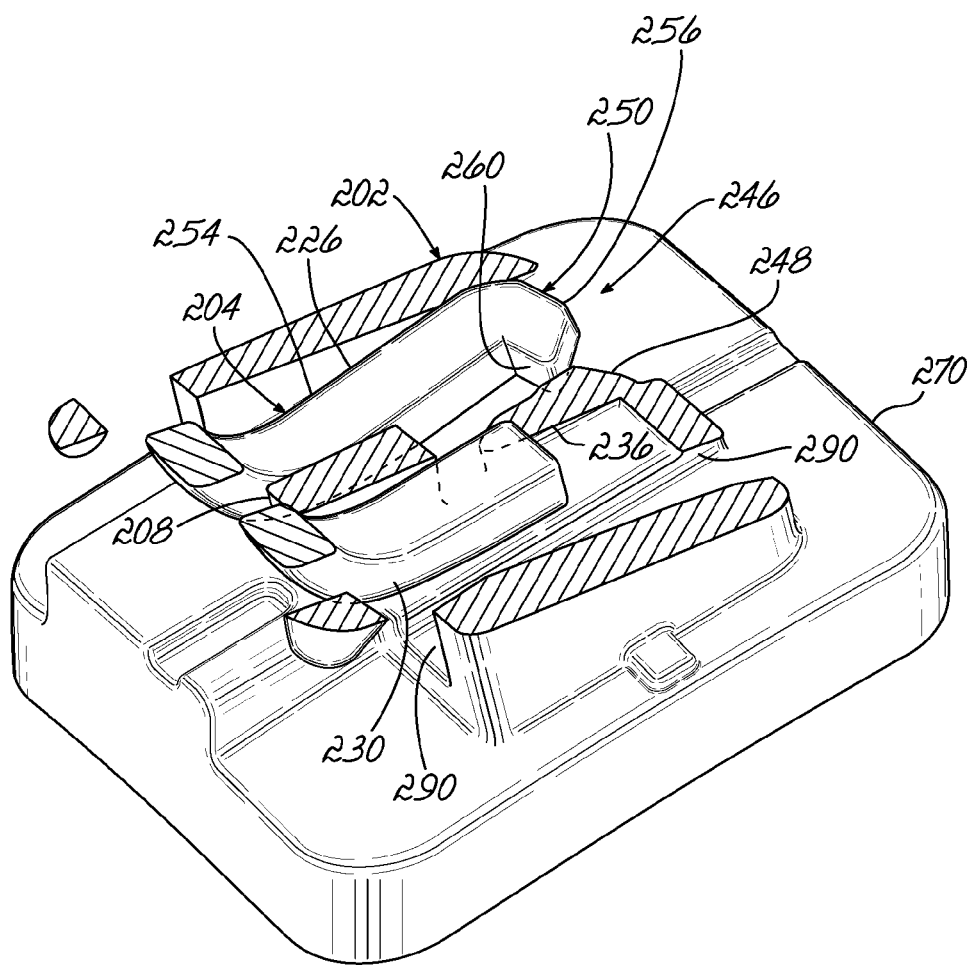
FIG. 16 is a cross-sectional perspective view of the self-ligating orthodontic bracket of FIG. 9 with the ligating clip between the opened position and the closed position.
Figure 17:
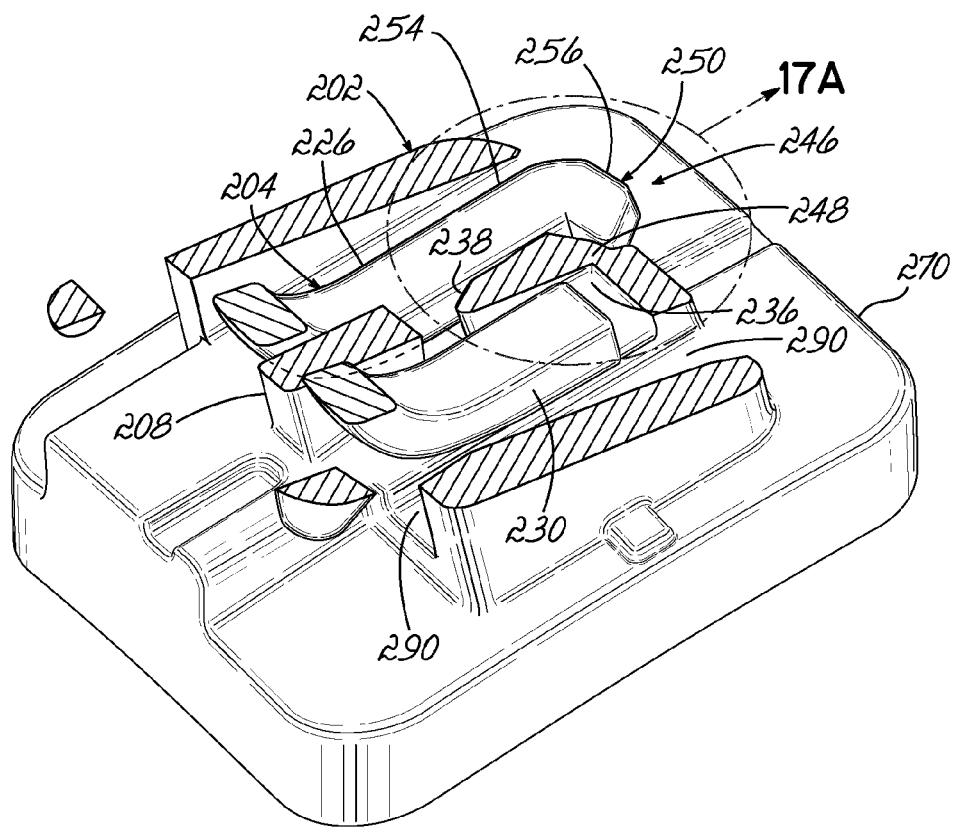
FIG. 17 is a cross-sectional perspective view of the self-ligating orthodontic bracket of FIG. 9 taken along section line 17-17.

As introduced above, the clip 204 has an opened position and a closed position to allow access to the archwire slot 16 and to capture the archwire 18 in the archwire slot 16, respectively. In this regard, the clip 204 may be securable in one or both of the opened and closed positions. With reference to FIGS. 15-17, in one embodiment, the bracket 200 comprises a securing mechanism 246 for securing the clip 204 in at least the closed position.

Similar to the securing mechanism 94 above, the securing mechanism 246 includes a receiving member 248 that cooperates with a locking member 250. Although this embodiment is described with the locking member 250 associated with the clip 204 and the receiving member 248 associated with the bracket body 202, those of ordinary skill in the art will recognize that the invention is not so limited. For example, although not shown, the locking member 250 may be associated with or be coupled to the bracket body 202 and the receiving member 248 may be associated with or be formed in the ligating clip 204.

To this end, and with continued reference to FIGS. 15-17, the receiving member 248 may include a divider 236 defined by the bracket body 202 and that separates the lingual slot 206 in the gingival body portion 40 into mesial and distal portions 206a and 206b (FIG. 11A) and separates the lingual slot 206 in the occlusal body portion 42 into mesial and distal portions 206c and 206d. The portions 206c and 206d may be aligned with and be similar in width to the mesial and distal portions 206a and 206b, respectively. The mesial portions 206a and 206c and distal portions 206b and 206d are configured to slidably receive the projection 226 and the alignment member 230, respectively. In this regard, the divider 236 may be substantially aligned with the support 208 which may guide movement of the clip 204 between opened and closed positions.

Figure 17A:
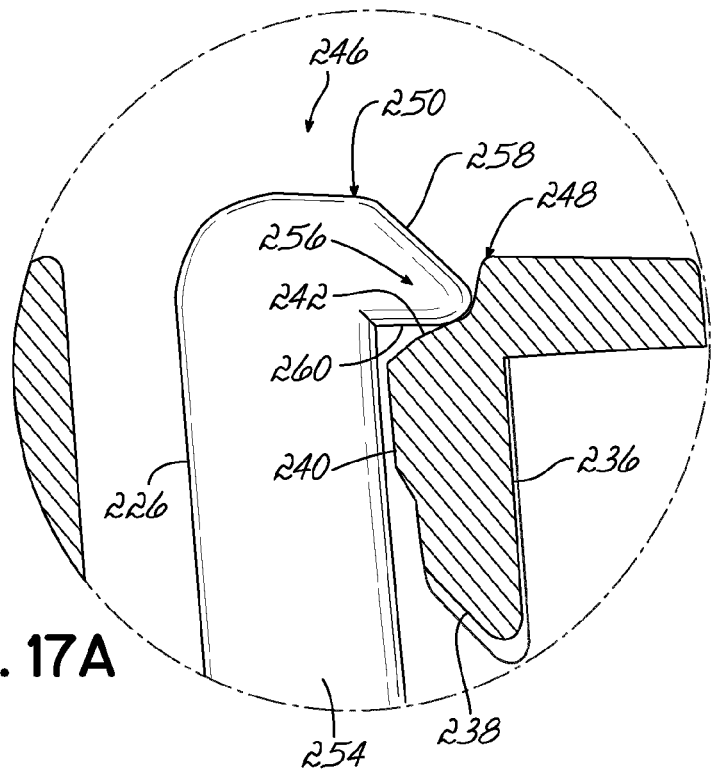
FIG. 17A is an enlarged view of the encircled area 17A of FIG. 17.

In addition, as shown in FIG. 17A, the divider 236 may be defined by at least three surfaces 238, 240, 242 that contact portions of the clip 204 when it is moved between the opened and closed positions. Surfaces 238, 240 and 242 may be similar in orientation and shape as the first, second, and third surfaces 112, 114, 116 of the receiving member 98 shown in FIG. 7B, for example. The function of the surfaces 238, 240 and 242 is described in more detail below in conjunction with the locking member 250.

With reference to FIGS. 13B and 15, the locking member 250 may include the L-shaped projection 226 that has a first leg 254 and a second leg 256. In the embodiment depicted, the L-shaped projection 226 extends distally from the gingival clip portion 224 on the mesial side of the clip 204. As such, the second leg 256 extends toward the centerline of the clip 204. Thus, the second leg 256 extends toward the alignment member 230 and is separated therefrom by the U-shaped cutout 232. The U-shaped cutout 232 allows the second leg 256 to flex away from the alignment member 230 in the plane of the lingual clip portion 220. The capability of the second leg 256 to flex allows the clip 204 to be securable to the bracket body 202.

In this regard and in one embodiment shown in FIGS. 15, 16, 17 and 17A, the second leg 256 defines a leading surface 258 that opposes a trailing surface 260. In sliding the clip 204 between the opened and the closed positions, the leading surface 258 and trailing surface 260 cooperate with the divider 236 along surfaces 238, 240, 242 (FIG. 17A) to secure the clip 204 in at least the closed position, as discussed below. Furthermore, the alignment member 230 may substantially prevent twisting of the clip 204 in the bracket body 202 by sliding along the support 208 and the divider 236 as set out above.

With reference to the exemplary embodiment shown in FIGS. 15, 16, and 17, the operation of the securing mechanism 246 is depicted in each of the closed, intermediate, and opened positions of the clip 204, respectively. In sliding the clip 204 from the opened position (FIG. 15) to an intermediate position (FIG. 16) and to the closed position (FIG. 17), the leading surface 258 contacts the divider 236 on surface 238. The orientation of the surfaces 258 and 238 at contact causes the first leg 254 to deflect away from the alignment member 230 when the clip 204 is moved toward the closed position. The leading surface 258 and surface 238 may each be oriented at an angle relative to the sliding direction of the clip 204 to cause the projection 226 to deflect when forced into contact with the divider 236. The corresponding angles may be approximately equal though it will be appreciated that the orientation of the two surfaces may be predetermined and relate directly to the amount of force needed to cause the projection 226 to deflect and then slide by the divider 236.

The intermediate position shown (FIG. 16) is representative of one position of the clip 204 between the opened and closed positions where at least a portion of the projection 226 is deflected by the divider 236. In this position, the securing mechanism 246 is not engaged. The clip 204 may, therefore, be moved gingivally and/or occlusally over a short distance between the opened and closed positions, such as, the length of the divider 236, with minimal force. The force required to slide the clip 204 once the projection 226 is deflected may be less than that force which is required to cause the projection 226 to deflect. That is, it may become easier to push the clip 204 once the projection 226 is deflected by the divider 236. Furthermore, in this position, the stresses generated in the projection 226 are temporary, lasting only as long the projection 226 is deflected, which is usually as long as it takes for the clinician to move the clip 204 between the opened and the closed positions. In this regard and in one embodiment, the lingual clip portion 220, particularly the projection 226 is in a relaxed or unstressed state when the clip 204 is in the closed and the opened positions.

With continued reference to FIG. 16, application of a sufficient force to cause the clip 204 to move into the closed position allows the second leg 256 to move past the divider 236 into a position shown, for example, in FIGS. 17 and 17A. Once the second leg 256 is forced past the divider 236, the projection 226 snaps into a position that places the trailing surface 260 in an orientation that interferes with the movement of the clip 204 from the closed position to the opened position. This movement of the projection 226 toward its undeflected position may be associated with an audible click or tactile response which may signal to the clinician that the clip 204 is in the closed position. In this position, the securing mechanism 246 is engaged and resists unintentional movement of the clip 204 from the closed position, such as toward the opened position. Specifically, as shown in FIG. 17A, the trailing surface 260 is in an orientation that creates an interference fit with the bracket body 202. It is the interference fit that restricts the movement of the clip 204 from the closed position toward the opened position. For example, the trailing surface 260 is configured to contact the third surface 242 to secure the clip 204 in the closed position. As such, any forces on the clip 204, particularly forces generated by contact with the archwire 18 and that tend to move the clip 204 toward the opened position are resisted by contact between the trailing surface 260 and third surface 242.

Once the clip 204 is in the closed position, a clinician may unlock or disengage the securing mechanism 246 to move the clip 204 toward the opened position, for example, to exchange an archwire. In one embodiment, a clinician may use a tool to apply a torque on the clip 204 of sufficient magnitude to cause the securing mechanism 246 to disengage. The clip 204 is then able to slide gingivally in slots 206, 210. To disengage the securing mechanism 246, in one embodiment, the clinician inserts the tool into the tool receptacle 84 (shown in FIG. 9). Using the tool to move the clip 204 from the closed position is similar to that described above with regard to the embodiment shown in FIG. 1. Upon application of a sufficient force to the labial clip portion 222, the projection 226 is forced to deflect away from the alignment member 230 around the divider 236. Once the projection 226 is deflected, the clip 204 may then be moved to the opened position. It will be appreciated the shapes of one or both surfaces of the trailing surface 260 and the receiving member 248 cooperate to resist forces that move the clip 204 to the opened position of up to a certain predetermined magnitude. At a predetermined threshold force, the projection 226 will deflect transversely such that the second leg 256 clears the surface 242 and slides along the divider 236 at surfaces 240 and 238. It will be appreciated that the predetermined threshold force is greater than those forces that are normally encountered during treatment or during mastication and may be achievable through the use of a tool in cooperation with the tool receptacle 84.

Figure 14:
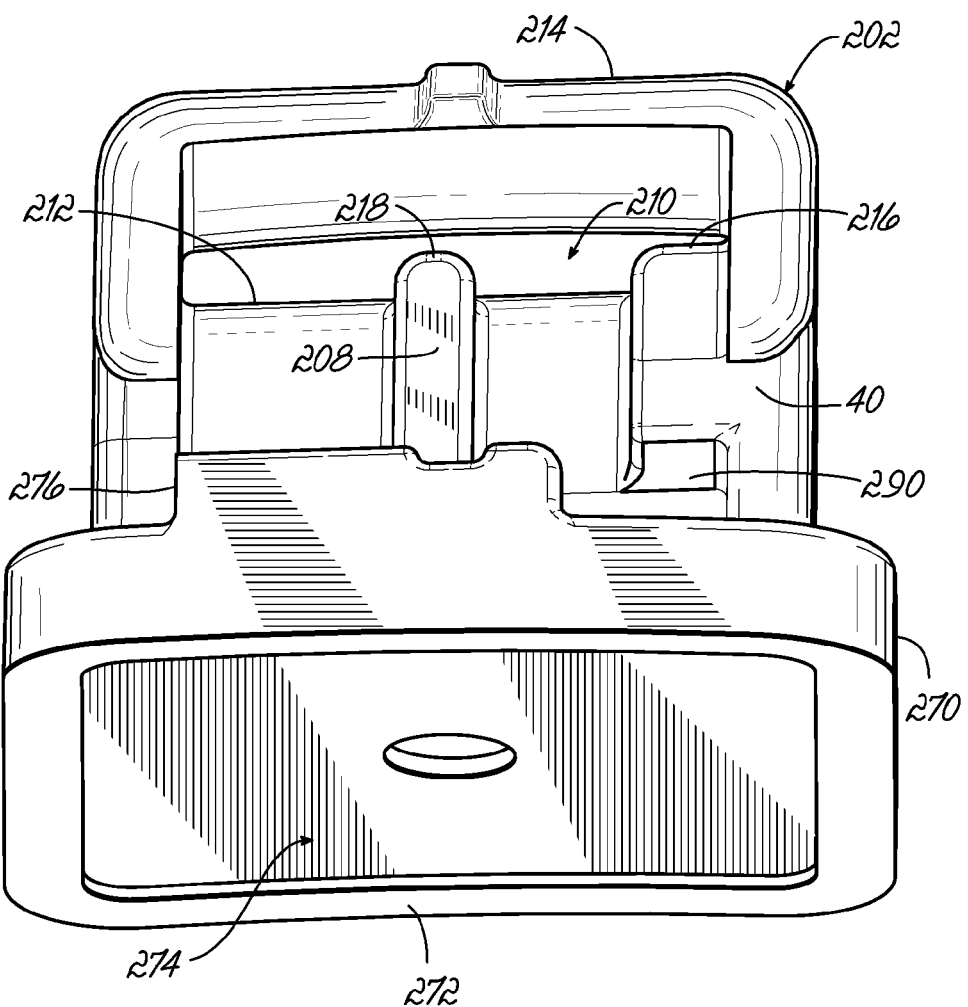
FIG. 14 is a bottom perspective view of the self-ligating orthodontic bracket shown in FIG. 10.

Additionally, in one embodiment of the invention shown in FIGS. 9, 12, and 15, the bracket body 202 includes a pad 270. The pad 270 is similar to the pad 32 in that it defines a bonding base that is configured to be secured to the surface of the tooth and may be coupled to the bracket body 12 as a separate piece or element, or alternatively may be integrally formed with the bracket body 202. In one embodiment, shown in FIG. 14, the tooth contact surface of the pad 270 may have a raised border 272 that extends the circumference of the lingual surface of the pad 270. The raised border 272 defines a recess 274 and provides a surface that is configured to bond the bracket body 202 to a tooth surface. The recess 274 is configured to allow the surface thereof to be laser etched such that the border 272 remains unaffected by the laser-etching process. Such processes are known in the art according to U.S. Publication Nos. 2006/0166158, 2006/0163774, and 2006/0166159, which are incorporated by reference herein in their entireties. It will be appreciated that the byproduct or ejected material from the laser etching process does not interfere with or change the surface of the border 272. Consequently, the border 272 allows the surface within the recess 274 to be prepared without affecting the accuracy of the tooth contact surface defined by the border 272.

In one embodiment, as shown in FIG. 9, the bracket body 202 may further include a gingival extension 276 that projects from the gingival body portion 40 lingually of the lingual slot 206. The gingival extension 276 may extend gingivally and may be flush with the periphery of the pad 270. Thus, the gingival extension 276 may be supported by the pad 270 along its length. In one embodiment, as shown in FIG. 11A, the lingual-most surface of the slot 206 and the gingival extension 276 may be substantially coplanar. By this configuration, the clip 204 may find additional structural support when it is in the opened position. That is, when the clip 204 is moved or slid to the opened position, the gingival extension 276 contacts the lingual clip portion 220 thereby supporting the clip 204 in the lingual direction. The gingival extension 276 may thereby prevent the clip 204 from tipping lingually when in the opened position, avoiding the possibility that the labial clip portion 222 slides off of the second clip stop 218 or otherwise disengages from the bracket body 202. In such a case, the clinician may be required to reset the labial clip portion 222 on the second clip stop 218 before the clip 204 may be reinserted into the labial slot 210. In this manner, the gingival extension 276 may advantageously reduce the time required for the clinician to change archwires as the gingival extension 276 may reduce the likelihood that the clip 204 becomes twisted in the slot 206 or disconnected from the bracket body 202.

With reference to FIGS. 9, 11A, 11B, and 12, in one embodiment, the bracket body 202 further includes a gingival-occlusal extending bore 290, which is similar to the bore 90 shown in the exemplary embodiment of FIG. 1. However, as shown, the bore 290 may be generally coplanar with the slot 206 (FIG. 12). In one embodiment, one side of the bore 290 or a majority thereof may be formed by the clip 204 upon its insertion. This is shown in FIG. 11A in which the distal portion 206b of the lingual slot 206 is open to the bore 290. In this regard, the bore 290 is not fully formed until the clip 204 is inserted into the bracket body 202. That is, one portion of the bore 290 is formed by the alignment member 230 of the clip 204 when it is inserted into the slot 206b. Advantageously, a configuration in which one side of the bore 290 or a portion thereof is formed by the clip 204 may reduce the overall size of the bracket body 202. That is, the configuration may save space though without loss of the functions set out herein. Although the bore 290 may not be fully formed until the clip 204 is inserted into the slot 206, it will be appreciated that an auxiliary device (not shown) may be inserted prior to or following the insertion of the clip 204. The auxiliary device may even be used during treatment though the clip 204 may not be initially used. It will be appreciated, however, that the bore 290 may be fully defined by the bracket body 202.

Figure 11B:
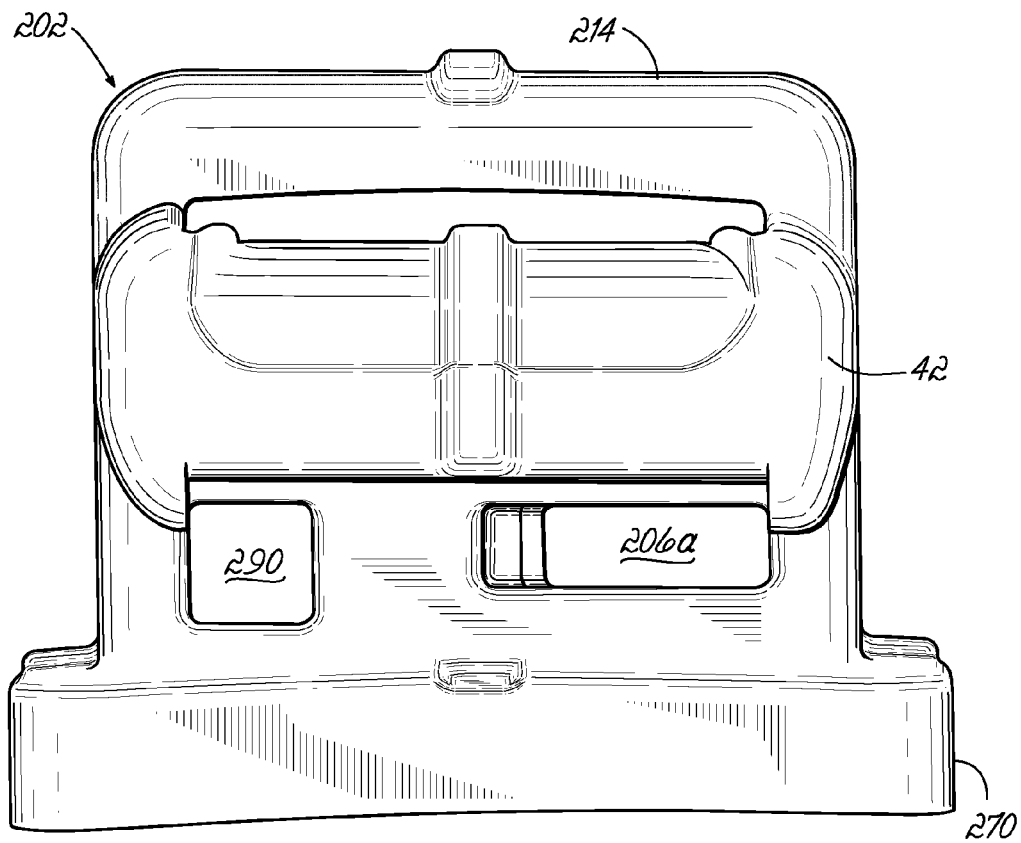
FIG. 11B is a side elevation view of the orthodontic bracket shown in FIG. 10 from the opposite direction of the view shown in FIG. 11A.

In yet another alternative, the bracket body 202 may define all sides of the bore 290, but only along a portion of the length of the bore 290. For example, where the slot 206b is closed at the occlusal end thereof (i.e., the slot 206b is a blind bore), as shown in FIG. 11B, the bracket body 202 forms four sides of the bore 290.

Figure 18:
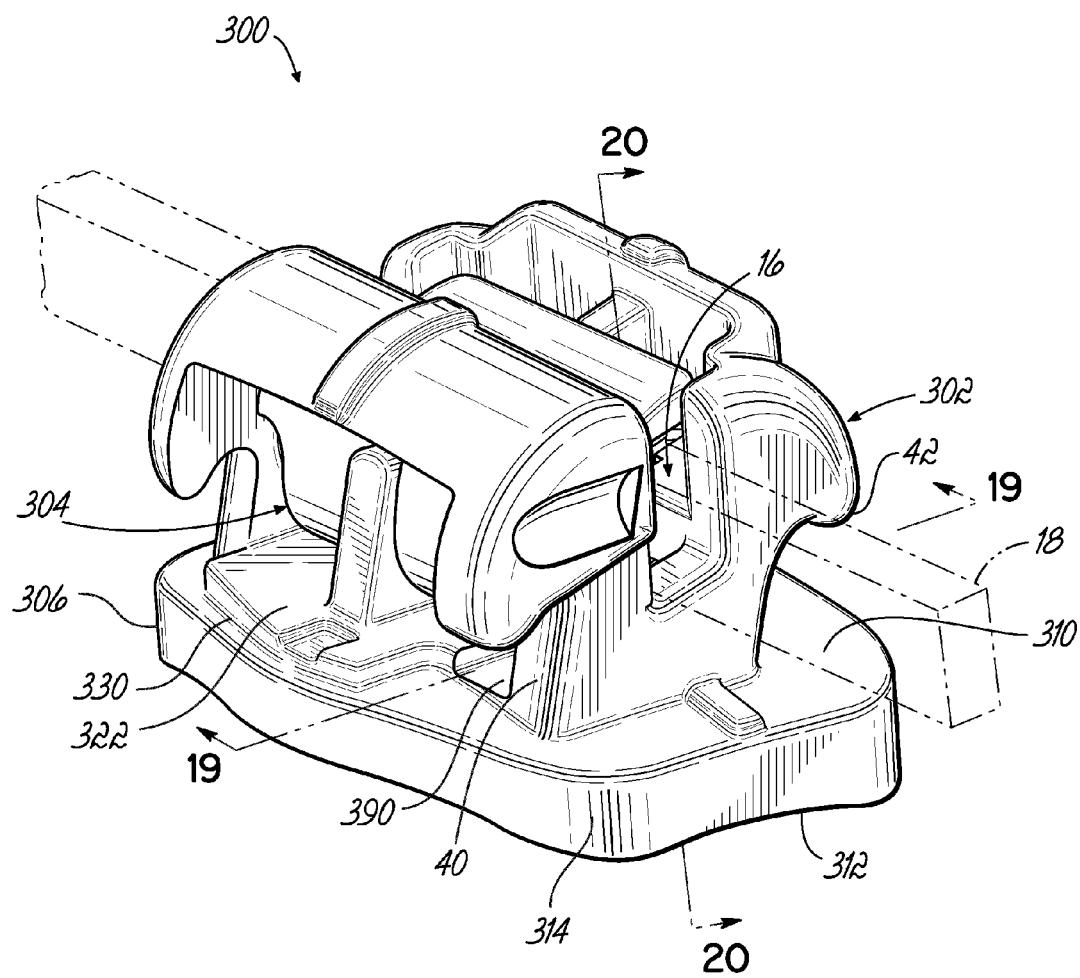
FIG. 18 is a perspective view of a self-ligating orthodontic bracket in accordance with another embodiment of the present invention.
Figure 19:
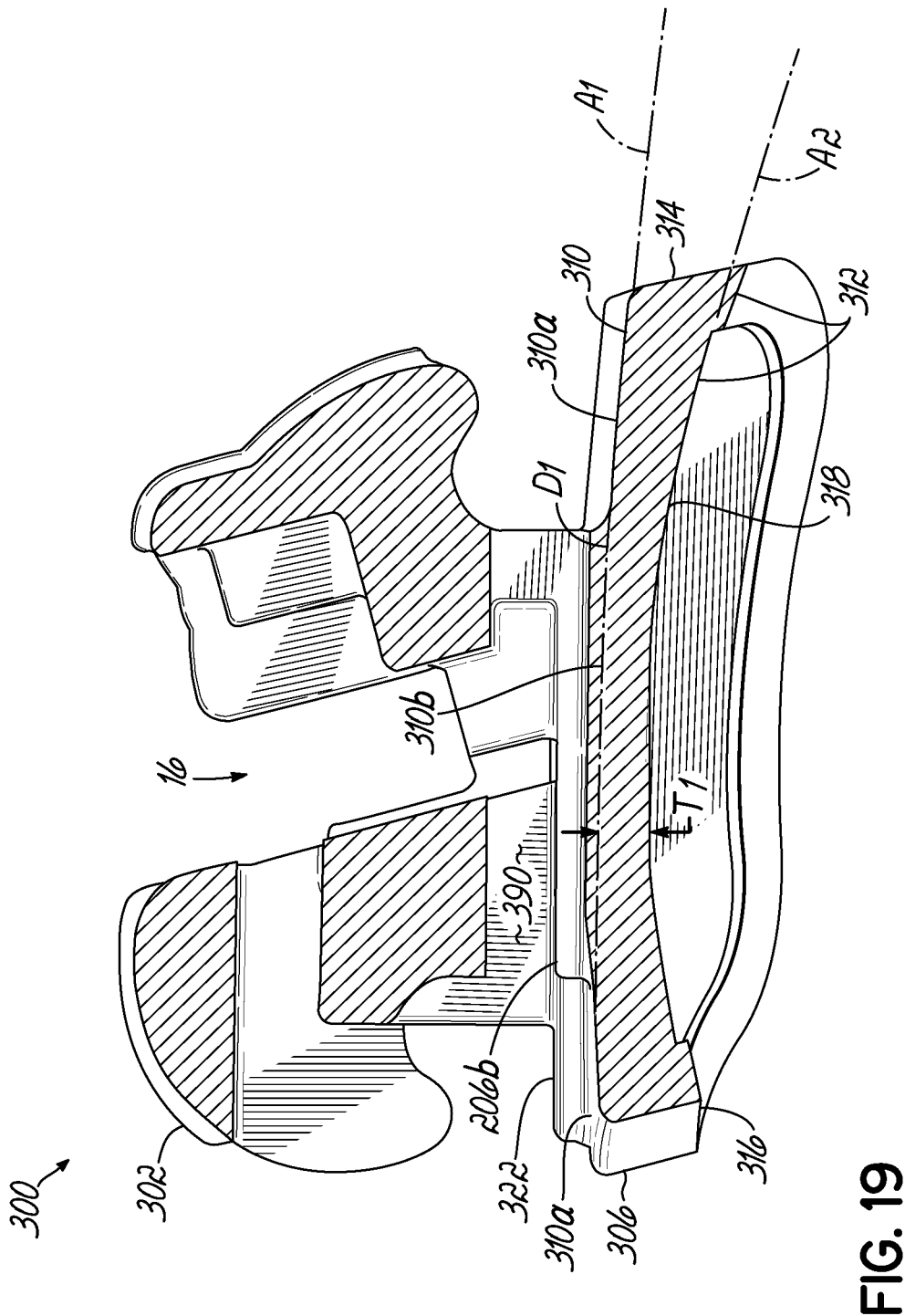
FIG. 19 is a cross-sectional view of the orthodontic bracket shown in FIG. 18 taken along section line 19-19.

In accordance with an alternative embodiment of the invention and with reference to FIGS. 18 and 19 in which like reference numerals refer to like features in the figures set forth above including, for example, FIGS. 9 and 10, a bracket 300 includes a bracket body 302 and a resilient ligating clip 304 slidably received therein. The clip 304 is substantially similar to the clip 204 shown in FIG. 9. The clip 304 has a closed position (shown in FIG. 18), in which the archwire 18 is substantially prevented from inadvertently escaping therefrom during orthodontic treatment and an opened position (not shown) in which the archwire 18 may be inserted into and removed from the archwire slot 16. The bracket body 302 differs from the embodiment of bracket body 202 shown, for example, in FIG. 9.

In this regard, in one embodiment, the bracket body 302 includes a pad 306 that is configured to contact and facilitate bonding of the body 302 to a tooth surface (not shown). Like the pad 270, described above, the pad 306 may be a separate piece or element, or alternatively may be integrally formed with the bracket body 302. The pad 306 is defined by an upper or labial surface 310, an opposing tooth-facing surface 312, and an outer periphery 314.

Where the pad 306 is integral with the bracket body 302, as shown in FIG. 19, a portion of the labial surface 310 is occupied by the bracket body 302. The labial surface 310 may therefore be described by labial surface 310a, which is visible, and labial surface 310b, which is not visible. The labial surface 310b of the pad 306 is determined by extending the portion of the labial surface 310a, which extends beyond the footprint of the bracket body 302 along one side of the pad 306, to an opposing portion of the labial surface 310a. As shown, the labial surface 310b and the visible labial surface 310a are continuous. The constructed labial surface 310b may therefore be, in essence, an inward interpolation of labial surface 310a or a natural extension thereof. This construction may be readily observed using three-dimensional models generated by commercially available software and utilizing tools made available by such software to interpolate a best fit line between the opposing visible surfaces 310a. For example, in the simplest pad design, where both surfaces of the pad are flat or nearly so, the constructed labial surface will also be flat or nearly flat and will be in about the same plane as the visible labial surface.

By way of additional example, in the embodiment depicted in FIG. 19, the labial surface 310 is shaped generally as an arc, A1. The bracket body 302 is the portion of the bracket 300 extending away from the labial surface 310 of the pad 306 even though the bracket body 302 may be integral with the pad 306. As shown, this includes portions of the bracket 300 in the labial direction from A1. The visible labial surface 310a is shown extending beyond the occlusal and gingival sides of the bracket body 302. The constructed labial surface 310b is shown by the dashed line labeled D1. A similar construction of the labial surface 310b in the mesial-distal direction is shown in FIG. 20 where the labial surface 310b is labeled D2.

With reference to the exemplary embodiment shown in FIG. 19, the pad 306 includes a border 316 that generally extends in the lingual direction and tracks with the periphery 314. The border 316 interrupts the tooth-facing surface 312 to define a recessed portion 318 in the tooth-facing surface 312 at the pad 306. Similar to that set forth above, the recessed portion 318 may be textured or processed by such a means as to increase the surface area thereof for bonding the pad 306 to the tooth. For example, in one embodiment, the recessed portion 318 is treated with a laser.

Figure 20:
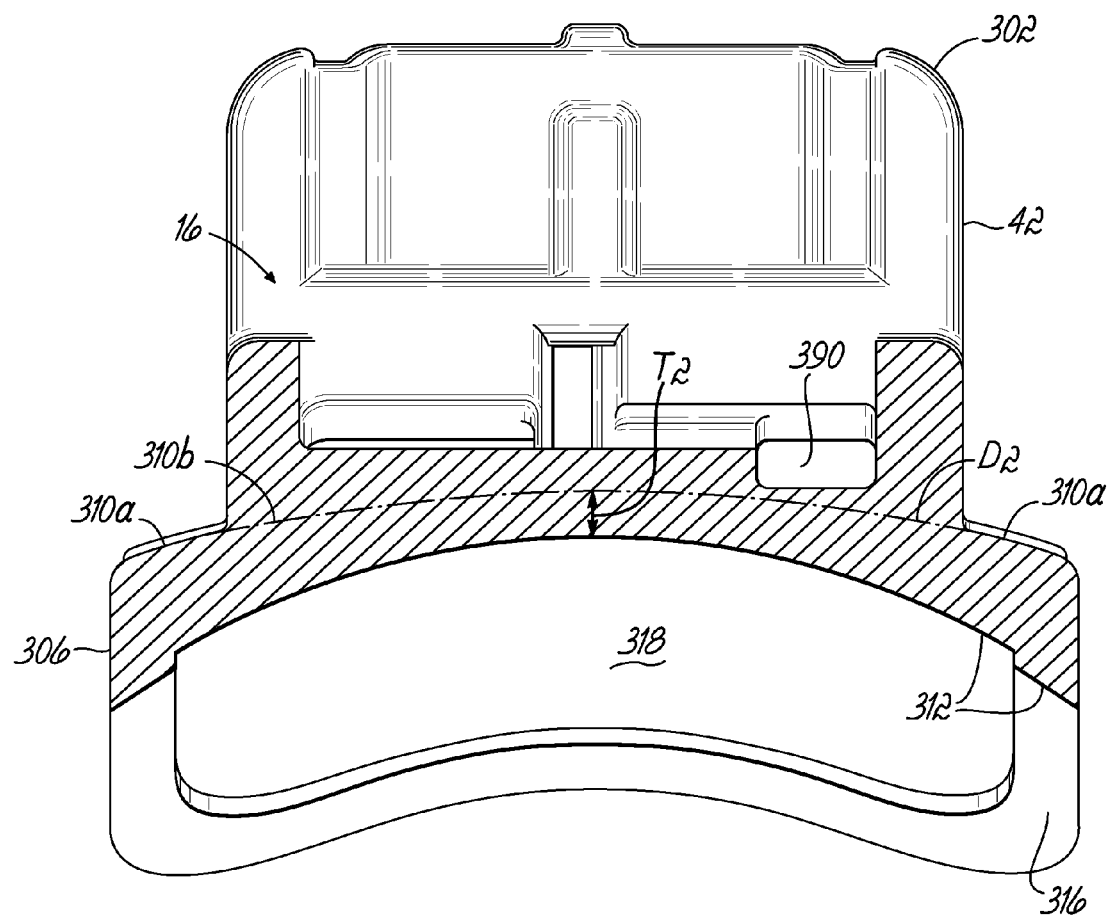
FIG. 20 is a cross-sectional view of the orthodontic bracket shown in FIG. 18 taken along section line 20-20.

As shown in the exemplary embodiment of FIGS. 19 and 20, the pad 306 may vary in thickness across its occlusal-gingival dimension and/or mesial-distal dimension, respectively. Referring to FIG. 19, the tooth-facing surface 312 in the recess 318 may also be shaped generally as an arc, A2. As shown, the arcs A1 and A2 may have different radii of curvature though it will be appreciated that they may have substantially similar radii. By way of example and not limitation, the radius of curvature of A1 in FIG. 19 is greater than the radius of curvature of A2. The thickness, T1, of the pad 306 may then be defined as being the distance from the labial surface 310 (i.e., the visible labial surface 310a or the constructed labial surface 310b according to that described above) to the tooth-facing surface 312 as measured along a line that is perpendicular to a tangent constructed at a point on either of the tooth-facing surface 312 or the labial surface 310a, 310b (i.e., a perpendicular distance between arcs A1 and A2). As such, the perpendicular line intersects both the labial surface 310 and the tooth-facing surface 312.

In FIG. 19, as measured according to the procedure set forth above, the thickness T1 of the pad 306 may be the greatest through the border 316 and then the thickness may decrease by an amount approximately equal to the depth of the recess 318 at locations immediately adjacent the border 316. Along the remaining portion of the tooth-facing surface 312 toward the center region of the bracket 302, the thickness T1 of the pad 306 may gradually decrease. The thickness, T1, may then gradually increase away from the center region toward the opposing side of the pad 306.

Similarly, with reference to FIG. 20, the thickness of the pad 306 in the mesial-distal direction may also be the distance between two arcs constructed by fitting the labial surface 310a, 310b and by fitting the tooth-facing surface 312. Thus the thickness T2, determined in a similar manner as T1, of the pad 306 from the mesial side of the pad 306 to the distal side of the pad 306 may have a similar transition, for example, from being relatively thick, to being relatively thin, and back to being relatively thick. It will be appreciated that it is not necessary that the pad 306 thickness variation in the mesial-distal direction be similar to the thickness variation in the occlusal-gingival direction. For example, the thickness of the pad 306 is one direction, along a mesial-distal or gingival-occlusal cross-sectional plane may be substantially constant but the thickness variation in the other direction, along a gingival-occlusal or mesial-distal cross-sectional plane may vary as set forth above.

With reference to FIG. 18, in one embodiment, the bracket body 302 includes a gingival extension 322, similar to the gingival extension 276 shown in FIG. 9. However, the extension 322 may not extend to or be flush with the gingival periphery of the pad 306. Thus, a portion of the labial surface 310 of the pad 306 is exposed along a gingival portion thereof. The exposed portion may appear as a ledge 330 and provides a reference surface from which to construct the labial surface 310b of the pad 306 from the gingival side to the occlusal side thereof as set forth above with reference to FIG. 19.

Figure 21A:
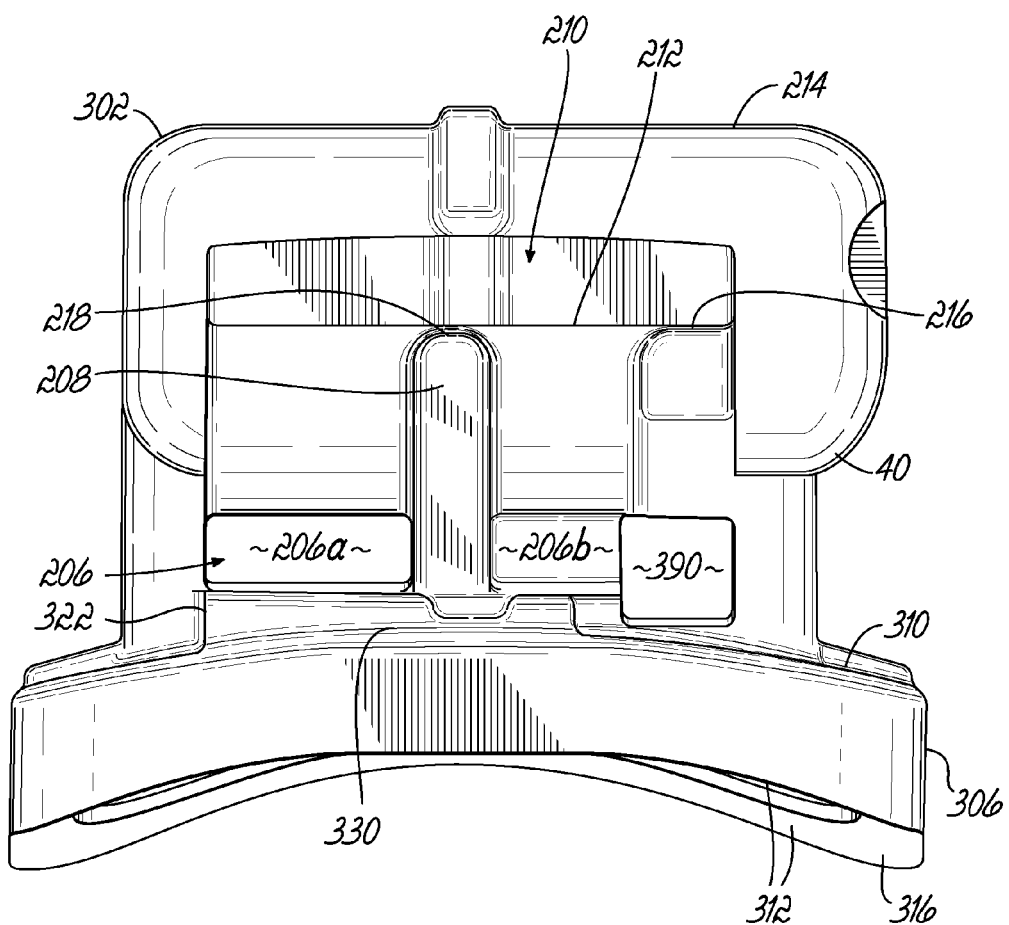
FIG. 21A is a side elevation view of the orthodontic bracket shown in FIG. 18.
Figure 21B:
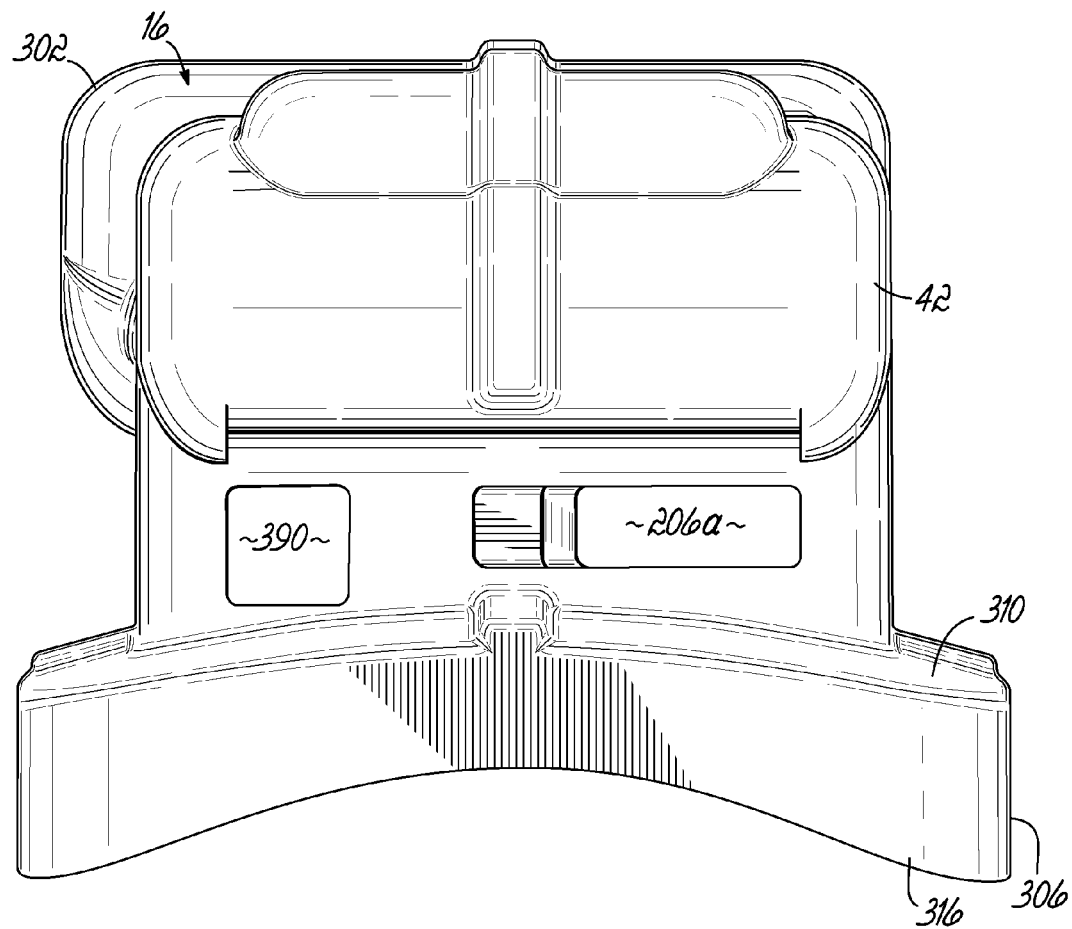
FIG. 21B is a side elevation view of the orthodontic bracket shown in FIG. 18 from the opposite direction of the view shown in FIG. 21A.

The bracket body 302 may further include a bore 390, shown in FIGS. 21A and 21B, that passes through the bracket body 302 and opens to the gingival and occlusal sides thereof. As with the bore 290, the bore 390 is configured to accept an auxiliary device. Further, the bore 390 may have one side or a portion thereof open to the slot 206, for example, slot 206b. It will be appreciated that the thickness variation of the pad 306 may be adjusted such that the pad 306 does not form any portion of the bore 390 as shown in FIGS. 19, 21A, and 21B. The bore 390 may therefore be contained completely within the bracket body 302. This may be accomplished by adjusting the tooth-facing surface 312 and the labial surface 310 of the pad 306 and the thicknesses T1, T2 of the pad 306 to orient the archwire slot 16 in a predetermined location relative to the bracket body 302 while forming the bore 390 within the bracket body 302.

In accordance with an alternative embodiment of the invention and with reference to FIGS. 22-28 in which like reference numerals refer to like features in FIGS. 1-21B, a bracket 400 includes a bracket body 402 and a resilient ligating clip 404 slidably received therein. The bracket body 402 and clip 404 may differ in some respects from the embodiments set forth in FIGS. 1-21B above. These differences will be described below. However, the bracket 400 may be capable of retaining an archwire in the archwire slot 16 in a similar manner as brackets 10, 200, and 300, and the clip 404 may be securable or lockable within the bracket body 402 in at least the closed position, as described above.

Figure 22:
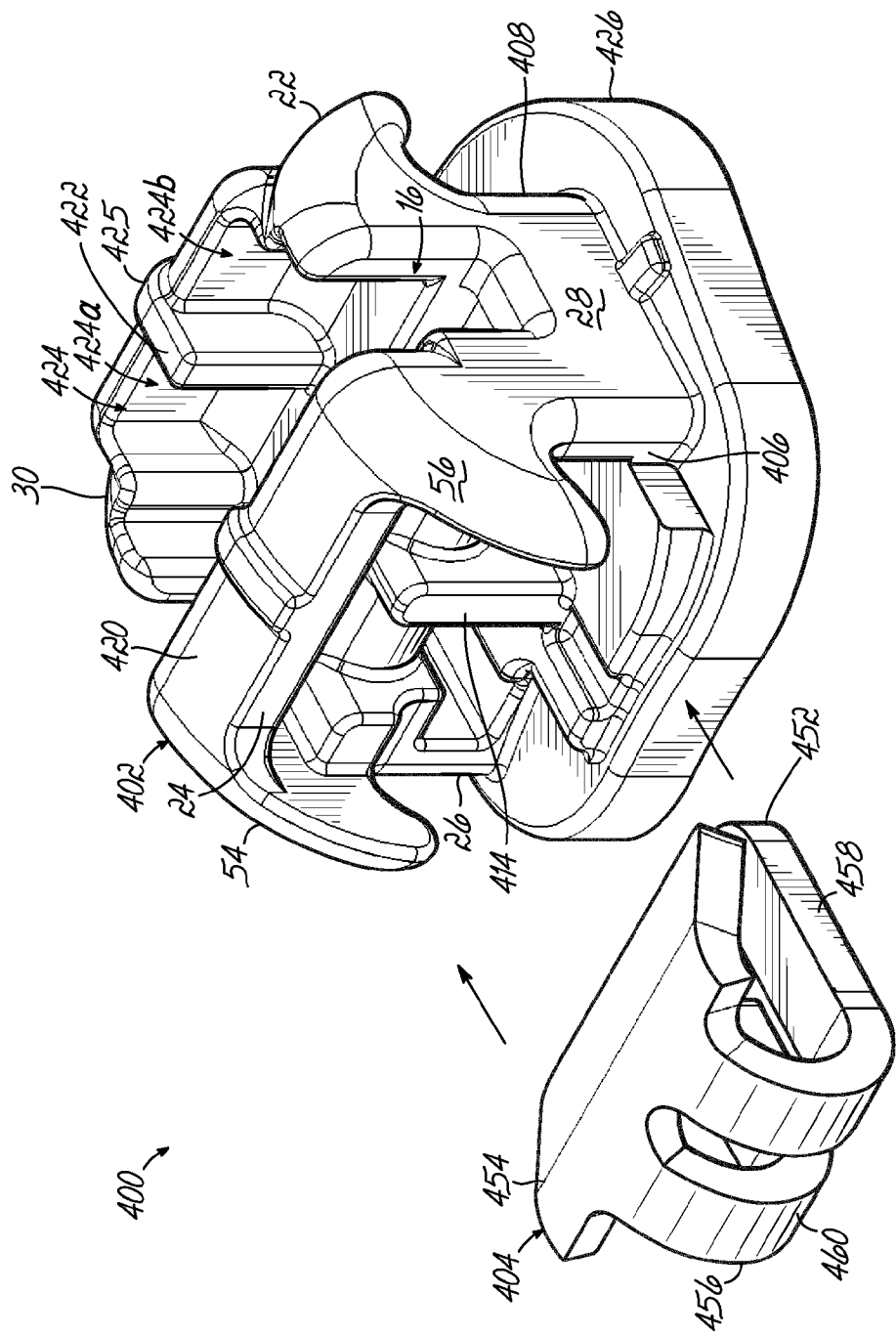
FIG. 22 is a perspective view of a self-ligating orthodontic bracket in accordance with another embodiment of the invention with a resilient ligating clip removed from the body.
Figure 23:
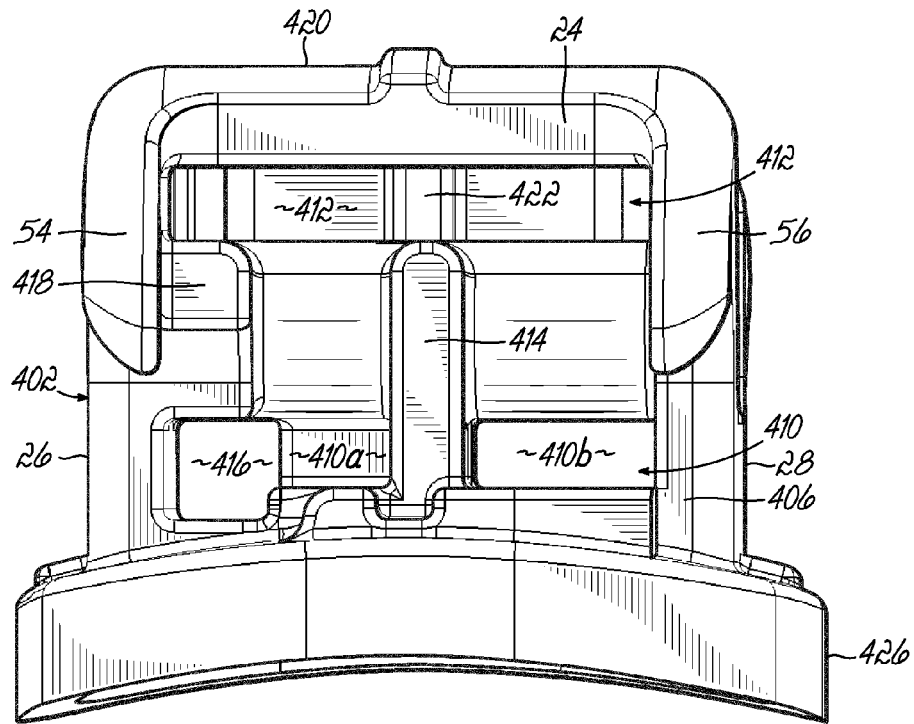
FIG. 23 is a side elevation view of the bracket body shown in FIG. 22.
Figure 24:
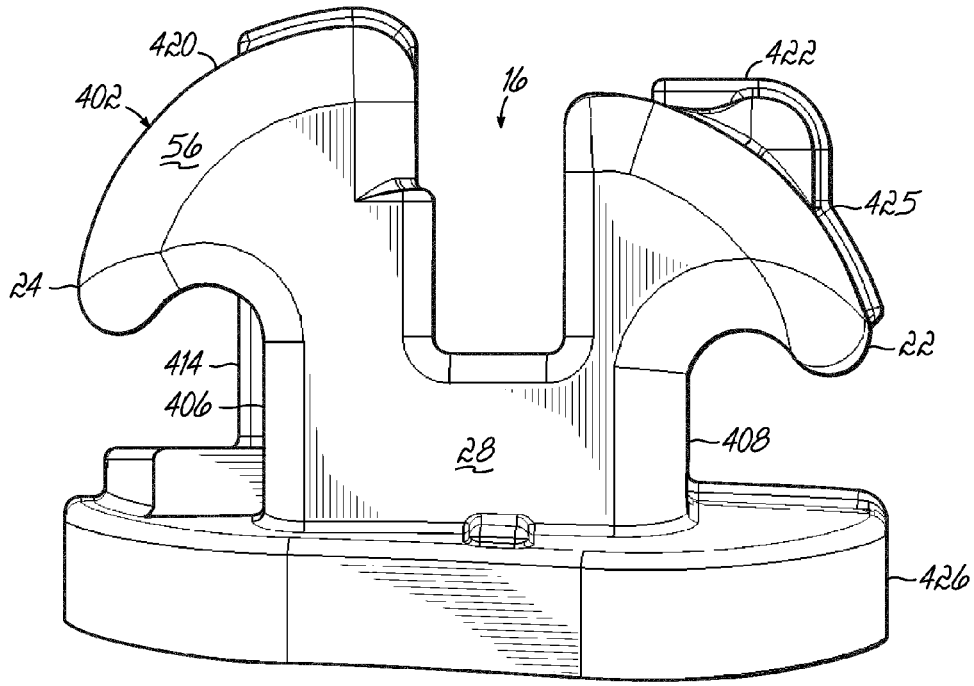
FIG. 24 is another side elevation view of the bracket body shown in FIG. 22.

With reference generally to FIGS. 22, 23, and 24, the bracket body 402 includes gingival and occlusal body portions 406, 408 that are separated by the archwire slot 16. In the exemplary embodiment depicted and with reference specifically to FIGS. 23 and 24, the body portions 406, 408 collectively include a lingual slot 410, and the body portion 406 additionally includes a labial slot 412, all similar to those disclosed above, for example, slots 410 and 412 are similar in function to slots 206 and 210, respectively. In this regard, the slot 410 is divided by a support 414 into mesial and distal portions 410a, 410b. As shown in FIG. 23, the relative positions of the support 414 and slots 410 and 412 may be different from those described above. For example, the features of the bracket body 402 may be located on the opposing side as compared bracket bodies disclosed above. Specifically, and by way of example and not limitation, the portions 410a, 410b may be located toward the distal side 28 of the bracket body 402 rather than the mesial side 26 of the bracket body as is shown for example in FIG. 11A. Further in this regard, the bracket body 402 may include a gingival-occlusal extending bore 416. Although, as shown, the bore 416 may be located on the mesial side 26 of the bracket body 402 rather than the distal side 28, as shown in FIG. 11A. Other features may also be similarly relocated. For example, in one embodiment, a clip stop 418, similar to, for example, clip stop 216, may be located against the mesial guide 54 rather than against distal guide 56. It will be appreciated that the arrangement of, for example, the slots 410, 412 and the support 414 and/or the bore 416 may depend upon the particular tooth for which the bracket 400 is intended to be used such that the bracket 400 may function similar to brackets 10, 200, and/or 300 described above.

Figure 26:
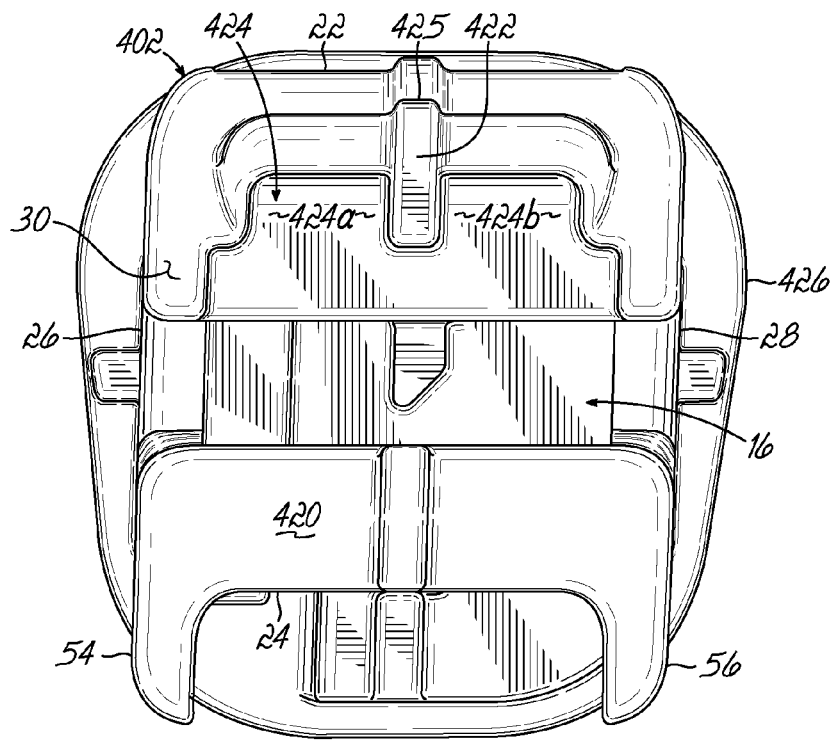
FIG. 26 is a plan view of the bracket body shown in FIG. 22.

In addition, and with reference to FIGS. 22, 23, and 26, the body portion 406 may include a bridge 420 extending mesial-distally across the portion 406. The bridge 420 depicted may have a different configuration than other bridges disclosed herein. Generally, the configuration of the bridge 420 may ease access to the clip 404 where such access is desired. For example, there may be tooth positions where facilitating access to the clip 404 or to the gingival side 24 of body 402 generally is advantageous, such as, to speed installation of an archwire at locations where access is limited. Specifically, for example, unlike the bridge 214 shown in FIG. 10, the bridge 420 is relatively narrow. By reducing the gingival-occlusal width of the bridge 420, the clip 404 may be more easily accessed. For instance, a clinician may prefer to move the clip 404 to the closed position with one finger while holding an archwire in the archwire slot 16. Reducing the width of the bridge 420 may allow a clinician's finger to more-fully contact the clip 404 during the entire movement of the clip 404 to the closed position. That is, the clinician may be better able to seat the clip 404 in the closed position with their finger, as opposed to using a tool, with this configuration. In this manner, the clinician may better feel, as opposed to hear, the clip 404 lock in the closed position, though it will be appreciated that the clinician may both feel and hear the clip 404 lock into the closed position.

With reference to FIGS. 22, 24, and 26, other differences between the bracket body 402 and previous bracket bodies, may include an internal rib 422. As shown, the internal rib 422 may divide a tool receptacle 424 into mesial and distal receptacles 424a, 424b. Thus, the function of the rib 422 may be similar to the rib 86, shown in FIG. 1. The rib 422 may, however, extend to near the labial side 30 of the bracket body 402. For example, the rib 422 may be flush with the labial side 30 and form a portion thereof. In one embodiment, as shown in FIGS. 22 and 24, the rib 422 is flush and forms a surface portion or an extension of an alignment marker 425.

It will be appreciated that the labial height of the rib 422 as compared to rib 86, which lies below or recessed from the labial side 30 of the bracket body 12 of FIG. 1, may be advantageous. For example, the extended rib 422 may prohibit debris and foreign objects from entering the tool receptacle 424 and becoming lodged therein or inadvertently releasing the clip 404 from a secured, closed position. By way of further example, the rib 422 may be additionally advantageous when the bracket 400 is used on a specific tooth in the mouth. For example, when the bracket 400 is mounted to an anterior tooth, which may be more easily accessible to the patient, the rib 422 may prevent the patient from inserting a fingernail into the tool receptacle 424 and inadvertently or intentionally moving the clip 404 to an opened position, which may release the archwire 16. In other words, it may prevent a patient, such as, a child, from absentmindedly playing with the bracket 400 by opening and closing the clip 404, and possibly damaging or destroying the clip 404 or a portion of the bracket body 402 in the process.

Figure 25:
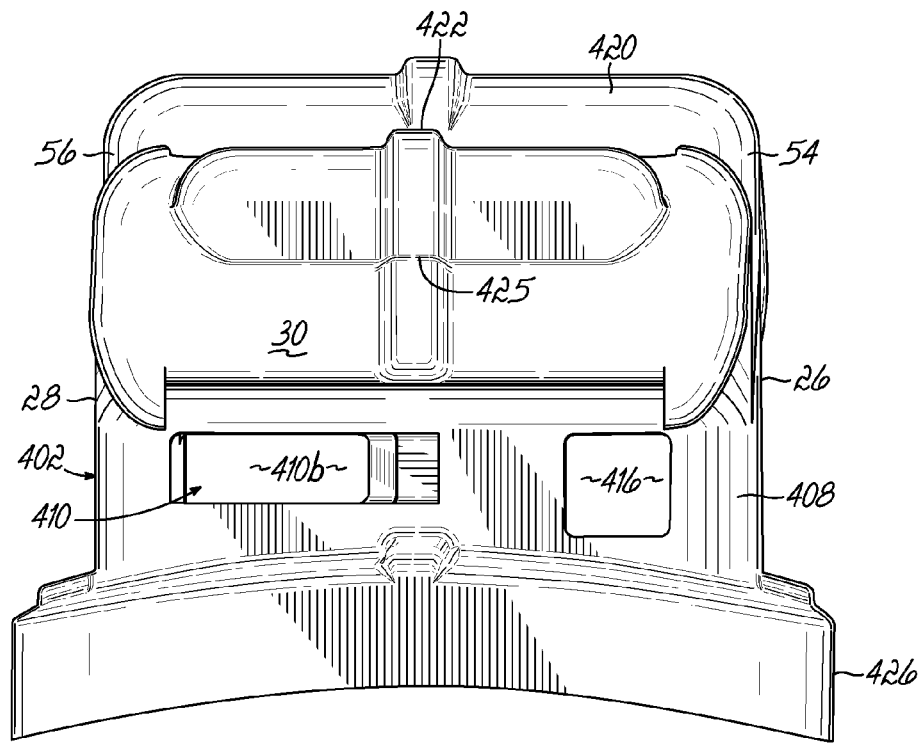
FIG. 25 is another side elevation view of the bracket body shown in FIG. 22.

Additionally, the bracket 400 may include a pad 426, which may be similar to other pads disclosed herein. With reference to FIGS. 23-25, the pad 426 may be more uniformly thick as compared to the pad 306 shown in FIG. 20, for example. In this regard, the configuration of the pad 426 may depend on the specific tooth to which the bracket 400 is to be bonded. For example, the curvature of the pad 426 may depend on the "in-out," among other possible prescription variables, of the bracket for that location. Thus, the specific design of pad 426 may vary and may include one or more features of the pads 32, 270, 306 or other features that depend on the specific patient.

Figure 27:
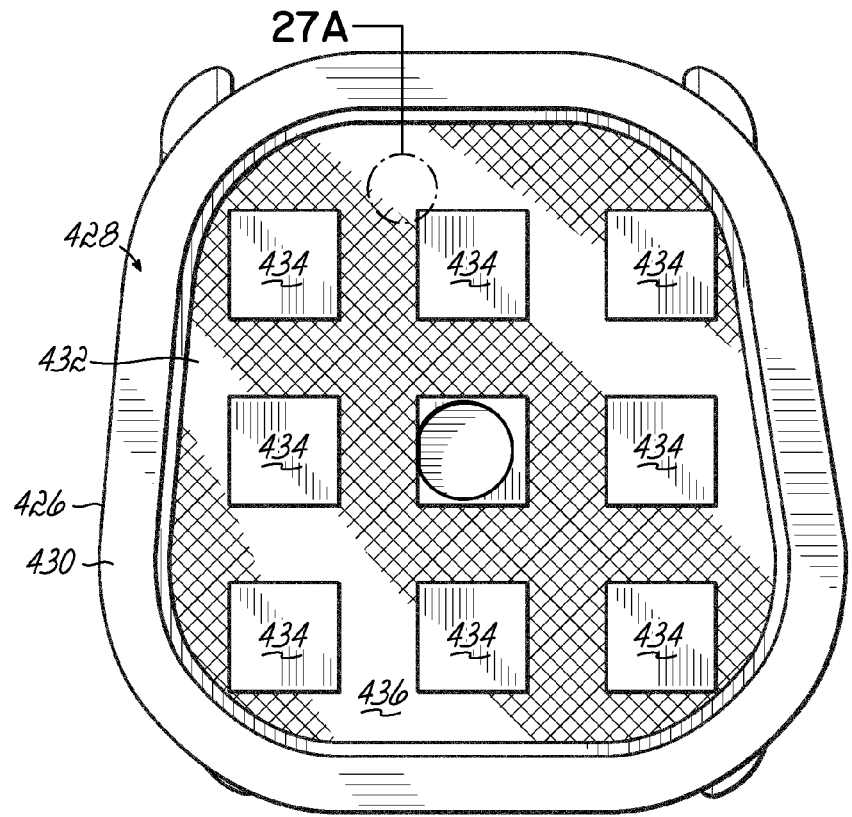
FIG. 27 is another plan view of the bracket body shown in FIG. 22.

With continued reference to the exemplary embodiment shown in FIG. 27, the pad 426 includes a tooth-facing surface 428, which may be non-planar. For example, as shown, the tooth-facing surface 428 may include a border 430, which may be similar to border 316, shown in FIG. 20. The border 430 may encircle a recessed portion 432 which may include surfaces that are distanced from the tooth surface when the bracket 400 is bonded thereto. Thus, the recessed portion 432 may define a space when the bracket 400 is bonded to the tooth. The space may be filled with an adhesive or cement material for securing the bracket body 402 to the tooth.

Furthermore, as shown in FIG. 27, the recessed portion 432 may define one or more pegs 434. By way of example, the peg 434 may have an orthogonal periphery, for example, a square periphery, though the periphery is not limited thereto as other peripheries (e.g., round, triangular, irregular etc.) are also contemplated. In addition, when there are multiple pegs 434, each may have the same periphery, though each may be different. The peg 434 may extend to the same lingual plane as the border 430 such that the void space formed in conjunction with the tooth surface may be formed by the border 430 and one or more pegs 434 and the tooth surface.

In addition, the recessed portion 432 may further include a treated surface 436. As introduced above, a laser or other stream of energy may be used to roughen portions of the pad 426 during the manufacturing process thereof. In this instance, the pad 426 and possibly the bracket body 402 may be formed by an injection molding process. This may be, for example, a CIM operation or a MIM operation as are known in the art and set forth above. Such processes produce green bodies, which are generally solid shapes made of ceramic or metal particles held together by a binder. The binder is generally an organic compound, such as, a thermoplastic polymer.

Briefly, this process may include injecting a heated mixture of the particles and binder into a mold. Following cooling, the mixture hardens sufficiently to be handled. The shaped, cooled mixture may be referred to as a "green body" or an "unsintered body" or being in the "green state." Subsequent processing, including a sintering process, removes the binder and produces a final product. In this regard and in one embodiment of the invention, during the manufacturing of the pad 426 and while the pad 426 is in the green-state, the tooth-facing surface 428 may be exposed to a laser beam or other energy source.

Further, in this regard, according to one embodiment of the invention, a laser beam may be scanned over a portion of the tooth-facing surface 428 while it is in the green state. This may be referred to as "laser etching." Exemplary lasers capable of producing the laser beam include those made by Videojet of Wood Dale, Ill., and KEYENCE Corporation of America of Itasca, Ill. Scanning may include exposing selected portions of the surface 428 when in the green state to the laser beam to produce the treated surface 436. Exposure of the tooth-facing surface 428 of the pad 426 in the green-state to a laser beam may result in melting, vaporizing, and/or burning of the binder exposed without significantly melting or point sintering the particles. As a result, surface particles in regions in which the binder is melted, vaporized, and/or burned are removed. Particles not originally exposed and which may initially reside in the interior of the green body are then exposed by the removing process.

Figure 27A:
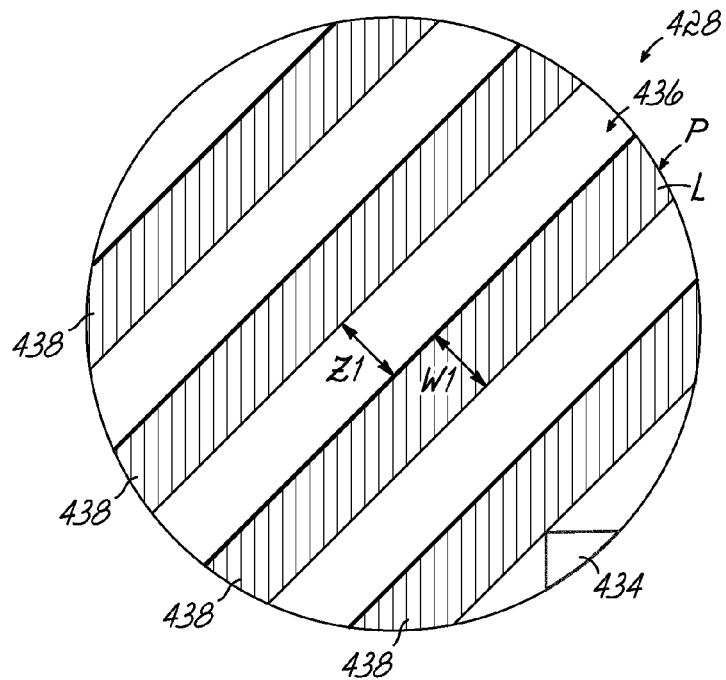
FIG. 27A is an enlarge view of the encircled area 27A in FIG. 27 with a representation of a pattern used during manufacturing of the orthodontic bracket.

By way of example, and with reference to FIGS. 27 and 27A, the selected portions of the surface 428 may be configured as a first set of individual lines 438 that may be arranged in a pattern, P, which at least partly defines the border 430 and/or the peg 434 in the pad 426. Multiple patterns may be utilized to define the border 430 and/or the peg 434. In addition, while a "line" is referred to herein, it will be appreciated that the line has width W1 as well as length such that scanning the laser beam along the line, L, includes exposing a predefined area of the tooth-facing surface 428 to the laser beam.

The arrangement of the lines in the pattern may determine the desired surface features of the treated surface 436. In one embodiment, the predetermined lines, L, in the pattern, P, may not overlap as shown in FIG. 27A. That is, the treated surface 436 may be configured such that the adjacent lines in the first set of lines 438 do not overlap. This may include placing a preselected distance or land width, Z1, between the lines 438. For example, as shown in FIG. 27A, the pattern may include parallel lines spaced apart by up to about 0.020 inches and by way of further example, may be spaced apart from about 0.001" to about 0.015" and from about 0.005" to about 0.012". As such, the lines of the laser beam exposed material may be separated by an amount that approximates the land width Z1.

Figure 27B:
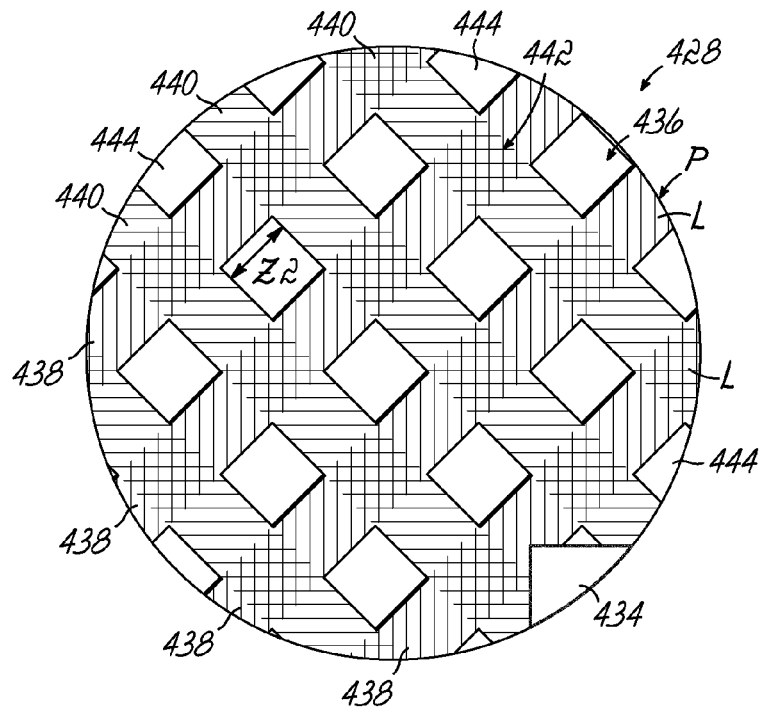
FIG. 27B is an enlarged view of the encircled area 27A in FIG. 27 with another representation of a pattern used during manufacturing of the orthodontic bracket.
Figure 27C:
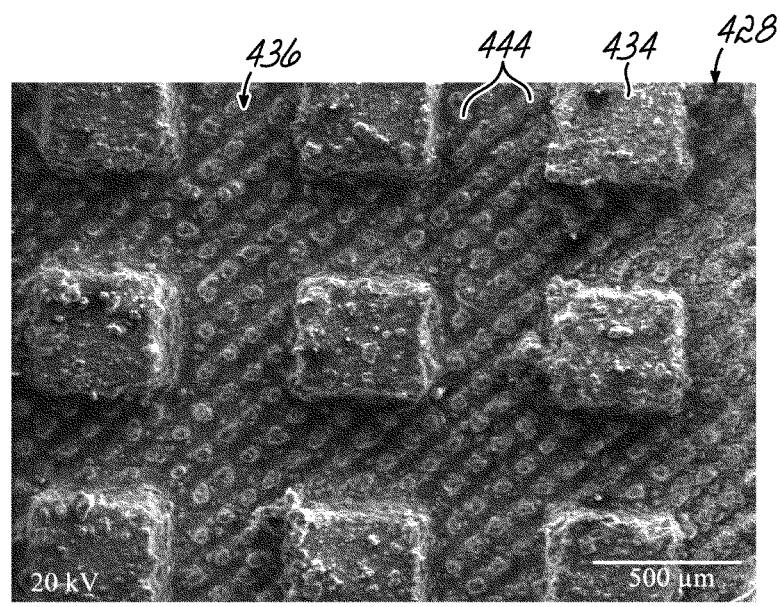
FIG. 27C is a Scanning Electron Microscope (SEM) micrograph depicting a magnified view of the pad after treatment according to one embodiment of the invention.

Further, with reference to FIG. 27B, the pattern P may further include a second set of lines 440 that are transverse to the first set of lines 438. In one embodiment, the second set of lines 440 is nearly perpendicular to the first set of lines 438 though embodiments of the present invention are not limited to perpendicular. While two sets of lines 438, 440 are shown and described, it will be appreciated that the pattern P may include multiple additional sets of lines. As with the first set of lines 438, the individual lines in the second set of lines 440 may be spaced apart from one another such that they do not overlap one another. Accordingly, a width or land of material, Z2, of unexposed material may separate the individual lines in the second set from one another. Portions of the exposed material of the second set of lines 440 may, however, overlap the exposed material of the first set of lines 438. Overlap between the first set of lines 438 and the second set of lines 440 is shown by way of example at arrow 442. The particles found in area of the tooth-facing surface 428 exposed according to the first and second sets of lines 438, 440 are removed to expose other particles underneath the removed particles. FIG. 27C depicts an exemplary treated surface on a pad in the green state.

With continued reference to FIG. 27B, the regions of the tooth-facing surface 428 which remain after removal of material may appear as a plurality of posts 444. By way of example only, the posts 444 may appear as stalagmite-type structures or other columnar-type structures. It will be appreciated that the configuration of the posts 444 may depend on the land width Z1, Z2 between the lines in the first set of lines 438 and/or the second set of lines 440, respectively. However, the posts 444 are many times smaller than the pegs 434 (for example, as shown in FIG. 27C). By way of example only, the peg 434, when present, may be at least about 5 times the size of any single post 444, and by way of additional example, the peg 434 may be at least about 8 times or at least about 10 times the size of any single post 444.

Figure 28:
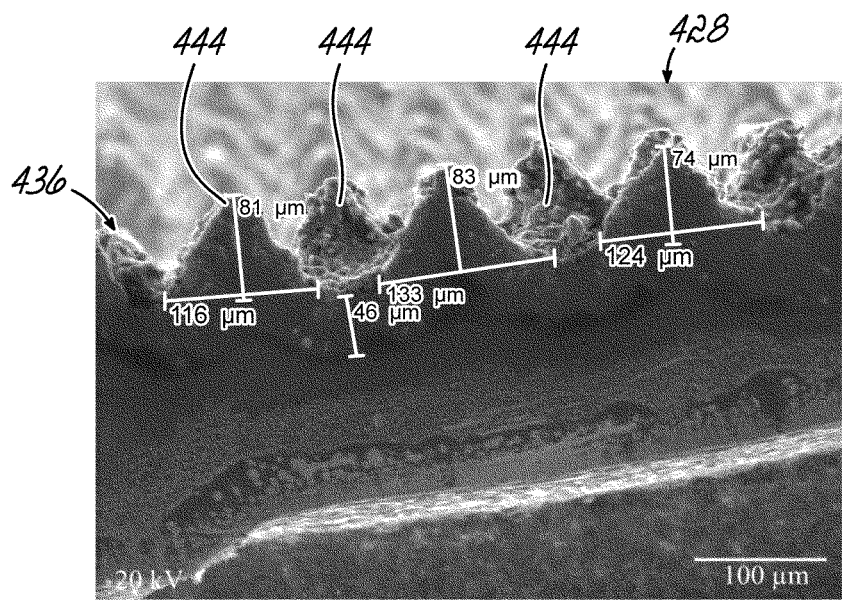
FIG. 28 is a SEM micrograph depicting a magnified view of a cross section of a pad after treatment according to one embodiment of the invention.

The exemplary posts 444, shown for example in FIG. 28, have a cone-shaped columnar structure. The dimensions of the posts 444 may be, for example, between about 100 µm and about 140 µm at the base and between about 70 µm and about 90 µm in height, though embodiments of the invention are not so limited as other dimensions of posts 444 may be suitable. By way of specific example, the posts 444 shown in FIG. 28 measure about 116 µm, about 133 µm, and about 124 µm in width at the base thereof. The posts 444 measure 81 µm, 83 µm, and 124 µm, respectively, in height.

In one embodiment, following treating the tooth-facing surface 428 in the green, unsintered state by exposing the surface to a laser beam to create treated surface 436, as set forth above, the pad 426 and bracket body 402, where applicable, may be subject to a de-binding process whereby the binder is removed. The de-binding process may include heating the green body to a temperature sufficient to decompose the binder as is known in the art. Following de-binding, a sintering process may be used to produce the pad 426. Sintering processes are known in the art and may include heating the de-bonded pad to a temperature sufficient to cause diffusion between the particles in the body. Generally, sintering may cause a decrease in the dimensions and is generally accompanied by an increase in density of the part.

In one embodiment, following de-binding and sintering, where applicable, the sintered pads and/or bracket bodies may be subject to one or more finishing operations. As is known, finishing operations generally include those that improve the aesthetic appearance of the parts. One finishing operation that may be utilized in the manufacturing of orthodontic brackets, particularly metallic orthodontic brackets, is tumbling. Tumbling may be utilized to remove residue from the surfaces of the brackets and may deform the posts 44 by impact between the media and posts 444. That is, tumbling may make the brackets shiny. In this regard, tumbling may include the use of tacks or tumbling media, water, and pumice that, together with the brackets, are introduced into a tumbling apparatus. Such apparatuses may include those that rotate or roll, such as, a barrel, to cause the brackets and other media to move relative to one another. By way of example, rotating a barrel containing the brackets of 17-4 stainless steel and media, as set out above, at about 185 rpm for 15 minutes polishes the brackets and results in an improved, more aesthetic appearance.

In one embodiment, the tumbling operation may further include one or more additional processes, for example, cleaning and burnishing the brackets. In this regard, a chemical polishing agent may replace the pumice introduced in the tumbling operation described above, for example, Chemcid 2509 from Chemetall Americas of New Providence, N.J., may be used to in one or both of the cleaning and burnishing operation.

Figure 29A:
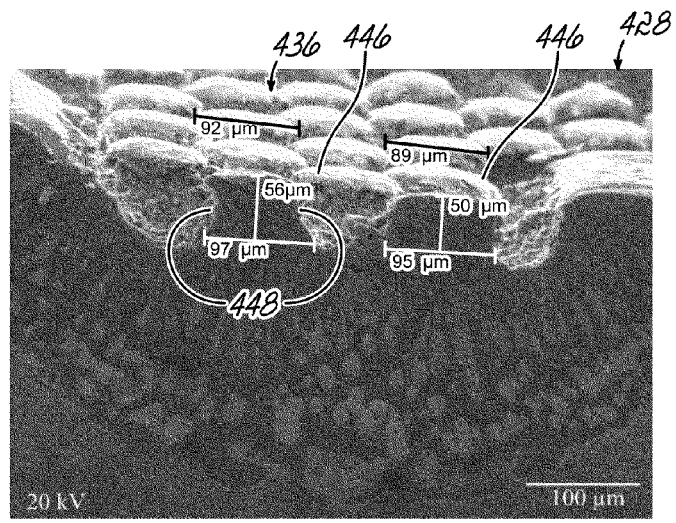
FIG. 29A is a SEM micrograph depicting a magnified view of a cross section of a pad after treatment according to one embodiment of the invention.
Figure 29B:
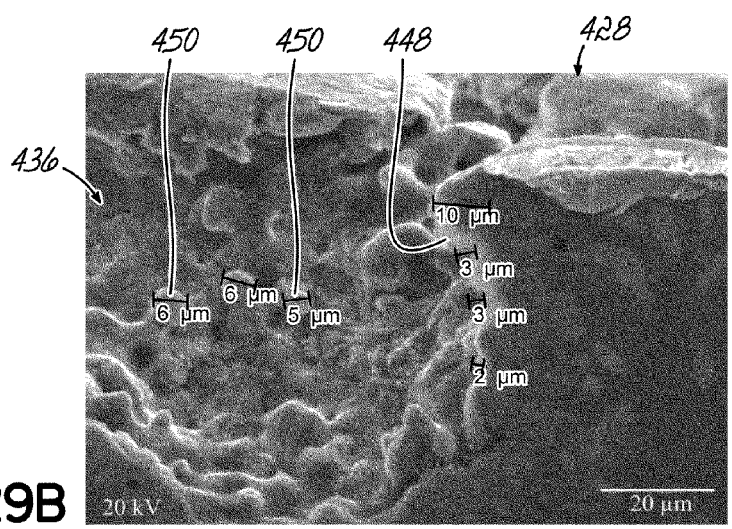
FIG. 29B is a SEM micrograph depicting a magnified view of an area depicted in FIG. 29A.

With reference to FIGS. 29A and 29B, the posts 444 produced during the surface treatment described above may be deformed, such as by tumbling. As shown in FIG. 29A, the deformation of the posts 444 may result in mushroom-like structures 446. The structures 446 may measure roughly the same along the base dimension as the posts 444 disclosed above. However, the height of the structures 446 may be less than the posts 444 by between about 10% and about 80%, and by way of additional example, between about 30% and about 60%. The height of the structures 446 may measure between about 40 µm and about 70 µm, though it will be appreciated that the height of the structures 446 is dependent on the height of the posts 444. Furthermore, the top-most dimension of the structures 446 may measure or be greater than or less than the base dimensions set out above. By way of example, the structures 446 may measure between about 70 µm and about 120 µm though this dimension will depend on the pattern P used to remove unsintered material from the tooth-facing surface 428.

Figure 29C:
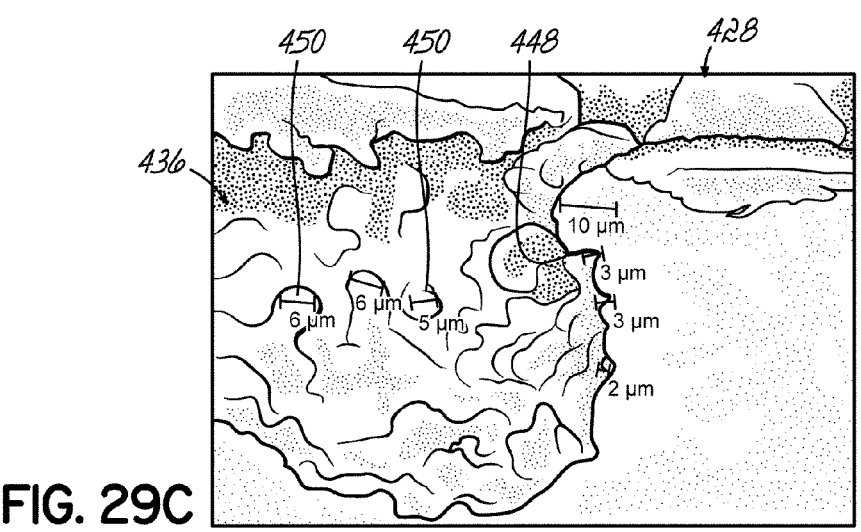
FIG. 29C is an illustration of the microstructure of FIG. 29B.

With continued reference to FIGS. 29A and 29B, the structures 446 may include undercuts 448 (shown best in FIGS. 29B and 29C). Not being bound by theory, the undercuts 448 may be the result of deforming the posts 444. In one embodiment, one or more of the finishing operations, set forth above, are configured to deform the posts 444 after sintering, though embodiments of the present invention are not so limited. The undercuts 448 may measure between about 3 µm and about 10 µm deep from the outermost edge of the structure 446 to the narrowest portion of the structure 446. The undercut 448 may be positioned proximate the surface nearest to the tooth surface when the pad is installed thereon. However, the undercut 448 may be positioned between about 10 µm and about 40 µm from the surface nearest to the tooth surface.

In addition, the treated surface 436 may include a plurality of microscopic features 450. The microscopic features 450 may be at least about 20% smaller than the structures 446, though the microscopic features 450 may measure at most about 10% of the size of the structures 446. By way of further example, the microscopic features 450 may measure on the order of the same size as the particles mixed with the binder, as described above, or slightly (about 10% to about 20%) smaller due to the laser treatment and/or sintering operation. By way of example, the microscopic features 450 may measure between about 1 µm and about 15 µm. As shown in FIG. 29B, the microscopic features 450 may measure about 2 µm, about 3 µm, about 5 µm, about 6 µm, and about 10 µm. It will be appreciated that the structures 446 and/or the microscopic features 450 may enhance the bonding of the pad 426 with the tooth surface by increasing the surface area for bonding to the bracket. Moreover, it will also be appreciated that the undercuts 448 may also enhance the bonding with the tooth surface and that each of the features may be controlled by changing the pattern P on the treated surface 436. In one embodiment, the pattern on the treated surface 436 depends on the tooth surface to which the pad 426 is to be bonded. Particular patterns may tailor the surface bonding characteristics of the pad to a specific tooth. Advantageously, the pattern allows the pad to be customized for a tooth and/or patient.

Figure 30:
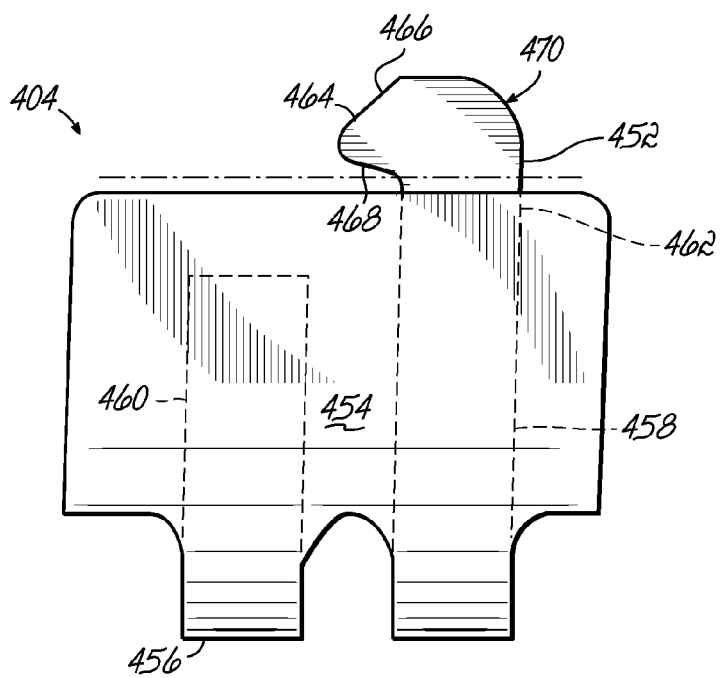
FIG. 30 is a plan view of the clip shown in FIG. 22.

With reference to FIGS. 22 and 30, the clip 404 may be similar to the clips 14, 204, and 304 in one respect or another. For example, similar to clips 204 and 304, clip 404 is configured to slidably engage the slots in the bracket body. As shown in the FIG. 22, the clip 404 is configured to engage slots 410, 412 in the bracket body 402. In this regard, the clip 404 may be similarly shaped, for example, with a lingual clip portion 452 and a labial clip portion 454 extending from a gingival clip portion 456 as well as including other features described above in whole or in part.

The bracket 400 may include a securing mechanism similar to the securing mechanism 246, described above. As such, the bracket 400 may include a receiving member that cooperates with a locking member. With reference to FIGS. 22 and 30, a locking member 470 may be associated with or be formed in the ligating clip 404. In this regard and in one embodiment, the lingual clip portion 452 and the gingival clip portion 456 may include an L-shaped projection 458 and an alignment member 460 (shown in phantom line) each having similar function as the projections and alignment members set out above. With reference to FIG. 30, the projection 458 has similar functions as set forth above with regard to, for example, projection 226 of FIG. 13B. In this regard, the projection 458 may include a first leg 462 and a second leg 464 extending transverse to the first leg 462. Further, the first leg 462 may include a first surface 466 and a second surface 468. Each of the surfaces 466, 468 may contact the bracket body 402 in a similar manner as set forth above such that the clip 404, when moved to the closed position and from the closed position, contact the bracket body 402. Although not shown, rather than having the projection 458 and the alignment member 460 arranged as shown, the clip 404 may include two projections 458. That is, a second projection (not shown would replace the alignment member 460. This may be particularly advantageous for a bracket to be used on a molar tooth.

As shown in FIG. 30 and introduced above, the first surface 466 and the second surface 468 may contact surfaces of a receiving member (not shown) of the bracket body 402 to allow the clip 404 to be secured in at least the closed position. The configuration of the first surface 466 and/or the second surface 468 may be changed to increase or reduce the force required to close and/or open the clip 404, respectively. Specifically, as shown in FIG. 30, the second surface 468 may be tapered relative to a normal constructed at the intersection of the first leg 462. It will be appreciated that tapering the second surface 468 in this direction may reduce the force required to open the clip 404 from the closed position.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. The various features of the invention may be used alone or in any combinations depending on the needs and preferences of the user.

What is claimed is:

1. An orthodontic bracket for coupling an archwire with a tooth, comprising:
    a bracket body adapted to be mounted to the tooth and including:
        an archwire slot adapted to receive the archwire therein and including a base surface and two opposing side walls extending away from the base surface;
        a clip slot extending centrally through the bracket body transversely to the archwire slot;
        a first body portion; and
        a second body portion opposing the first body portion and being separated therefrom by the archwire slot, the first body portion including a support surface that is open to the archwire slot; and
    a resilient ligating clip that is slidably engageable with the support surface and the clip slot, the resilient ligating clip comprising a first clip portion and a second clip portion that extend generally in the same direction from a third clip portion, the resilient ligating clip being movable relative to the bracket body between an opened position and a closed position in which a portion of the archwire slot is between the first clip portion and the second clip portion, and the third clip portion is adjacent the support surface,
    wherein the first body portion further includes a mesial-distal bridge that at least partially covers the support surface and the first clip portion is configured to contact the mesial-distal bridge when the first clip portion is deflected away from the base surface.

2. The orthodontic bracket of claim 1, wherein the first clip portion includes a free end portion and the bracket body is configured to limit deflection of the first clip portion away from the base surface without contacting the free end portion.

3. The orthodontic bracket of claim 1, wherein the resilient ligating clip is configured to contact the bracket body by flexing in a direction opposite to deflection of the first clip portion away from the base surface.

4. The orthodontic bracket of claim 1, wherein the bracket body further includes a clip stop surface extending from the first body portion and one of the first clip portion and the third clip portion further includes a shoulder configured to be in near-contact relation with the clip stop surface when the resilient ligating clip is in the closed position and being configured to contact the clip stop surface when the first clip portion is deflected away from the base surface.

5. The orthodontic bracket of claim 1, wherein the mesial-distal bridge forms a fulcrum when the first clip portion is deflected away from the base surface and by which additional deflection of the first clip portion away from the base surface causes an increase in resistance to deflection of the first clip portion.

6. The orthodontic bracket of claim 1, further comprising:
a securing mechanism configured to secure the resilient ligating clip in the closed position and including a locking member forming a portion of one of the bracket body and the second clip portion and a receiving member forming a portion of the other of the bracket body and the second clip portion, the locking member configured to engage the receiving member when the resilient ligating clip moves toward the opened position from the closed position.

7. The orthodontic bracket of claim 6, wherein the locking member is configured to flex in a plane of the second clip portion when the resilient ligating clip is moved from the opened position to the closed position.

8. The orthodontic bracket of claim 6, wherein the resilient ligating clip further includes an alignment member configured to guide the resilient ligating clip between the opened position and the closed position and the locking member is configured to deflect toward the alignment member when the resilient ligating clip is between the opened position and the closed position.

9. The orthodontic bracket of claim 6, wherein the locking member has a leading surface that is configured to contact the bracket body during movement of the resilient ligating clip from the opened position to the closed position to cause the locking member to deflect.

10. The orthodontic bracket of claim 6, wherein the locking member is associated with the second clip portion and the receiving member is associated with the bracket body.

11. The orthodontic bracket of claim 1, wherein the second body portion includes a clip receptacle for receiving a free end portion of the first clip portion when the resilient ligating clip is in the closed position, and wherein the clip receptacle does not prevent movement of the first clip portion away from the base surface.

12. The orthodontic bracket of claim 11, wherein the second body portion includes a tool receptacle proximate the clip receptacle that is adapted to receive the end of a tool for forcibly engaging the resilient ligating clip when the resilient liqatinq clip is in the closed position.

13. The orthodontic bracket of claim 12, wherein the tool receptacle is divided by an internal rib that is flush with an outer surface of the bracket body.

14. The orthodontic bracket of claim 1, wherein the bracket body further includes a bore that extends through the bracket body and is oriented transverse to the archwire slot.

15. The orthodontic bracket of claim 14, wherein the resilient ligating clip is configured to form at least a portion of one sidewall of the bore when the resilient ligating clip is inserted into the clip slot.

16. The orthodontic bracket of claim 1, wherein the first portion of the resilient ligating clip has an inwardly-facing surface opposing an outwardly-facing surface and when the resilient ligating clip is in the closed position the inwardly-facing surface of the first clip portion faces the base surface, wherein deflection of the resilient ligating clip away from the base surface is limited by contact between the bracket body on the body portion that includes the support surface and the outwardly-facing surface of at least one of the first clip portion and the third clip portion.

17. An orthodontic bracket for coupling an archwire with a tooth, comprising:
a bracket body adapted to be mounted to the tooth and including an archwire slot adapted to receive the archwire therein and a clip slot extending transverse to the archwire slot centrally through the bracket body between the archwire slot and the tooth when the orthodontic bracket is placed on the tooth;
a resilient ligating clip that is slidably engageable with the bracket body in the clip slot and including a first clip portion and a second clip portion extending generally in the same direction from a third clip portion, the resilient ligating clip being movable relative to the bracket body between an opened position and a closed position in which the first clip portion covers the archwire slot and the second clip portion resides in the clip slot; and
a securing mechanism configured to secure the resilient ligating clip in the closed position and including a locking member forming a portion of one of the bracket body or the second clip portion and a receiving member forming a portion of the other of the bracket body or the second clip portion, the locking member and the receiving member configured to cooperate to form an interference fit therebetween when the resilient ligating clip moves from the closed position toward the opened position,
wherein the locking member is associated with the second clip portion and the receiving member is associated with the bracket body.

18. The orthodontic bracket of claim 17, wherein the locking member includes a first leg substantially perpendicular to a second leg, the first leg being configured to flex when the resilient ligating clip is moved to the closed position in which the second leg is configured to form the interference fit with the receiving member when the resilient ligating clip is moved toward the opened position from the closed position.

19. The orthodontic bracket of claim 18, wherein the second leg lies in substantially the same plane as the second clip portion.

20. The orthodontic bracket of claim 18, wherein the resilient ligating clip further comprises an alignment member that is configured to guide movement of the resilient ligating clip from the opened position to the closed position.

21. The orthodontic bracket of claim 17, wherein the locking member flexes in a plane of the second clip portion.

22. The orthodontic bracket of claim 17, wherein the bracket body further includes a first body portion and a second body portion that are separated by the archwire slot, one of the first body portion and the second body portion including a support surface open to the archwire slot; and a mesial-distal bridge that covers a portion of the support surface and the resilient ligating clip being configured to be in near-contact relation with the mesial-distal bridge when the resilient ligating clip is in the closed position, such that deflection of the first clip portion away from the archwire slot causes contact between the first clip portion and the mesial-distal bridge.

23. The orthodontic bracket of claim 22, wherein the bracket body further includes a clip stop surface extending from the first body portion or the second body portion that includes the support surface in a direction away from the archwire slot, and wherein the resilient ligating clip further includes a shoulder in one of the first clip portion or the third clip portion that is configured to be in near-contact relation with the clip stop surface when the resilient ligating clip is in the closed position such that deflection of the first clip portion away from the archwire slot causes contact between the mesial-distal bridge and the first clip portion and between the clip stop surface and the shoulder.

24. The orthodontic bracket of claim 22, wherein the body portion that does not include the support surface includes a clip receptacle for receiving a free end portion of the first clip portion.

25. The orthodontic bracket of claim 17, wherein the locking member and/or the receiving member includes a first projection that extends transverse to the sliding movement of the resilient ligating clip and that has an asymmetric shape about a plane that is substantially perpendicular to the sliding movement of the resilient ligating clip.

26. An orthodontic bracket for coupling an archwire with a tooth, comprising:
a bracket body adapted to be mounted to the tooth and including an archwire slot adapted to receive the archwire therein, the archwire slot including a base surface and two opposing side walls extending away from the base surface; and
a resilient U-shaped ligating clip that is slidably engageable with the bracket body so as to have an opened position and a closed position, one portion of the resilient U-shaped ligating clip has a free end that extends therefrom and an outwardly facing surface and, in the closed position, the outwardly facing surface faces away from the base surface and another portion of the resilient U-shaped ligating clip is between the archwire slot and the tooth when the orthodontic bracket is placed on the tooth,
wherein the bracket body is configured to limit deflection of the resilient U-shaped ligating clip away from the base surface by contact between the bracket body and the surface that faces away from the base surface and without contacting the free end.

27. The orthodontic bracket of claim 26 wherein the bracket body includes a clip receptacle that is configured to receive the free end of the resilient U-shaped ligating clip when the resilient U-shaped ligating clip is in the closed position.

28. The orthodontic bracket of claim 26, wherein the bracket body further includes a mesial-distal bridge that covers a portion of the resilient U-shaped ligating clip when the resilient U-shaped ligating clip is in the closed position and wherein the surface that faces away from the base surface contacts the mesial-distal bridge when the resilient U-shaped ligating clip deflects away from the base surface.

29. An orthodontic bracket for coupling an archwire with a tooth comprising:
a bracket body that is adapted to be mounted to the tooth and includes an archwire slot adapted to receive the archwire therein;
a resilient ligating clip that is slidably engageable with the bracket body and is movable relative to the bracket body between an opened position and a closed position in which the archwire slot is between two portions of the resilient ligating clip, one portion being between the archwire slot and the tooth when the orthodontic bracket is placed on the tooth; and
a securing mechanism configured to secure the resilient ligating clip in the closed position and including a locking member on one of the bracket body or the resilient ligating clip and a receiving member on the other of the bracket body or the resilient ligating clip, each of the locking member and the receiving member including a first surface and a second surface,
wherein the first surfaces contact one another when the resilient ligating clip is moved to the closed position and the second surfaces contact one another when the resilient ligating clip is moved to the opened position, contact between the first surfaces and between the second surfaces causes deflection of the locking member, and wherein the orientation of the first surfaces and the second surfaces relative to the sliding movement of the resilient ligating clip causes the force to move the resilient ligating clip from the opened position to the closed position to be less than the force to move the resilient ligating clip from the closed position to the opened position.

* * * * *